United States Patent
Teufel et al.

(10) Patent No.: US 11,814,447 B2
(45) Date of Patent: Nov. 14, 2023

(54) PEPTIDE LIGANDS FOR BINDING TO EPHA2

(71) Applicant: BICYCLERD LIMITED, Cambridge (GB)

(72) Inventors: Daniel Paul Teufel, Cambridge (GB); Gemma Mudd, Cambridge (GB); Silvia Pavan, Cambridge (GB)

(73) Assignee: BicycleRD Limited, Cambridge (GB)

( * ) Notice: Subject to any disclaimer, the term of this patent is extended or adjusted under 35 U.S.C. 154(b) by 0 days.

(21) Appl. No.: 17/254,350

(22) PCT Filed: Jun. 18, 2019

(86) PCT No.: PCT/EP2019/065993
§ 371 (c)(1),
(2) Date: Dec. 21, 2020

(87) PCT Pub. No.: WO2019/243313
PCT Pub. Date: Dec. 26, 2019

(65) Prior Publication Data
US 2021/0261620 A1    Aug. 26, 2021

(30) Foreign Application Priority Data
Jun. 22, 2018 (GB) ................................. 1810316

(51) Int. Cl.
C07K 7/08 (2006.01)
A61K 47/64 (2017.01)
A61K 38/00 (2006.01)

(52) U.S. Cl.
CPC ............. *C07K 7/08* (2013.01); *A61K 47/64* (2017.08); *A61K 38/00* (2013.01)

(58) Field of Classification Search
CPC ........... C07K 7/08; A61K 47/64; A61K 38/00
See application file for complete search history.

(56) References Cited

U.S. PATENT DOCUMENTS

| | | | |
|---|---|---|---|
| 4,650,750 | A | 3/1987 | Giese |
| 4,709,016 | A | 11/1987 | Giese |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 6,326,144 | B1 | 12/2001 | Bawendi et al. |
| 6,468,808 | B1 | 10/2002 | Nie et al. |
| 7,151,047 | B2 | 12/2006 | Chan et al. |
| 7,192,785 | B2 | 3/2007 | Nie et al. |
| 8,138,347 | B2 | 3/2012 | Knight et al. |
| 8,680,022 | B2 | 3/2014 | Gregory et al. |
| 8,685,890 | B2 | 4/2014 | Winter et al. |
| 8,778,844 | B2 | 7/2014 | Winter et al. |
| 9,518,081 | B2 | 12/2016 | Winter et al. |
| 9,644,201 | B2 | 5/2017 | Winter et al. |
| 9,657,288 | B2 | 5/2017 | Winter et al. |
| 9,670,482 | B2 | 6/2017 | Winter et al. |
| 9,670,484 | B2 | 6/2017 | Winter et al. |
| 9,868,767 | B2 | 1/2018 | Pei et al. |
| 9,932,367 | B2 | 4/2018 | Stace et al. |
| 9,994,617 | B2 | 6/2018 | Tite et al. |
| 10,118,947 | B2 | 11/2018 | Teufel et al. |
| 10,294,274 | B2 | 5/2019 | Teufel et al. |
| 10,441,663 | B2 | 10/2019 | Bennett et al. |
| 10,532,106 | B2 | 1/2020 | Teufel et al. |
| 10,624,968 | B2 | 4/2020 | Bennett et al. |
| 10,800,813 | B2 | 10/2020 | Tite et al. |
| 10,875,894 | B2 | 12/2020 | Chen et al. |
| 10,919,937 | B2 | 2/2021 | Beswick et al. |
| 11,306,123 | B2 | 4/2022 | Mudd et al. |
| 11,312,749 | B2 | 4/2022 | Mudd et al. |

(Continued)

FOREIGN PATENT DOCUMENTS

WO   WO-2001042246 A2   6/2001
WO   WO-2002088112 A1   11/2002

(Continued)

OTHER PUBLICATIONS

Annunziata et al., "Phase 1, open-label study of MEDI-547 in patients with relapsed or refractory solid tumors," Invest. New. Drugs. 2013;31(1):77-84.

(Continued)

*Primary Examiner* — Amber D Steele
(74) *Attorney, Agent, or Firm* — Dechert LLP; Andrea L. C. Reid; Gang Wang

(57) ABSTRACT

A peptide ligand specific for EphA2 comprising a polypeptide comprising three residues selected from cysteine, L-2, 3-diaminopropionic acid (Dap), N-beta-alkyl-L-2,3-diaminopropionic acid (N-AlkDap) and N-beta-haloalkyl-L-2,3-diaminopropionic acid (N-HAlkDap), with the proviso that at least one of said three residues is selected from Dap, N-AlkDap or N-HAlkDap, the said three residues being separated by at least two loop sequences, and a molecular scaffold, the peptide being linked to the scaffold by covalent alkylamino linkages with the Dap or N-AlkDap or N-HAlk-Dap residues of the polypeptide and by thioether linkages with the cysteine residues of the polypeptide when the said three residues include cysteine, such that two polypeptide loops are formed on the molecular scaffold.

19 Claims, 3 Drawing Sheets

Specification includes a Sequence Listing.

(56) References Cited

U.S. PATENT DOCUMENTS

| | | | |
|---|---|---|---|
| 11,332,500 B2 | 5/2022 | Mudd et al. | |
| 2002/0164788 A1 | 11/2002 | Ellis et al. | |
| 2005/0169931 A1 | 8/2005 | Kinch et al. | |
| 2009/0304721 A1* | 12/2009 | Kinch | A61K 47/6811 |
| | | | 435/320.1 |
| 2012/0101253 A1* | 4/2012 | Heinis | A61K 47/64 |
| | | | 530/317 |
| 2015/0038434 A1* | 2/2015 | Yang | A61P 3/04 |
| | | | 514/21.1 |
| 2016/0031939 A1* | 2/2016 | Stace | G01N 33/6803 |
| | | | 530/345 |
| 2017/0067045 A1 | 3/2017 | Winter et al. | |
| 2017/0190743 A1* | 7/2017 | Pei | A61K 38/12 |
| 2017/0306032 A1* | 10/2017 | Gehlsen | C07K 16/2866 |
| 2018/0311300 A1 | 11/2018 | Beswick et al. | |
| 2018/0362585 A1 | 12/2018 | Teufel et al. | |
| 2018/0371020 A1 | 12/2018 | Bennett et al. | |
| 2019/0134213 A1 | 5/2019 | Teufel et al. | |
| 2019/0184025 A1 | 6/2019 | Chen et al. | |
| 2019/0263866 A1 | 8/2019 | Chen et al. | |
| 2019/0307836 A1 | 10/2019 | Keen et al. | |
| 2019/0389906 A1 | 12/2019 | Beswick et al. | |
| 2020/0255477 A1 | 8/2020 | Chen et al. | |
| 2020/0338203 A1 | 10/2020 | Chen et al. | |
| 2020/0354406 A1 | 11/2020 | Stephen et al. | |
| 2021/0040154 A1 | 2/2021 | Mudd et al. | |
| 2021/0069287 A1 | 3/2021 | Mudd et al. | |
| 2021/0101932 A1 | 4/2021 | Chen et al. | |
| 2021/0101933 A1 | 4/2021 | Chen et al. | |
| 2021/0101937 A1 | 4/2021 | Mudd et al. | |
| 2021/0147484 A1 | 5/2021 | Beswick et al. | |
| 2021/0261620 A1 | 8/2021 | Teufel et al. | |
| 2021/0299210 A2 | 9/2021 | Keen et al. | |
| 2022/0184222 A1 | 6/2022 | Bennett et al. | |
| 2022/0227811 A1 | 7/2022 | Mudd et al. | |

FOREIGN PATENT DOCUMENTS

| | | |
|---|---|---|
| WO | WO-2003063794 A2 | 8/2003 |
| WO | WO-2004005348 A1 | 1/2004 |
| WO | WO-2004019973 A1 | 3/2004 |
| WO | WO-2004077062 A2 | 9/2004 |
| WO | WO-2004089925 A1 | 10/2004 |
| WO | WO-2005007623 A2 | 1/2005 |
| WO | WO-2005103083 A2 | 11/2005 |
| WO | WO-2005113554 A2 | 12/2005 |
| WO | WO-2006078161 A1 | 7/2006 |
| WO | WO-2006078846 A1 | 7/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008033561 A2 | 3/2008 |
| WO | WO-2008039218 A2 | 4/2008 |
| WO | WO-2008109943 A1 | 9/2008 |
| WO | WO-2008157490 A1 | 12/2008 |
| WO | 2009098450 A2 | 8/2009 |
| WO | WO-2009114512 A1 | 9/2009 |
| WO | WO-2010089115 A1 | 8/2010 |
| WO | WO-2011018227 A2 | 2/2011 |
| WO | WO-2011090760 A1 | 7/2011 |
| WO | WO-2012057624 A1 | 5/2012 |
| WO | WO-2013050617 A1 | 4/2013 |
| WO | WO-2014164693 A2 | 10/2014 |
| WO | WO-2015171938 A1 | 11/2015 |
| WO | 2016067035 A1 | 5/2016 |
| WO | WO-2016171242 A1 | 10/2016 |
| WO | WO-2016174103 A1 | 11/2016 |
| WO | WO-2017161069 A1 | 9/2017 |
| WO | WO-2017173408 A1 | 10/2017 |
| WO | WO-2017182672 A1 | 10/2017 |
| WO | 2017191460 A1 | 11/2017 |
| WO | 2018115203 A1 | 6/2018 |
| WO | WO-2018115204 A1 | 6/2018 |
| WO | WO-2018127699 A1 | 7/2018 |
| WO | WO-2018156740 A1 | 8/2018 |
| WO | WO-2018197509 A1 | 11/2018 |
| WO | WO-2019025811 A1 | 2/2019 |
| WO | 2019122860 A1 | 6/2019 |
| WO | 2019122861 A1 | 6/2019 |
| WO | 2019122863 A1 | 6/2019 |
| WO | WO-2019162682 A1 | 8/2019 |
| WO | 2019193328 A1 | 10/2019 |
| WO | 2019243313 A1 | 12/2019 |
| WO | WO-2019243832 A1 | 12/2019 |
| WO | WO-2019243833 A1 | 12/2019 |
| WO | 2020084305 A1 | 4/2020 |
| WO | WO-2020128526 A1 | 6/2020 |
| WO | 2020201753 A1 | 10/2020 |
| WO | WO-2020225577 A1 | 11/2020 |
| WO | 2021019243 A1 | 2/2021 |
| WO | 2021019245 A1 | 2/2021 |
| WO | 2021064428 A1 | 4/2021 |
| WO | 2021105694 A1 | 6/2021 |
| WO | 2021250418 A1 | 12/2021 |

OTHER PUBLICATIONS

Bennett et al., "Abstract 5855: Bicycle Drug Conjugates Targeting EphA2 for the Treatment of Solid Tumors: Discovery and Selection of BT5528," Cancer Research, 2018, 4 Pages.

Bennett et al., "Development of BT1718, a Bicycle Drug Conjugate (BDC) targeting MT1-MMP for treatment of solid tumours," European Journal of Cancer. 2016;69(1):S21.

Bennett et al., "Development of BT1718, a Bicycle Drug Conjugate (BTC): Profound Efficacy Without Bleeding and Coagulation Abnormalities in Animal Models," Assocation for Cancer Research Annual Meeting, 2019, 11 pages.

Bennett, "BT5528, an EphA2-Targeting Bicycle Toxin Conjugate (BTC): Profound Efficacy Without Bleeding and Coagulation Abnormalities in Animal Models," Association for Cancer Research Annual Meeting, 2019, 11 Pages.

Chen et al., "Peptide Ligands Stabilized by Small Molecules," Angewandte Chemie International Edition. 2014;56(6):1602-1606.

Deonarain et al., "Small-Format Drug Conjugates: A Viable Alternative to ADCs for Solid Tumours?" Antibodies (Basel). 2018;7(2):16.

Deyle et al., "Phage Selection of Cyclic Peptides for Application in Research and Drug Development," Accounts of Chemical Research, 2017, vol. 50(8), pp. 1866-1874.

Harrison et al., "Abstract 5144: BT1718, a novel bicyclic peptide-maytansinoid conjugate targeting MT1-MMP for the treatment of solid tumors: Design of bicyclic peptide and linker selection," Cancer Res. 2017;77(13):5144.

Mitra et al., "Structure-Activity Relationship Analysis of Peptides Targeting the EphA2 Receptor," Biochemistry. 2010;49(31):6687-95.

Mudd et al., "Identification and Optimization of EphA2-Selective Biccyles for the Delivery of Cytotoxic Payloads," J Med Chem. 2020; 63(8) 4107-4116.

PCT International Search Report and Written Opinion for PCT/GB2018/053678 dated Mar. 20, 2019.

PCT International Search Report for PCT Application No. PCT/EP2019/065993, mailed by the European Patent Office dated Sep. 24, 2019, 5 Pages.

PCT International Search Report for PCT Application No. PCT/GB2020/051829, mailed by the European Patent Office dated Oct. 30, 2020, 5 Pages.

Shi et al., "One-Bead-Two-Compound Thioether Bridged Macrocyclic [gamma]—AApeptide Screening Library Against EphA2," J. Med. Chem. 2017;60(22):9290-9298.

U.S. Appl. No. 16/771,186, filed Jun. 9, 2020.
U.S. Appl. No. 17/590,875, filed Feb. 2, 2022.
U.S. Appl. No. 17/592,966, filed Feb. 4, 2022.
U.S. Appl. No. 17/630,314, filed Jan. 26, 2022.
U.S. Appl. No. 17/630,747, filed Jan. 27, 2022.

(56) References Cited

OTHER PUBLICATIONS

U.S. Appl. No. 17/655,822, filed Mar. 22, 2022.
U.S. Appl. No. 17/663,169, filed May 12, 2022.
U.S. Appl. No. 17/779,226, filed May 24, 2022.
Wu et al., "Design and Characterization of Novel EphA2 Agonists for Targeted Delivery of Chemotherapy to Cancer Cells," Chem. Biol. 2015;22(7):876-887.
Adams, "Molecular control of arterial-venous blood vessel identity," J Anat. Jan. 2003;202(1):105-12.
Ausiello et al., "Functional topography of discrete domains of human CD38," Tissue Antigens. Dec. 2000;56(6):539-47.
Bennett et al., "Abstract 5854: BT5528, a Bicycle Toxin Conjugate targeting EphA2 has potent anti-tumor activity without bleeding or coagulation abnormalities in preclinical models." Cancer Res. 2018;78(13 suppl):5854.
Bennett et al., "BT5528, a Bicycle Toxin Conjugate targeting EphA2 has potent anti-tumor activity without bleeding or coagulation abnormalities in preclinical models," AACR Annual Meeting 2018.
Bennett et al., "MMAE Delivery Using the Bicycle Toxin Conjugate BT5528," Mol Cancer Ther. Jul. 2020;19(7):1385-1394.
Berge et al., "Pharmaceutical salts," J Pharm Sci. Jan. 1977;66(1):1-19.
Bicycle Therapeutics, "Bicycle Therapeutics to Present New BT1718 Data in the 'New Drugs on the Horizon' Session at the 2018 American Association for Cancer Research Meeting," Press Release. Apr. 3, 2018: https://www.businesswire.com/news/home/20180403005152/en/Bicycle-Therapeutics-Present-New-BT1718-Data-New.
Bicycle Therapeutics, "Bicycle Therapeutics to Present on BT5528, a Bicycle Toxin Conjugate Targeting EphA2 for the Treatment of Solid Tumours, at World ADC 2019," Business Wire Release. Mar. 5, 2019.
Bicycle Therapeutics, "Bicycle Therapeutics to Present New BT1718 Data in the "New Drugs on the Horizon" Session at the 2018 American Association for Cancer Research Meeting," Press Release. Apr. 3, 2018.
BicycleTx Limited, "Study BT5528-100 in Patients With Advanced Solid Tumors Associated With EphA2 Expression," ClinicalTrials.gov Identifier NCT04180371. First Posted Nov. 27, 2019; Accessed Dec. 30, 2022: https://clinicaltrials.gov/ct2/show/NCT04180371.
Binda et al., "The EphA2 receptor drives self-renewal and tumorigenicity in stem-like tumor-propagating cells from human glioblastomas," Cancer Cell. Dec. 11, 2012;22(6):765-80.
Booth et al., "Crowd control in the crypt," Nat Med. Dec. 2002;8(12):1360-1.
Brannan et al., "EphA2 in the early pathogenesis and progression of non-small cell lung cancer," Cancer Prev Res (Phila). Dec. 2009;2(12):1039-49.
Brantley-Sieders et al., "Eph receptor tyrosine kinases in tumor and tumor microenvironment," Curr Pharm Des. 2004;10(27):3431-42.
Brantley-Sieders et al., "Eph/ephrin profiling in human breast cancer reveals significant associations between expression level and clinical outcome," PLOS One. 2011;6(9):e24426.
Brantley-Sieders et al., "Impaired tumor microenvironment in EphA2-deficient mice inhibits tumor angiogenesis and metastatic progression," FASEB J. Nov. 2005;19(13):1884-6.
Centers for Disease Control and Prevention, "What Can I Do to Reduce My Risk of Ovarian Cancer?" Division of Cancer Prevention and Control. Aug. 31, 2022.
Chan and Nie, "Quantum dot bioconjugates for ultrasensitive nonisotopic detection," Science. Sep. 25, 1998;281(5385):2016-8.
Chang et al., "Five different anti-prostate-specific membrane antigen (PSMA) antibodies confirm PSMA expression in tumor-associated neovasculature," Cancer Res. Jul. 1, 1999;59(13):3192-8.
Chen et al., "Structurally diverse cyclisation linkers impose different backbone conformations in bicyclic peptides," Chembiochem. May 7, 2012;13(7):1032-8.
Cheng et al., "Blockade of EphA receptor tyrosine kinase activation inhibits vascular endothelial cell growth factor-induced angiogenesis," Mol Cancer Res. Nov. 2002;1(1):2-11.
Cherney et al., "Macrocyclic amino carboxylates as selective MMP-8 inhibitors," J Med Chem. May 21, 1998;41(11):1749-51.
Chiche et al., "Hypoxia-inducible carbonic anhydrase IX and XII promote tumor cell growth by counteracting acidosis through the regulation of the intracellular pH," Cancer Res. Jan. 1, 2009;69(1):358-68.
Dagher et al., "c-Kit and CD38 are expressed by long-term reconstituting hematopoietic cells present in the murine yolk sac," Biol Blood Marrow Transplant. 1998;4(2):69-74.
Deaglio et al., "CD38 is a signaling molecule in B-cell chronic lymphocytic leukemia cells," Blood. Sep. 15, 2003;102(6):2146-55.
Deyle et al., "Phage Selection of Cyclic Peptides for Application in Research and Drug Development." Acc Chem Res. 2017;50(8):1866-1874.
Di, "Strategic approaches to optimizing peptide ADME properties," AAPS J. Jan. 2015;17(1):134-43.
Driggers et al., "The exploration of macrocycles for drug discovery—an underexploited structural class," Nat Rev Drug Discov. Jul. 2008;7(7):608-24.
Dunne et al., "EphA2 Expression Is a Key Driver of Migration and Invasion and a Poor Prognostic Marker in Colorectal Cancer," Clin Cancer Res. Jan. 1, 2016;22(1):230-242.
Duong and Rodan, "The role of integrins in osteoclast function," J Bone Miner Metab. 1999;17(1):1-6.
Funaro et al., "Human CD38 is associated to distinct molecules which mediate transmembrane signaling in different lineages," Eur J Immunol. Oct. 1993;23(10):2407-11.
Funaro et al., "Involvement of the multilineage CD38 molecule in a unique pathway of cell activation and proliferation," J Immunol. Oct. 15, 1990;145(8):2390-6.
Gandhi et al., "MP69-11 Carbonic Anhydrase IX Assay: A Paradigm Shift in Diagnosis of Malignant Cystic Renal Lesions," J Urol. May 18, 2015;193(4S):e870-e871.
Guo et al., "Prognostic significance of combinations of RNA-dependent protein kinase and EphA2 biomarkers for NSCLC," J Thorac Oncol. Mar. 2013;8(3):301-8.
Heinis et al., "Phage-encoded combinatorial chemical libraries based on bicyclic peptides," Nat. Chem. Biol. 2009;5(7):502-7.
Hess et al., "Molecular regulation of tumor cell vasculogenic mimicry by tyrosine phosphorylation: role of epithelial cell kinase (Eck/EphA2)," Cancer Res. Apr. 15, 2001;61(8):3250-5.
Hoshino et al., "Mapping of the catalytic and epitopic sites of human CD38/NAD+ glycohydrolase to a functional domain in the carboxyl terminus," J Immunol. Jan. 15, 1997;158(2):741-7.
PCT International Search Report and Written Opinion from PCT/GB2020/051827, dated Oct. 23, 2020.
Jackson et al., "A human antibody-drug conjugate targeting EphA2 inhibits tumor growth in vivo," Cancer Res. Nov. 15, 2008;68(22):9367-74.
Jin et al., "(alpha)V(beta)3 Integrin-Targeted Radionuclide Therapy with 64Cu-cyclam-RAFT-c(-RGDfK-)4," Mol Cancer Ther. Sep. 2016;15(9):2076-85.
Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog," J Org Chem. 1985;50(26):5834-8.
Kinch et al., "Predictive value of the EphA2 receptor tyrosine kinase in lung cancer recurrence and survival," Clin Cancer Res. Feb. 2003;9(2):613-8.
Kitanaka et al., "CD38 ligation in human B cell progenitors triggers tyrosine phosphorylation of CD19 and association of CD19 with lyn and phosphatidylinositol 3-kinase," J Immunol. Jul. 1, 1997;159(1):184-92.
Kitanaka et al., "CD38-mediated signaling events in murine pro-B cells expressing human CD38 with or without its cytoplasmic domain," J Immunol. Feb. 15, 1999;162(4):1952-8.
Konopleva et al., "Ligation of cell surface CD38 protein with agonistic monoclonal antibody induces a cell growth signal in myeloid leukemia cells," J Immunol. Nov. 1, 1998;161(9):4702-8.

(56) References Cited

OTHER PUBLICATIONS

Kumagai et al., "Ligation of CD38 suppresses human B lymphopoiesis," J Exp Med. Mar. 1, 1995;181(3):1101-10.
Lee and Aarhus, "ADP-ribosyl cyclase: an enzyme that cyclizes NAD+ into a calcium-mobilizing metabolite," Cell Regul. Mar. 1991;2(3):203-9.
Lee et al., "ADP-ribosyl cyclase and CD38. Multi-functional enzymes in Ca+2 signaling," Adv Exp Med Biol. 1997;419:411-9.
Lee et al., "Structural determination of a cyclic metabolite of NAD+ with intracellular Ca2+—mobilizing activity," J Biol Chem. Jan. 25, 1989;264(3):1608-15.
Li et al., "Up-regulation of EphA2 and down-regulation of EphrinA1 are associated with the aggressive phenotype and poor prognosis of malignant glioma," Tumour Biol. Oct. 2010;31(5):477-88.
Lin et al., "EphA2 overexpression is associated with angiogenesis in ovarian cancer," Cancer. Jan. 15, 2007;109(2):332-40.
Loktev et al., "Multicyclic Peptides as Scaffolds for the Development of Tumor Targeting Agents," Current Medicinal Chemistry, 2017, vol. 24, pp. 2141-2155.
Lund et al., "CD38 signaling in B lymphocytes is controlled by its ectodomain but occurs independently of enzymatically generated ADP-ribose or cyclic ADP-ribose," J Immunol. Mar. 1, 1999;162(5):2693-702.
Mallone et al., "Signaling through CD38 induces NK cell activation," Int Immunol. Apr. 1, 2001;13(4):397-409.
Marmé, "VEGFs, angiopoietins, Ephrins and their receptors: putative targets for tumor therapy?" Ann Hematol. 2002;81 Suppl 2:S66.
Merritt et al., "Analysis of EphA2 expression and mutant p53 in ovarian carcinoma," Cancer Biol Ther. Oct. 2006;5(10):1357-60.
Morra et al., "CD38 is functionally dependent on the TCR/CD3 complex in human T cells," FASEB J. May 1998;12(7):581-92.
Morrison, "Chemical Strategies for Bicyclic Peptide Formation," Univ. of Leeds, Sep. 2015, pp. 1-60.
Mudali et al., "Patterns of EphA2 protein expression in primary and metastatic pancreatic carcinoma and correlation with genetic status," Clin Exp Metastasis. 2006;23(7-8):357-65.
Mulder et al., "Scaffold Optimization in Discontinuous Epitope Containing Protein Mimics of gp120 Using Smart Libraries," Org. Biomol. Chem. 2013, vol. 11, pp. 2676-2684.
Nakamoto and Bergemann, "Diverse roles for the Eph family of receptor tyrosine kinases in carcinogenesis," Microsc Res Tech. Oct. 1, 2002;59(1):58-67.
Nakamura et al., "EPHA2/EFNA1 expression in human gastric cancer," Cancer Sci. Jan. 2005;96(1):42-7.
Nakamura et al., "Involvement of alpha(v)beta3 integrins in osteoclast function," J Bone Miner Metab. 2007;25(6):337-44.
Nan et al., "Dual function glutamate-related ligands: discovery of a novel, potent inhibitor of glutamate carboxypeptidase II possessing mGluR3 agonist activity," J Med Chem. Mar. 9, 2000;43(5):772-4.
Neri and Supuran, "Interfering with pH regulation in tumours as a therapeutic strategy," Nat Rev Drug Discov. Sep. 16, 2011;10(10):767-77.
Oliver et al., "Mouse CD38 is down-regulated on germinal center B cells and mature plasma cells," J Immunol. Feb. 1, 1997;158(3):1108-15.
Partida-Sánchez et al., "Cyclic ADP-ribose production by CD38 regulates intracellular calcium release, extracellular calcium influx and chemotaxis in neutrophils and is required for bacterial clearance in vivo," Nat Med. Nov. 2001;7(11):1209-16.
Partida-Sánchez et al., "Regulation of dendritic cell trafficking by the ADP-ribosyl cyclase CD38: impact on the development of humoral immunity," Immunity. Mar. 2004;20(3):279-91.
PCT International Search Report and Written Opinion from PCT/GB2018/053676, dated Mar. 21, 2019.
PCT International Search Report and Written Opinion from PCT/GB2018/051779, dated Aug. 23, 2018.
PCT International Search Report and Written Opinion from PCT/GB2020/050874 dated Jun. 17, 2020.
PCT International Search Report and Written Opinion from PCT/GB2021/051451 dated Sep. 22, 2021.
Pickens et al., "Practical Considerations, Challenges and Limitations of Bioconjugation via Azide-Alkyne Cycloaddition," Bioconjugate Chem., 2018, vol. 29, pp. 686-701.
Pietraszek et al., "Lumican: a new inhibitor of matrix metalloproteinase-14 activity," FEBS Lett. Nov. 28, 2014;588(23):4319-24.
Poliakov et al., "Diverse roles of eph receptors and ephrins in the regulation of cell migration and tissue assembly," Dev Cell. Oct. 2004;7(4):465-80.
Ramirez et al., "Defining causative factors contributing in the activation of hedgehog signaling in diffuse large B-cell lymphoma," Leuk Res. Oct. 2012;36(10):1267-73.
Randall et al., "Expression of murine CD38 defines a population of long-term reconstituting hematopoietic stem cells," Blood, vol. 87, No. 10, May 1996 (pp. 4057-4067).
Remacle et al., "Novel MT1-MMP small-molecule inhibitors based on insights into hemopexin domain function in tumor growth," Cancer Res. May 1, 2012;72(9):2339-49.
Rhodes and Pei, "Bicyclic Peptides as Next-Generation Therapeutics," Chemistry. Sep. 18, 2017;23(52):12690-12703.
Ridderstad and Tarlinton, "Kinetics of establishing the memory B cell population as revealed by CD38 expression," J Immunol. May 15, 1998;160(10):4688-95.
Rodan and Rodan, "Integrin function in osteoclasts," J Endocrinol. Sep. 1997;154 Suppl:S47-56.
Ross and Christiano, "Nothing but skin and bone," J Clin Invest. May 2006;116(5):1140-9.
Rostovtsev et al., "A stepwise huisgen cycloaddition process: copper(I)-catalyzed regioselective "ligation" of azides and terminal alkynes," Angew Chem Int Ed Engl. Jul. 15, 2002;41(14):2596-9.
Schülke et al., "The homodimer of prostate-specific membrane antigen is a functional target for cancer therapy," Proc Natl Acad Sci U S A. Oct. 28, 2003;100(22):12590-5.
Smeenk et al., "Reconstructing the discontinuous and conformational (beta)1/(beta)3-loop binding site on hFSH/hCG by using highly constrained multicyclic peptides," Chembiochem. Jan. 2, 2015;16(1):91-9.
Sounni et al., "MT1-MMP expression promotes tumor growth and angiogenesis through an up-regulation of vascular endothelial growth factor expression," FASEB J. Apr. 2002;16(6):555-64.
Stein et al., "Eph receptors discriminate specific ligand oligomers to determine alternative signaling complexes, attachment, and assembly responses," Genes Dev. Mar. 1, 1998;12(5):667-678.
Stevenson et al., "Preliminary studies for an immunotherapeutic approach to the treatment of human myeloma using chimeric anti-CD38 antibody," Blood. Mar. 1, 1991;77(5):1071-9.
Sun et al., "Carbohydrate and protein immobilization onto solid surfaces by sequential Diels-Alder and azide-alkyne cycloadditions," Bioconjug Chem. Jan.-Feb. 2006;17(1):52-7.
Supuran, "Carbonic anhydrases: novel therapeutic applications for inhibitors and activators," Nat Rev Drug Discov. Feb. 2008; 7(2):168-81.
Tandon et al., "Emerging strategies for EphA2 receptor targeting for cancer therapeutics." Expert Opin Ther Targets. 2011;15(1):31-51.
Tasch et al., "A unique folate hydrolase, prostate-specific membrane antigen (PSMA): a target for immunotherapy?" Crit Rev Immunol. 2001;21(1-3):249-61.
Teitelbaum, "Osteoclasts, integrins, and osteoporosis," Journal of Bone and Mineral Metabolism, vol. 18, No. 6, Oct. 2000 (pp. 344-349).
Teitelbaum, "Osteoporosis and Integrins," J Clin Endocrinol Metab. Apr. 2005;90(4):2466-8.
Teti et al., "The Role of the AlphaVbeta3 Integrin in the Development of Osteolytic Bone Metastases: A Pharmacological Target for Alternative Therapy?" Calcified Tissue International, vol. 71, No. 4, Oct. 2002 (pp. 293-299).
Teufel et al., "Backbone-driven collapse in unfolded protein chains," Journal of Molecular Biology, vol. 409, No. 2, Jun. 2011 (pp. 250-262).
Timmerman et al., "Rapid and quantitative cyclization of multiple peptide loops onto synthetic scaffolds for structural mimicry of protein surfaces," Chembiochem. May 2005;6(5):821-4.
Todisco et al., "CD38 ligation inhibits normal and leukemic myelopoiesis," Blood, vol. 95, No. 2, Jan. 2000 (pp. 535-542).

(56) References Cited

OTHER PUBLICATIONS

Uckun, "Regulation of Human B-Cell Ontogeny," Blood, vol. 76, No. 10, Nov. 1990 (pp. 1908-1923).

Upadhyaya, "Activation of CD137 Using Multivalent and Tumour Targeted Bicyclic Peptides," XP055669343, URL:https://www.bicycletherapeutics.com/wp-content/uploads/PU_2019-Peptide-Congress_publication.pdf, Peptide Congress, Apr. 25, 2019, 25 Pages.

Walker-Daniels et al., "Overexpression of the EphA2 tyrosine kinase in prostate cancer," Prostate, vol. 41, No. 4, Dec. 1999 (pp. 275-280).

Wang et al., "Probing for Integrin ?v?3 Binding of RGD Peptides Using Fluorescence Polarization," Bioconjugate Chemistry, vol. 16, No. 3, May-Jun. 2005 (pp. 729-734).

Wang, "An exact mathematical expression for describing competitive binding of two different ligands to a protein molecule," FEBS Lett. Feb. 27, 1995;360(2):111-4.

Wind et al., "Measuring carbonic anhydrase IX as a hypoxia biomarker: differences in concentrations in serum and plasma using a commercial enzyme-linked immunosorbent assay due to influences of metal ions," Ann Clin Biochem. Mar. 2011;48(Pt 2):112-20.

Wu et al., "Structures of the CXCR4 chemokine GPCR with small-molecule and cyclic peptide antagonists," Science. Nov. 19, 2010;330(6007):1066-71.

Wykosky et al., "EphA2 as a Novel Molecular Marker and Target in Glioblastoma Multiforme," Molecular Cancer Research, vol. 3, No. 10, Oct. 2005 (pp. 541-551).

Xiong et al., "Crystal structure of the extracellular segment of integrin alpha Vbeta3 in complex with an Arg-Gly-Asp ligand," Science. Apr. 5, 2002;296(5565):151-5.

Yang et al., "Overexpression of EphA2, MMP?9, and MVD?CD34 in hepatocellular carcinoma: Implications for tumor progression and prognosis," Hepatology Research, vol. 39, No. 12, Dec. 2009 (pp. 1169-1177).

Yuan et al., "Over-Expression of EphA2 and EphrinA-1 in Human Gastric Adenocarcinoma and Its Prognostic Value for Postoperative Patients," Digestive Diseases and Sciences, vol. 54, No. 11, Nov. 2009 (pp. 2410-2417).

Zelinski et al., "EphA2 overexpression causes tumorigenesis of mammary epithelial cells," Cancer Research, vol. 61, No. 5, Mar. 2001 (pp. 2301-2306).

Zhao et al., "Structural basis of specificity of a peptidyl urokinase inhibitor, upain-1," J Struct Biol. Oct. 2007;160(1):1-10.

Zhuang et al., "Elevation of receptor tyrosine kinase EphA2 mediates resistance to trastuzumab therapy," Cancer Research, vol. 70, No. 1, Jan. 2010 (pp. 299-308).

Zilber et al., "CD38 expressed on human monocytes: A coaccessory molecule in the superantigen-induced proliferation," Proceedings of the National Academy of Sciences of the United States of America, vol. 97, No. 6, Mar. 2000 (pp. 2840-2845).

Zubiaur et al., "CD38 ligation results in activation of the Raf-1/mitogen-activated protein kinase and the CD3-zeta/zeta-associated protein-70 signaling pathways in Jurkat T lymphocytes," Journal of Immunology, vol. 159, No. 1, Jul. 1997 (pp. 193-205).

Zupo et al., "CD38 signaling by agonistic monoclonal antibody prevents apoptosis of human germinal center B cells," European Journal of Immunology, vol. 24, No. 5, May 1994 (pp. 1218-1222).

\* cited by examiner

PEPTIDE LIGANDS FOR BINDING TO EPHA2

CROSS-REFERENCE TO RELATED APPLICATIONS

This application is a U.S. national stage application under 35 U.S.C. § 371 of International Application No. PCT/EP2019/065993, filed Jun. 18, 2019, which claims priority under 35 U.S.C. § 119 to United Kingdom Application No. GB1810316.8, filed Jun. 22, 2018, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 15, 2022, is named 178093 SL.txt and is 101,524 bytes in size.

TECHNICAL FIELD

The present invention relates to peptide ligands showing high binding affinity to the Eph receptor tyrosine kinase A2 (EphA2). The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder characterised by overexpression of EphA2 in diseased tissue (such as a tumour).

In particular, the invention relates to peptide ligands of this type having novel chemistries for forming two or more bonds between a peptide and a scaffold molecule.

BACKGROUND OF THE INVENTION

Different research teams have previously tethered peptides to scaffold moieties by forming two or more thioether bonds between cysteine residues of the peptide and suitable functional groups of a scaffold molecule. For example, methods for the generation of candidate drug compounds by linking cysteine-containing peptides to a molecular scaffold as for example tris(bromomethyl) benzene are disclosed in WO 2004/077062 and WO 2006/078161.

The advantage of utilising cysteine thiols for generating covalent thioether linkages in order to achieve cyclisation resides is their selective and biorthogonal reactivity. Thiol-containing linear peptides may be cyclised with a thiol-reactive scaffold compound such as 1, 3, 5 tris-bromomethylbenzene (TBMB) to form Bicyclic Peptides, and the resultant product contains three thioethers at the benzylic locations. The overall reaction of the linear peptide with TBMB to form a looped bicyclic peptide with thioether linkages is shown in FIG. 1.

A need exists for alternative chemistries for coupling peptides to scaffold moieties to form looped peptide structures employing suitable replacements of the thioether moiety, thereby achieving compatibility with different peptides, changes in physiochemical properties such as improved solubility, changes in biodistribution and other advantages.

WO2011/018227 describes a method for altering the conformation of a first peptide ligand or group of peptide ligands, each peptide ligand comprising at least two reactive groups separated by a loop sequence covalently linked to a molecular scaffold which forms covalent bonds with said reactive groups, to produce a second peptide ligand or group of peptide ligands, comprising assembling said second derivative or group of derivatives from the peptide(s) and scaffold of said first derivative or group of derivatives, incorporating one of: (a) altering at least one reactive group; or (b) altering the nature of the molecular scaffold; or (c) altering the bond between at least one reactive group and the molecular scaffold; or any combination of (a), (b) or (c).

Our earlier pending applications PCT/EP2017/083953 and PCT/EP2017/083954 filed 20 Dec. 2017 describe bicycle peptides in which one or more thioether linkages to the scaffold molecule have been replaced by alkylamino linkages.

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov et al. (2004) Dev Cell 7, 465-80). Functional and biochemical Eph responses occur at higher ligand oligomerization states (Stein et al. (1998) Genes Dev 12, 667-678).

Among other patterning functions, various Ephs and ephrins have been shown to play a role in vascular development. Knockout of EphB4 and ephrin-B2 results in a lack of the ability to remodel capillary beds into blood vessels (Poliakov et al., supra) and embryonic lethality. Persistent expression of some Eph receptors and ephrins has also been observed in newly-formed, adult micro-vessels (Brantley-Sieders et al. (2004) Curr Pharm Des 10, 3431-42; Adams (2003) J Anat 202, 105-12).

The de-regulated re-emergence of some ephrins and their receptors in adults also has been observed to contribute to tumor invasion, metastasis and neo-angiogenesis (Nakamoto et al. (2002) Microsc Res Tech 59, 58-67; Brantley-Sieders et al., supra). Furthermore, some Eph family members have been found to be over-expressed on tumor cells from a variety of human tumors (Brantley-Sieders et al., supra); Marme (2002) Ann Hematol 81 Suppl 2, S66; Booth et al. (2002) Nat Med 8, 1360-1).

EPH receptor A2 (ephrin type-A receptor 2) is a protein that in humans is encoded by the EPHA2 gene.

EphA2 is upregulated in multiple cancers in man, often correlating with disease progression, metastasis and poor prognosis e.g.: breast (Zelinski et al (2001) Cancer Res. 61, 2301-2306; Zhuang et al (2010) Cancer Res. 70, 299-308; Brantley-Sieders et al (2011) PLoS One 6, e24426), lung (Brannan et al (2009) Cancer Prev Res (Phila) 2, 1039-1049; Kinch et al (2003) Clin Cancer Res. 9, 613-618; Guo et al (2013) J Thorac Oncol. 8, 301-308), gastric (Nakamura et al (2005) Cancer Sci. 96, 42-47; Yuan et al (2009) Dig Dis Sci 54, 2410-2417), pancreatic (Mudali et al (2006) Clin Exp Metastasis 23, 357-365), prostate (Walker-Daniels et al (1999) Prostate 41, 275-280), liver (Yang et al (2009) Hepatol Res. 39, 1169-1177) and glioblastoma (Wykosky et al (2005) Mol Cancer Res. 3, 541-551; Li et al (2010) Tumour Biol. 31, 477-488).

The full role of EphA2 in cancer progression is still not defined although there is evidence for interaction at numerous stages of cancer progression including tumour cell growth, survival, invasion and angiogenesis. Downregulation of EphA2 expression suppresses tumour cancer cell propagation (Binda et al (2012) Cancer Cell 22, 765-780), whilst EphA2 blockade inhibits VEGF induced cell migration (Hess et al (2001) Cancer Res. 61, 3250-3255), sprouting and angiogenesis (Cheng et al (2002) Mol Cancer Res.

1, 2-11; Lin et al (2007) Cancer 109, 332-40) and metastatic progression (Brantley-Sieders et al (2005) FASEB J. 19, 1884-1886).

An antibody drug conjugate to EphA2 has been shown to significantly diminish tumour growth in rat and mouse xenograft models (Jackson et al (2008) Cancer Research 68, 9367-9374) and a similar approach has been tried in man although treatment had to be discontinued for treatment related adverse events (Annunziata et al (2013) Invest New drugs 31, 77-84).

Our earlier pending applications GB1707734.8 filed on 15 May 2017, and GB1721259.8 and GB1721265.5 both filed 19 Dec. 2017, describe bicycle peptide ligands having high binding affinity for EphA2. These applications further describe conjugates of the peptide ligands with therapeutic agents, in particular with cytotoxic agents.

SUMMARY OF THE INVENTION

The present inventors have found that replacement of thioether linkages in looped peptides having affinity for EphA2 by alkylamino linkages results in looped peptide conjugates that display similar affinities to EphA2 as the corresponding conjugates made with all thioether linkages. The replacement of thioether linkages by alkylamino linkages is expected to result in improved solubility and/or improved oxidation stability of the conjugates according to the present invention.

Accordingly, in a first aspect the present invention provides a peptide ligand specific for EphA2 comprising a polypeptide comprising three residues selected from cysteine, L-2,3-diaminopropionic acid (Dap), N-beta-alkyl-L-2,3-diaminopropionic acid (N-AlkDap) and N-beta-haloalkyl-L-2,3-diaminopropionic acid (N-HAlkDap), with the proviso that at least one of said three residues is selected from Dap, N-AlkDap or N-HAlkDap, the said three residues being separated by at least two loop sequences, and a molecular scaffold, the peptide being linked to the scaffold by covalent alkylamino linkages with the Dap or N-AlkDap or N-HAlkDap residues of the polypeptide and by thioether linkages with the cysteine residues of the polypeptide when the said three residues include cysteine, such that two polypeptide loops are formed on the molecular scaffold.

Suitably, the peptide ligand comprises an amino acid sequence selected from:

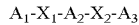

wherein:

$A_1$, $A_2$, and $A_3$ are independently cysteine, L-2,3-diaminopropionic acid (Dap), N-beta-alkyl-L-2,3-diaminopropionic acid (N-AlkDap), or N-beta-haloalkyl-L-2,3-diaminopropionic acid (N-HAlkDap), provided that at least one of $A_1$, $A_2$, and $A_3$ is Dap, N-AlkDap or N-HAlkDap; and $X_1$ and $X_2$ represent the amino acid residues between the Cysteine, Dap, N-AlkDap or N-HAlkDap residues, wherein each of $X_1$ and $X_2$ independently is a loop sequence of 4, 5, 6 or 7 amino acid residues.

It can be seen that the derivatives of the invention comprise a peptide loop coupled to a scaffold by at least one alkylamino linkage to Dap or N-AlkDap of N-HAlkDap residues and up to two thioether linkages to cysteine.

The prefix "alkyl" in N-AlkDap and N-HAlkDap refers to an alkyl group having from one to four carbon atoms, preferably methyl. The prefix "halo" is used in this context in its normal sense to signify alkyl groups having one or more, suitably one, fluoro-, chloro-, bromo- or iodo-substituents.

When cysteine is present, the thioether linkage(s) provides an anchor during formation of the cyclic peptides as explained further below. In these embodiments, the thioether linkage is suitably a central linkage of the bicyclic peptide conjugate, i.e. in the peptide sequence two residues forming alkylamino linkages in the peptide are spaced from and located on either side of a cysteine residue forming the thioether linkage. The looped peptide structure is therefore a Bicycle peptide conjugate having a central thioether linkage and two peripheral alkylamino linkages. In alternative embodiments, the thioether linkage is placed at the N-terminus or C-terminus of the peptides, the central linkage and the other terminal linkage being selected from Dap, N-AlkDap or N-HAlkDap.

In embodiments of the invention all three of $A_1$, $A_2$, and $A_3$ may suitably be Dap or N-AlkDap or N-HAlkDap. In these embodiments, the peptide ligands of the invention are suitably Bicycle conjugates having a central alkylamino linkage and two peripheral alkylamino linkages, the peptide forming two loops sharing the central alkylamino linkage. In these embodiments, $A_1$, $A_2$, and $A_3$ are suitably all selected from N-AlkDap or N-HAlkDap, most suitably N-AlkDap, because of favourable reaction kinetics with the alkylated Daps.

In embodiments, the peptide ligand of the present invention additionally comprises one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more hydrophobic amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the α-carbon of one or more amino acid residues with another chemical group, and post-synthetic bioorthogonal modification of amino acids such as cysteine, lysine, glutamate and tyrosine with suitable amine, thiol, carboxylic acid and phenol-reactive reagents.

Suitably, these embodiments may comprise an N-terminal modification using suitable amino-reactive chemistry, and/or C-terminal modification using suitable carboxy-reactive chemistry. For example, the N-terminal modification may comprise the addition of a molecular spacer group which facilitates the conjugation of effector groups and retention of potency of the bicyclic peptide to its target. The spacer group is suitably an oligopeptide group containing from about 5 to about 30 amino acids, such as an Ala, G-Sar10-A (SEQ ID NO: 1) group or bAla-Sar10-A (SEQ ID NO: 2) group. Alternatively or additionally, the N-terminal and/or C-terminal modification comprises addition of a cytotoxic agent.

In all of the peptide sequences defined herein, one or more tyrosine residues may be replaced by phenylalanine. This has been found to improve the yield of the bicycle peptide product during base-catalyzed coupling of the peptide to the scaffold molecule.

Suitably, the peptide ligand of the invention is a high affinity binder of the human, mouse and dog EphA2 hemopexin domain. Suitably the binding affinity $k_i$ is less than about 500 nM, less than about 100 nM, less than about 50 nM, less than about 25 nM, or less than about 10 nM. The binding affinity in the context of this specification is the binding affinity as measured by the methods described below.

Suitably, the peptide ligand of the invention is selective for EphA2, but does not cross-react with EphA1, EphA3 or EphA4. Suitably, the binding affinity ki with each of these ligands is greater than about 500 nM, greater than about 1000 nM, or greater than about 10000 nM.

Suitably, the scaffold comprises a (hetero)aromatic or (hetero)alicyclic moiety. Suitably, the scaffold comprises a tris-substituted (hetero)aromatic or (hetero)alicyclic moiety, for example a tris-methylene substituted (hetero)aromatic or (hetero)alicyclic moiety. The (hetero)aromatic or (hetero) alicyclic moiety is suitably a six-membered ring structure, preferably tris-substituted such that the scaffold has a 3-fold symmetry axis. Thus, in certain preferred embodiments, the scaffold is 1,3,5-tris-methylenebenzene scaffold, for example obtained by reacting the peptide with 1,3,5-tris-(bromomethyl)benzene (TBMB). In other preferred embodiments, the scaffold is a 1,3,5-tris-(acetamido)benzene group, which may be derived by coupling the peptide to 1,3,5-tris-(bromoacetamido)benzene (TBAB) as described further below.

The reactive sites are also suitable for forming thioether linkages with the —SH groups of cysteine in embodiments where the third residue is cysteine. The —SH group of cysteine is highly nucleophilic, and in these embodiments it is expected to react first with the electrophilic centres of the scaffold molecule to anchor the peptide to the scaffold molecule, whereafter the amino groups react with the remaining electrophilic centres of the scaffold molecule to form the looped peptide ligand.

In embodiments, the peptide has protecting groups on nucleophilic groups other than the amino groups and —SH groups (when present) intended for forming the alkylamino linkages.

Suitably, the peptide ligands of the invention may be made by a method that comprises reacting, in a nucleophilic substitution reaction, the peptide as defined herein with a scaffold molecule having three or more leaving groups.

In alternative methods, the compounds of the present invention could be made converting two or more side chain groups of the peptide to leaving groups, followed by reacting the peptide, in a nucleophilic substitution reaction, with a scaffold molecule having two or more amino groups.

The nucleophilic substitution reactions may be performed in the presence of a base, for example where the leaving group is a conventional anionic leaving group. The present inventors have found that the yields of cyclised peptide ligands can be greatly increased by suitable choice of solvent and base for the nucleophilic substitution reaction, and furthermore that the preferred solvent and base are different from the prior art solvent and base combinations that involve only the formation of thioether linkages. In particular, the present inventors have found that improved yields are achieved when using a trialkylamine base, i.e. a base of formula $NR_1R_2R_3$, wherein $R_1$, $R_2$ and $R_3$ are independently C1-C5 alkyl groups, suitably C2-C4 alkyl groups, in particular C2-C3 alkyl groups. Especially suitable bases are triethylamine and diisopropylethylamine (DIPEA). These bases have the property of being only weakly nucleophilic, and it is thought that this property accounts for the fewer side reactions and higher yields observed with these bases. The present inventors have further found that the preferred solvents for the nucleophilic substitution reaction are polar and protic solvents, in particular MeCN/H$_2$O (50:50).

In a further aspect, the present invention provides a drug conjugate comprising the peptide ligand according to the invention conjugated to one or more effector and/or functional groups such as a cytotoxic agent or a metal chelator.

Suitably, the conjugate has the cytotoxic agent linked to the peptide ligand by a cleavable bond, such as a disulphide bond. Suitably, the cytotoxic agent is selected from DM1 or MMAE.

In embodiments, the drug conjugate has the following structure:

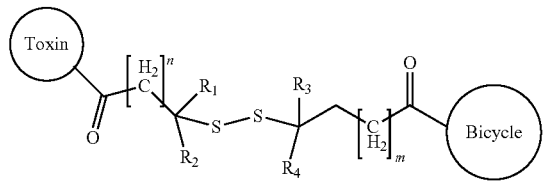

wherein: $R_1$, $R_2$, $R_3$ and $R_4$ represent hydrogen or C1-C6 alkyl groups;

Toxin refers to any suitable cytotoxic agent;

Bicycle represents the looped peptide structure;

n represents an integer selected from 1 to 10; and m represents an integer selected from 0 to 10.

Suitably, either: $R_1$, $R_2$, $R_3$ and $R_4$ are all H; or $R_1$, $R_2$, $R_3$ are all H and $R_4$=methyl; or $R_1$, $R_2$=methyl and $R_3$, $R_4$=H; or $R_1$, $R_3$=methyl and $R_2$, $R_4$=H; or $R_1$, $R_2$=H and $R_3$, $R_4$=C1-C6 alkyl.

The linker between the toxin and the bicycle peptide may comprise a triazole group formed by click-reaction between an azide-functionalized toxin and an alkyne-functionalized bicycle peptide structure (or vice-versa). In other embodiments, the bicycle peptide may contain an amide linkage formed by reaction between a carboxylate-functionalized toxin and the N-terminal amino group of the bicycle peptide.

The linker between the toxin and the bicycle peptide may comprise a cathepsin-cleavable group to provide selective release of the toxin within the target cells. A suitable cathepsin-cleavable group is valine-citrulline.

The linker between the toxin and the bicycle peptide may comprise one or more spacer groups to provide the desired functionality, e.g. binding affinity or cathepsin cleavability, to the conjugate. A suitable spacer group is para-amino benzyl carbamate (PABC) which may be located intermediate the valine-citrulline group and the toxin moiety. PABC is a so-called self-immolating group that spontaneously breaks away from the toxin after cleavage of the cleavable group.

Thus, in embodiments, the bicycle peptide-drug conjugate may have the following structure made up of Toxin-PABC-cit-val-triazole-Bicycle:

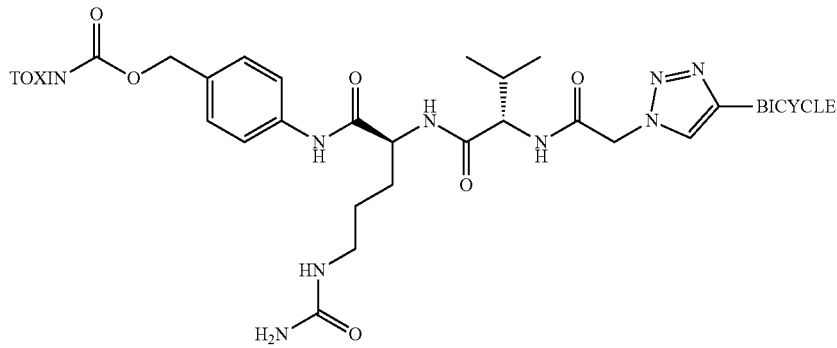

In further embodiments, the bicycle peptide-drug conjugate may have the following structure made up of Toxin-PABC-cit-val-dicarboxylate-Bicycle:

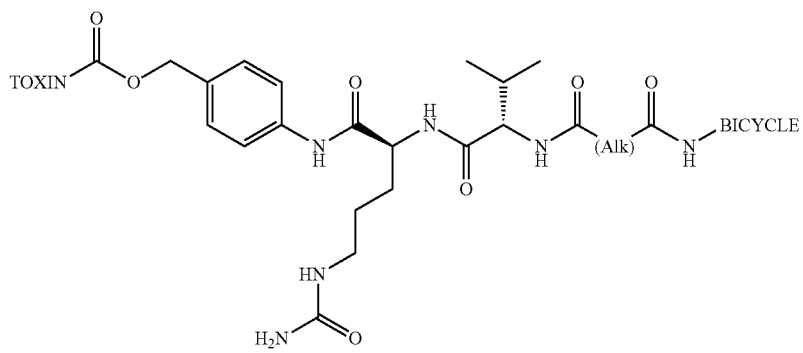

Wherein (alk) is an alkylene group of formula $C_nH_{2n}$ wherein n is from 1 to 10 and may be linear or branched, suitably (alk) is n-propylene or n-butylene.

In another aspect, the invention further provides a kit comprising at least a peptide ligand or conjugate according to the present invention.

In a still further aspect, the present invention provides a composition comprising a peptide ligand or conjugate of the present invention, and a pharmaceutically acceptable carrier, diluent or excipient.

Moreover, the present invention provides a method for the treatment of disease using a peptide ligand, conjugate, or a composition according to the present invention. Suitably, the disease is a neoplastic disease, such as cancer.

In a further aspect, the present invention provides a method for the diagnosis, including diagnosis of disease using a peptide ligand, or a composition according to the present invention. Thus in general the binding of an analyte to a peptide ligand may be exploited to displace an agent, which leads to the generation of a signal on displacement. For example, binding of analyte (second target) can displace an enzyme (first target) bound to the peptide ligand providing the basis for a binding assay, especially if the enzyme is held to the peptide ligand through its active site.

DETAILED DESCRIPTION OF THE INVENTION

Figure 1:
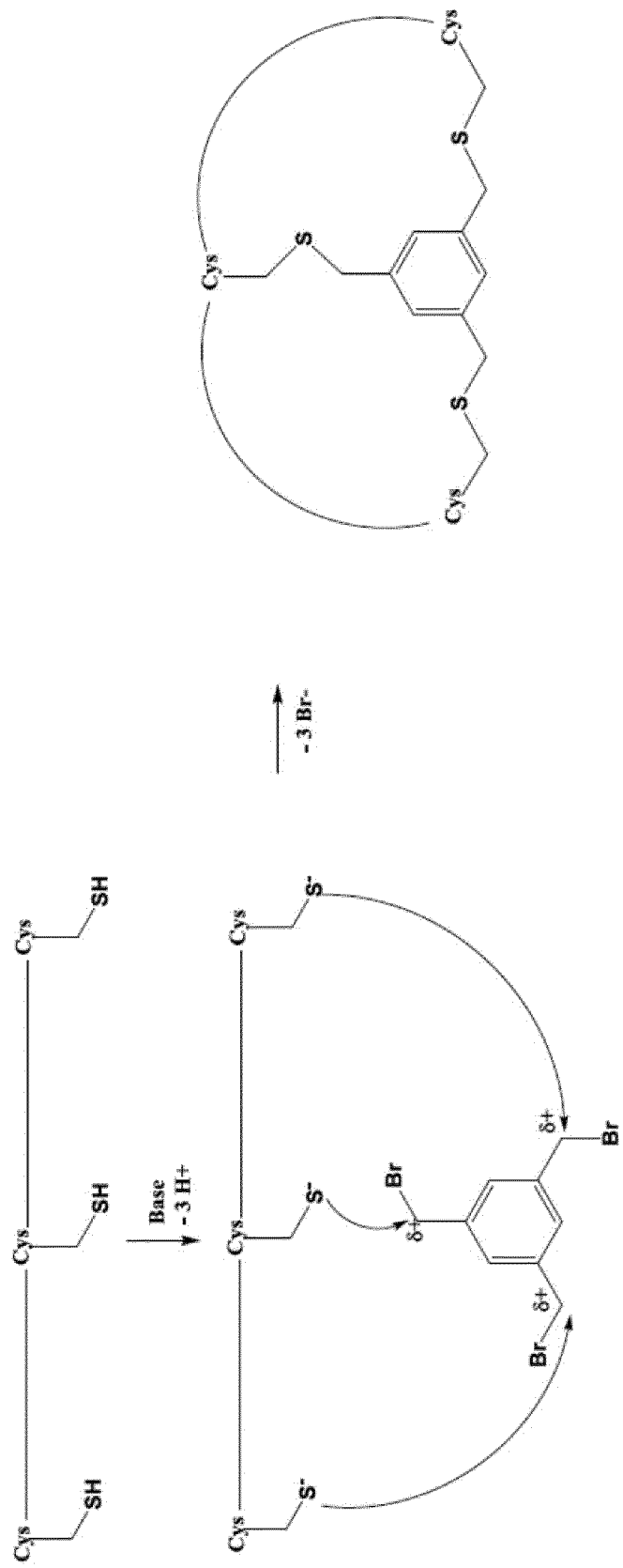
FIG. 1 shows a reaction scheme for preparation of thio-ether-linked bicyclic peptide ligands according to the prior art.

Unless defined otherwise, all technical and scientific terms used herein have the same meaning as commonly understood by those of ordinary skill in the art, such as in the arts of peptide chemistry, cell culture and phage display, nucleic acid chemistry and biochemistry.

Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4th ed., John Wiley & Sons, Inc.), which are incorporated herein by reference.

The present invention provides a looped peptide structure as defined in claim 1 comprising two peptide loops subtended between three linkages on the molecular scaffold, the central linkage being common to the two loops. The central linkage may be a thioether linkage formed to a cysteine residue of the peptide, or it is an alkylamino linkage formed to a Dap or N-AlkDap or N-HalkDap residue of the peptide. The two outer linkages are suitably alkylamino linkages formed to Dap or N-AlkDap or N-HalkDap residues of the peptide, or one of the outer linkages may be a thioether linkage formed to a cysteine residue of the peptide.

In one embodiment, the peptide ligands of the invention are fully cross-reactive with murine, dog, cynomolgus and human EphA2. In a yet further embodiment, the peptide ligands of the invention are selective for EphA2, but do not cross-react with EphA1, EphA3 or EphA4.

Suitably the binding affinity $k_i$ for EphA2 is less than about 500 nM, less than about 100 nM, less than about 50 nM, less than about 25 nM, or less than about 10 nM. Suitably, the binding affinity ki with EphA1, EphA3 and/or EphA4 is greater than about 500 nM, greater than about 1000 nM, or greater than about 10000 nM.

The amino acid sequences of specific peptide ligands according to the present invention are defined in the accompanying claims.

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyn-group bearing amino acids that allow functionalisation with alkyn or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In an embodiment, the N-terminal modification comprises the addition of a molecular spacer group which facilitates the conjugation of effector groups and retention of potency of the bicyclic peptide to its target. The spacer group is suitably an oligopeptide group containing from about 5 to about 30 amino acids, such as an Ala, G-Sar10-A (SEQ ID NO: 1) or bAla-Sar10-A (SEQ ID NO: 2) group. In one embodiment, the spacer group is selected from bAla-Sar10-A (SEQ ID NO: 2).

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, C☐-disubstituted derivatives (for example, aminoisobutyric acid, Aib), and cyclo amino acids, a simple derivative being amino-cyclopropylcarboxylic acid.

In a further embodiment, the non-natural amino acid residuesare selected from: 1-naphthylalanine; 2-naphthylalanine; cyclohexylglycine, phenylglycine; tert-butylglycine; 3,4-dichlorophenylalanine; cyclohexylalanine; and homophenylalanine.

In a yet further embodiment, the non-natural amino acid residues are selected from: 1-naphthylalanine; 2-naphthylalanine; and 3,4-dichlorophenylalanine. These substitutions enhance the affinity compared to the unmodified wildtype sequence.

In a yet further embodiment, the non-natural amino acid residues are selected from: 1-naphthylalanine. This substitution provided the greatest level of enhancement of affinity (greater than 7 fold) compared to wildtype.

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise ☐-turn conformations (Tugyi et al (2005) PNAS, 102(2), 413-418).

In all of the peptide sequences defined herein, one or more tyrosine residues may be replaced by phenylalanine. This has been found to improve the yield of the bicycle peptide product during base-catalyzed coupling of the peptide to the scaffold molecule.

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

The present invention includes all pharmaceutically acceptable (radio)isotope-labeled compounds of the invention, i.e. compounds of formula (II), wherein one or more atoms are replaced by atoms having the same atomic number, but an atomic mass or mass number different from the atomic mass or mass number usually found in nature, and compounds of formula (I1), wherein metal chelating groups are attached (termed "effector") that are capable of holding relevant (radio)isotopes, and compounds of formula (1), wherein certain functional groups are covalently replaced with relevant (radio)isotopes or isotopically labelled functional groups.

Examples of isotopes suitable for inclusion in the compounds of the invention comprise isotopes of hydrogen, such as $^2$H (D) and $^3$H (T), carbon, such as IT, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulfur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled compounds of formula (II), for example, those incorporating a radioactive isotope, are useful in drug and/or substrate tissue distribution studies, and to clinically assess the presence and/or absence of the EphA2 target on diseased tissues such as tumours and elsewhere. The compounds of formula (II) can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. 2H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Incorporation of isotopes into metal chelating effector groups, such as $^{64}$Cu, $^{67}$Ga, $^{68}$Ga, and $^{177}$Lu can be useful for visualizing tumour specific antigens employing PET or SPECT imaging.

Incorporation of isotopes into metal chelating effector groups, such as, but not limited to $^{90}$Y, $^{177}$Lu, and $^{213}$Bi, can present the option of targeted radiotherapy, whereby metal-chelator-bearing compounds of formula (II) carry the therapeutic radionuclide towards the target protein and site of action.

Isotopically-labeled compounds of formula (II) can generally be prepared by conventional techniques known to those skilled in the art or by processes analogous to those described in the accompanying Examples using an appropriate isotopically-labeled reagent in place of the non-labeled reagent previously employed.

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands can be capable of binding to two or more targets and are therefore multispecific. Suitably, they bind to two targets, and are dual specific. The binding may be independent, which would mean that the binding sites for the targets on the peptide are not structurally hindered by the binding of one or other of the targets. In this case, both targets can be bound independently. More generally, it is expected that the binding of one target will at least partially impede the binding of the other.

There is a fundamental difference between a dual specific ligand and a ligand with specificity which encompasses two related targets. In the first case, the ligand is specific for both targets individually, and interacts with each in a specific manner. For example, a first loop in the ligand may bind to a first target, and a second loop to a second target. In the second case, the ligand is non-specific because it does not differentiate between the two targets, for example by interacting with an epitope of the targets which is common to both.

In the context of the present invention, it is possible that a ligand which has activity in respect of, for example, a target and an orthologue, could be a bispecific ligand. However, in one embodiment the ligand is not bispecific, but has a less precise specificity such that it binds both the target and one or more orthologues. In general, a ligand which has not been selected against both a target and its orthologue is less likely to be bispecific due to the absence of selective pressure towards bispecificity. The loop length in the bicyclic peptide may be decisive in providing a tailored binding surface such that good target and orthologue cross-reactivity can be obtained, while maintaining high selectivity towards less related homologues.

If the ligands are truly bispecific, in one embodiment at least one of the target specificities of the ligands will be common amongst the ligands selected, and the level of that specificity can be modulated by the methods disclosed herein. Second or further specificities need not be shared, and need not be the subject of the procedures set forth herein.

The peptide ligand compounds of the invention comprise, consist essentially of, or consist of, the peptide covalently bound to a molecular scaffold. The term "scaffold" or "molecular scaffold" herein refers to a chemical moiety that is bonded to the peptide at the alkylamino linkages and thioether linkage (when cysteine is present) in the compounds of the invention. The term "scaffold molecule" or "molecular scaffold molecule" herein refers to a molecule that is capable of being reacted with a peptide or peptide ligand to form the derivatives of the invention having alkylamino and, in certain embodiments, also thioether bonds. Thus, the scaffold molecule has the same structure as the scaffold moiety except that respective reactive groups (such as leaving groups) of the molecule are replaced by alkylamino and thioether bonds to the peptide in the scaffold moiety.

In embodiments, the scaffold is an aromatic molecular scaffold, i.e. a scaffold comprising a (hetero)aryl group. As used herein, "(hetero)aryl" is meant to include aromatic rings, for example, aromatic rings having from 4 to 12 members, such as phenyl rings. These aromatic rings can optionally contain one or more heteroatoms (e.g., one or more of N, O, S, and P), such as thienyl rings, pyridyl rings, and furanyl rings. The aromatic rings can be optionally substituted. "(hetero)aryl" is also meant to include aromatic rings to which are fused one or more other aryl rings or non-aryl rings. For example, naphthyl groups, indole groups, thienothienyl groups, dithienothienyl, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), hydroxy groups, aldehyde groups, nitro groups, amine groups (e.g., unsubstituted, or mono- or di-substituted with aryl or alkyl groups), carboxylic acid groups, carboxylic acid derivatives (e.g., carboxylic acid esters, amides, etc.), halogen atoms (e.g., Cl, Br, and I), and the like.

Suitably, the scaffold comprises a tris-substituted (hetero)aromatic or (hetero)alicyclic moiety, for example a tris-methylene substituted (hetero)aromatic or (hetero)alicyclic moiety. The (hetero)aromatic or (hetero)alicyclic moiety is suitably a six-membered ring structure, preferably tris-substituted such that the scaffold has a 3-fold symmetry axis.

In embodiments, the scaffold is a tris-methylene (hetero) aryl moiety, for example a 1,3,5-tris methylene benzene moiety. In these embodiments, the corresponding scaffold molecule suitably has a leaving group on the methylene carbons. The methylene group then forms the $R_1$ moiety of the alkylamino linkage as defined herein. In these methylene-substituted (hetero)aromatic compounds, the electrons of the aromatic ring can stabilize the transition state during nucleophilic substitution. Thus, for example, benzyl halides are 100-1000 times more reactive towards nucleophilic substitution than alkyl halides that are not connected to a (hetero)aromatic group.

In these embodiments, the scaffold and scaffold molecule have the general formula:

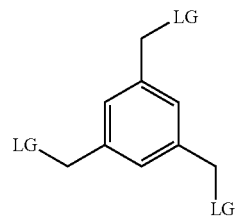

Where LG represents a leaving group as described further below for the scaffold molecule, or LG (including the adjacent methylene group forming the $R_1$ moiety of the alkylamino group) represents the alkylamino linkage to the peptide in the conjugates of the invention.

In embodiments, the group LG above may be a halogen such as, but not limited to, a bromine atom, in which case the scaffold molecule is 1,3,5-Tris(bromomethyl)benzene (TBMB). Another suitable molecular scaffold molecule is 2,4,6-tris(bromomethyl) mesitylene. It is similar to 1,3,5-tris(bromomethyl) benzene but contains additionally three methyl groups attached to the benzene ring. In the case of this scaffold, the additional methyl groups may form further contacts with the peptide and hence add additional structural constraint. Thus, a different diversity range is achieved than with 1,3,5-Tris(bromomethyl)benzene.

Another preferred molecule for forming the scaffold for reaction with the peptide by nucleophilic substitution is 1,3,5-tris(bromoacetamido)benzene (TBAB):

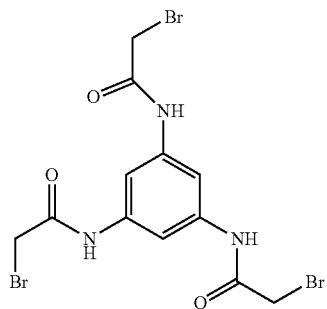 [SMILES: O=C(CBr)Nc1cc(NC(=O)CBr)cc(NC(=O)CBr)c1]

In other embodiments, the scaffold is a non-aromatic molecular scaffold, e.g. a scaffold comprising a (hetero) alicyclic group. As used herein, "(hetero)alicyclic" refers to a homocyclic or heterocyclic saturated ring. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems. In these embodiments, the alicyclic scaffold is preferably 1,1',1"-(1,3,5-tri azinane-1,3,5-triyOtriprop-2-en-1-one (TATA).

In other embodiments the molecular scaffold may have a tetrahedral geometry such that reaction of four functional groups of the encoded peptide with the molecular scaffold generates not more than two product isomers. Other geometries are also possible; indeed, an almost infinite number of scaffold geometries is possible, leading to greater possibilities for peptide ligand diversification.

The peptides used to form the ligands of the invention comprise Dap or N-AlkDap or N-HAlkDap residues for forming alkylamino linkages to the scaffold. The structure of diaminopropionic acid is analogous to and isosteric that of cysteine that has been used to form thioether bonds to the scaffold in the prior art, with replacement of the terminal —SH group of cysteine by —NH$_2$:

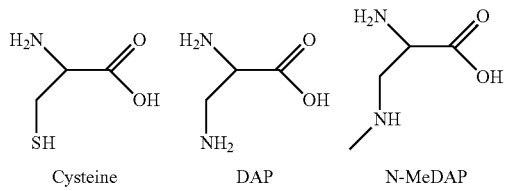

Cysteine    DAP    N-MeDAP

The term "alkylamino" is used herein in its normal chemical sense to denote a linkage consisting of NH or N(R$_3$) bonded to two carbon atoms, wherein the carbon atoms are independently selected from alkyl, alkylene, or aryl carbon atoms and R$_3$ is an alkyl group. Suitably, the alkylamino linkages of the invention comprise an NH moiety bonded to two saturated carbon atoms, most suitably methylene (—CH$_2$—) carbon atoms. The alkylamino linkages of the invention have general formula:

S—R$_1$—N(R$_3$)—R$_2$—P

Wherein:
S represents the scaffold core, e.g. a (hetero)aromatic or (hetero)alicyclic ring as explained further below;
R$_1$ is C1 to C3 alkylene groups, suitably methylene or ethylene groups, and most suitably methylene (CH$_2$);
R$_2$ is the methylene group of the Dap or N-AlkDap side chain
R$_3$ is H or C1-4 alkyl including branched alkyl and cycloalkyl, for example methyl, wherein any of the alkyl groups is optionally halogenated; and
P represents the peptide backbone, i.e. the R$_2$ moiety of the above linkage is linked to the carbon atom in the peptide backbone adjacent to a carboxylic carbon of the Dap or N-AlkDap or N-HAlkDap residue.

Certain bicyclic peptide ligands of the present invention have a number of advantageous properties which enable them to be considered as suitable drug-like molecules for injection, inhalation, nasal, ocular, oral or topical administration. Such advantageous properties include:
Species cross-reactivity. This is a typical requirement for preclinical pharmacodynamics and pharmacokinetic evaluation;
Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;
Desirable solubility profile. This is a function of the proportion of charged and hydrophilic versus hydrophobic residues and intra/inter-molecular H-bonding, which is important for formulation and absorption purposes; and
An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent.

It will be appreciated that salt forms are within the scope of this invention, and references to peptide ligands of the present invention include the salt forms of said compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzene sulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydroiodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the present invention contain an amine function, these may form quaternary ammonium salts, for example by reaction with an alkylating agent according to methods well known to the skilled person. Such quaternary ammonium compounds are within the scope of the invention.

Several conjugated peptides may be incorporated together into the same molecule according to the present invention. For example two such peptide conjugates of the same specificity can be linked together via the molecular scaffold, increasing the avidity of the derivative for its targets. Alternatively, in another embodiment a plurality of peptide conjugates are combined to form a multimer. For example, two different peptide conjugates are combined to create a multispecific molecule. Alternatively, three or more peptide conjugates, which may be the same or different, can be combined to form multispecific derivatives. In one embodiment multivalent complexes may be constructed by linking together the molecular scaffolds, which may be the same or different.

The peptide ligands of the present invention may be made by a method comprising: providing a suitable peptide and a scaffold molecule; and forming the thioether (when cysteine is present) and alkylamino linkages between the peptide and the scaffold molecule.

The peptides for preparation of the peptide ligands of the invention can be made using conventional solid-phase synthesis from amino acid starting materials, which may include appropriate protecting groups as described herein. These methods for making peptides are well known in the art.

Suitably, the peptide has protecting groups on nucleophilic groups other than the —SH and amine groups intended for forming the alkylamino linkages. The nucleophilicity of amino acid side chains has been subject to several studies, and listed in descending order: thiolate in cysteines, amines in Lysine, secondary amine in Histidine and Tryptophan, guanidino amines in Arginine, hydroxyls in Serine/Threonine, and finally carboxylates in aspartate and glutamate. Accordingly, in some cases it may be necessary to apply protecting groups to the more nucleophilic groups on the peptide to prevent undesired side reactions with these groups.

In embodiments, the method comprises: synthesising a peptide having protecting groups on nucleophilic groups other than the amine groups intended for forming the alkylamino linkages and second protecting groups on the amine groups intended for forming alkylamino linkages, wherein the protecting groups on the amine groups intended for forming alkylamino linkages can be removed under conditions different than for the protecting groups on the other nucleophilic groups, followed by treating the peptide under conditions selected to deprotect the amine groups intended for forming alkylamino linkages without deprotecting the other nucleophilic groups. The coupling reaction to the scaffold is then performed, followed by removal of the remaining protecting groups to yield the peptide conjugate.

Suitably, the method comprises reacting, in a nucleophilic substitution reaction, the peptide having the reactive side chain —SH and amine groups, with a scaffold molecule having three or more leaving groups.

The term "leaving group" herein is used in its normal chemical sense to mean a moiety capable of nucleophilic displacement by an amine group. Any such leaving group can be used here provided it is readily removed by nucleophilic displacement by amine. Suitable leaving groups are conjugate bases of acids having a pKa of less than about 5. Non-limiting examples of leaving groups useful in the invention include halo, such as bromo, chloro, iodo, O-tosylate (OTos), O-mesylate (OMes), O-triflate (OTO or O-trimethylsilyl (OTMS).

The nucleophilic substitution reactions may be performed in the presence of a base, for example where the leaving group is a conventional anionic leaving group. The present inventors have found that the yields of cyclised peptide ligands can be greatly increased by suitable choice of solvent and base (and pH) for the nucleophilic substitution reaction, and furthermore that the preferred solvent and base are different from the prior art solvent and base combinations that involve only the formation of thioether linkages. In particular, the present inventors have found that improved yields are achieved when using a trialkylamine base, i.e. a base of formula $NR_1R_2R_3$, wherein $R_1$, $R_2$ and $R_3$ are independently C1-C5 alkyl groups, suitably C2-C4 alkyl groups, in particular C2-C3 alkyl groups. Especially suitable bases are triethylamine and diisopropylethylamine (DIPEA). These bases have the property of being only weakly nucleophilic, and it is thought that this property accounts for the fewer side reactions and higher yields observed with these bases. The present inventors have further found that the preferred solvents for the nucleophilic substitution reaction are polar and protic solvents, in particular MeCN/$H_2O$ containing MeCN and $H_2O$ in volumetric ratios from 1:10 to 10:1, suitably from 2:10 to 10:2 and more suitably from 3:10 to 10:3, in particular from 4:10 to 10:4.

Additional binding or functional activities may be attached to the N or C terminus of the peptide covalently linked to a molecular scaffold. The functional group is, for example, selected from the group consisting of: a group capable of binding to a molecule which extends the half-life of the peptide ligand in vivo, and a molecule which extends the half-life of the peptide ligand in vivo. Such a molecule can be, for instance, HSA or a cell matrix protein, and the group capable of binding to a molecule which extends the half-life of the peptide ligand in vivo is an antibody or antibody fragment specific for HSA or a cell matrix protein. Such a molecule may also be a conjugate with high molecular weight PEGs.

In one embodiment, the functional group is a binding molecule, selected from the group consisting of a second peptide ligand comprising a peptide covalently linked to a molecular scaffold, and an antibody or antibody fragment. 2, 3, 4, 5 or more peptide ligands may be joined together. The specificities of any two or more of these derivatives may be the same or different; if they are the same, a multivalent binding structure will be formed, which has increased avidity for the target compared to univalent binding molecules.

The molecular scaffolds, moreover, may be the same or different, and may subtend the same or different numbers of loops.

The functional group can moreover be an effector group, for example an antibody Fc region.

Attachments to the N or C terminus may be made prior to binding of the peptide to a molecular scaffold, or afterwards. Thus, the peptide may be produced (synthetically, or by biologically derived expression systems) with an N or C terminal peptide group already in place. Preferably, however, the addition to the N or C terminus takes place after the peptide has been combined with the molecular backbone to form a conjugate. For example, Fluorenylmethyloxycarbonyl chloride can be used to introduce the Fmoc protective group at the N-terminus of the peptide. Fmoc binds to serum albumins including HSA with high affinity, and Fmoc-Trp or Fmoc-Lys bind with an increased affinity. The peptide can be synthesised with the Fmoc protecting group left on, and then coupled with the scaffold through the alkylaminos. An alternative is the palmitoyl moiety which also binds HSA and has, for example been used in Liraglutide to extend the half-life of this GLP-1 analogue.

Alternatively, a conjugate of the peptide with the scaffold can be made, and then modified at the N-terminus, for example with the amine- and sulfhydryl-reactive linker N-e-maleimidocaproyloxy) succinimide ester (EMCS). Via this linker the peptide conjugate can be linked to other peptides, for example an antibody Fc fragment.

The binding function may be another peptide bound to a molecular scaffold, creating a multimer; another binding protein, including an antibody or antibody fragment; or any other desired entity, including serum albumin or an effector group, such as an antibody Fc region.

Additional binding or functional activities can moreover be bound directly to the molecular scaffold.

In embodiments, the scaffold may further comprise a reactive group to which the additional activities can be bound. Preferably, this group is orthogonal with respect to the other reactive groups on the molecular scaffold, to avoid interaction with the peptide. In one embodiment, the reactive group may be protected, and deprotected when necessary to conjugate the additional activities.

Accordingly, in a further aspect of the invention, there is provided a drug conjugate comprising a peptide ligand as defined herein conjugated to one or more effector and/or functional groups.

Effector and/or functional groups can be attached, for example, to the N or C termini of the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of *Drosophila* (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from *Drosophila* Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

RGD peptides, which bind to integrins which are present on many cells, may also be incorporated.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half life in the range 12 to 60 hours. In a further embodiment, it will have a tβ half-life of a day or more. In a further embodiment still, it will be in the range 12 to 26 hours.

In one particular embodiment of the invention, the functional group conjugated to the looped peptide is selected from a metal chelator, which is suitable for complexing metal radioisotopes of medicinal relevance. Such effectors, when complexed with said radioisotopes, can present useful agents for cancer therapy. Suitable examples include DOTA, NOTA, EDTA, DTPA, HEHA, SarAr and others (Targeted Radionuclide therapy, Tod Speer, Wolters/Kluver Lippincott Williams & Wilkins, 2011).

Possible effector groups also include enzymes, for instance such as carboxypeptidase G2 for use in enzyme/prodrug therapy, where the peptide ligand replaces antibodies in ADEPT.

In one particular embodiment of this aspect of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin and others.

In one further particular embodiment of the invention according to this aspect, the cytotoxic agent is selected from DM1 or MMAE.

DM1 is a cytotoxic agent which is a thiol-containing derivative of maytansine and has the following structure:

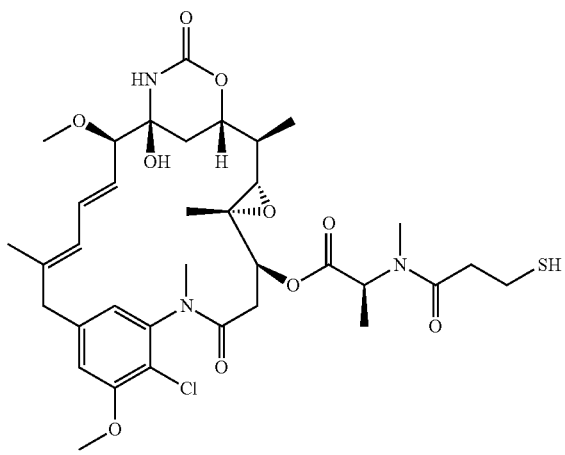

Monomethyl auristatin E (MMAE) is a synthetic antineoplastic agent and has the following structure:

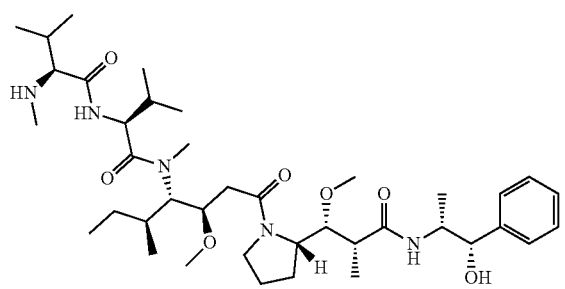 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

In one embodiment, the cytotoxic agent is linked to the bicyclic peptide by a cleavable bond, such as a disulphide bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

Thus, in one embodiment, the cytotoxic agent is selected from a compound of formula:

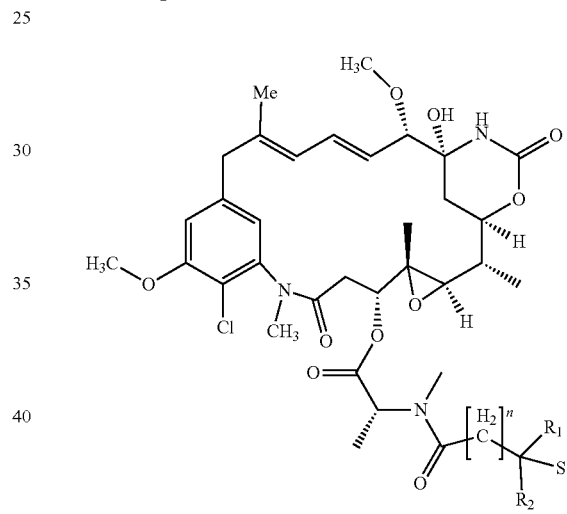

wherein n represents an integer selected from 1 to 10; and $R_1$ and $R_2$ independently represent hydrogen or methyl groups.

In one embodiment of the compound of the above formula, n represents 1 and $R_1$ and $R_2$ both represent hydrogen (i.e. the maytansine derivative DM1).

In an alternative embodiment of the compound of the above formula, n represents 2, $R_1$ represents hydrogen and $R_2$ represents a methyl group (i.e. the maytansine derivative DM3).

In one embodiment of the compound, n represents 2 and $R_1$ and $R_2$ both represent methyl groups (i.e. the maytansine derivative DM4).

It will be appreciated that the cytotoxic agent can form a disulphide bond, and in a conjugate structure with a bicyclic peptide, the disulphide connectivity between the thiol-toxin and thiol-bicycle peptide is introduced through several possible synthetic schemes.

In one embodiment, the bicyclic peptide component of the conjugate has the following structure:

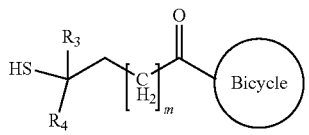

wherein m represents an integer selected from 0 to 10,

Bicycle represents any suitable looped peptide structure as described herein; and $R_3$ and $R_4$ independently represent hydrogen or methyl.

Compounds of the above formula where $R_3$ and $R_4$ are both hydrogen are considered unhindered and compounds of the above formula where one or all of $R_3$ and $R_4$ represent methyl are considered hindered.

It will be appreciated that the bicyclic peptide of the above formula can form a disulphide bond, and in a conjugate structure with a cytotoxic agent described above, the disulphide connectivity between the thiol-toxin and thiol-bicycle peptide is introduced through several possible synthetic schemes.

In one embodiment, the cytotoxic agent is linked to the bicyclic peptide by the following linker:

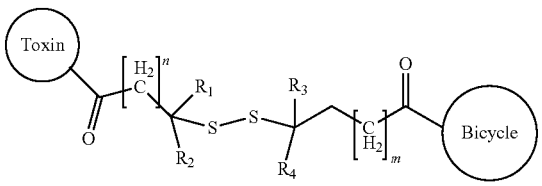

wherein $R_1$, $R_2$, $R_3$ and $R_4$ represent hydrogen or C1-C6 alkyl groups;

Toxin refers to any suitable cytotoxic agent defined herein;

Bicycle represents any suitable looped peptide structure as described herein;

n represents an integer selected from 1 to 10; and m represents an integer selected from 0 to 10.

When $R_1$, $R_2$, $R_3$ and $R_4$ are each hydrogen, the disulphide bond is least hindered and most susceptible to reduction. When $R_1$, $R_2$, $R_3$ and $R_4$ are each alkyl, the disulphide bond is most hindered and least susceptible to reduction. Partial substitutions of hydrogen and alkyl yield a gradual increase in resistance to reduction, and concomitant cleavage and release of toxin. Preferred embodiments include: $R_1$, $R_2$, $R_3$ and $R_4$ all H; $R_1$, $R_2$, $R_3$ all H and $R_4$=methyl; $R_1$, $R_2$=methyl and $R_3$, $R_4$=H; $R_1$, $R_3$=methyl and $R_2$, $R_4$=H; and $R_1$, $R_2$=H, $R_3$, $R_4$=C1-C6 alkyl.

In one embodiment, the toxin of compound is a maytansine and the conjugate comprises a compound of the following formula:

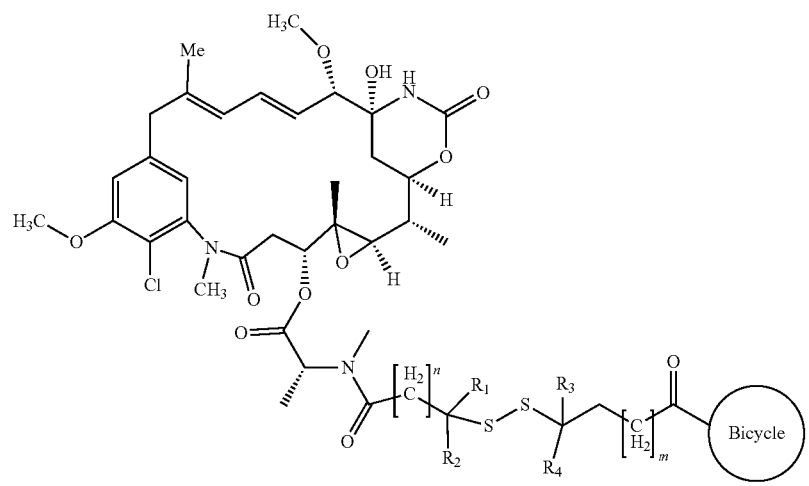

wherein $R_1$, $R_2$, $R_3$ and $R_4$ are as defined above;

Bicycle represents any suitable looped peptide structure as defined herein;

n represents an integer selected from 1 to 10; and m represents an integer selected from 0 to 10.

Further details and methods of preparing the above-described conjugates of bicycle peptide ligands with toxins are described in detail in our published patent applications WO2016/067035 and WO2017/191460. The entire disclosure of these applications is expressly incorporated herein by reference.

The linker between the toxin and the bicycle peptide may comprise a triazole group formed by click-reaction between an azide-functionalized toxin and an alkyne-functionalized bicycle peptide structure (or vice-versa). In other embodiments, the bicycle peptide may contain an amide linkage formed by reaction between a carboxylate-functionalized toxin and the N-terminal amino group of the bicycle peptide.

The linker between the toxin and the bicycle peptide may comprise a cathepsin-cleavable group to provide selective release of the toxin within the target cells. A suitable cathepsin-cleavable group is valine-citrulline.

The linker between the toxin and the bicycle peptide may comprise one or more spacer groups to provide the desired functionality, e.g. binding affinity or cathepsin cleavability, to the conjugate. A suitable spacer group is para-amino benzyl carbamate (PABC) which may be located intermediate the valine-citrulline group and the toxin moiety.

Thus, in embodiments, the bicycle peptide-drug conjugate may have the following structure made up of Toxin-PABC-cit-val-triazole-Bicycle:

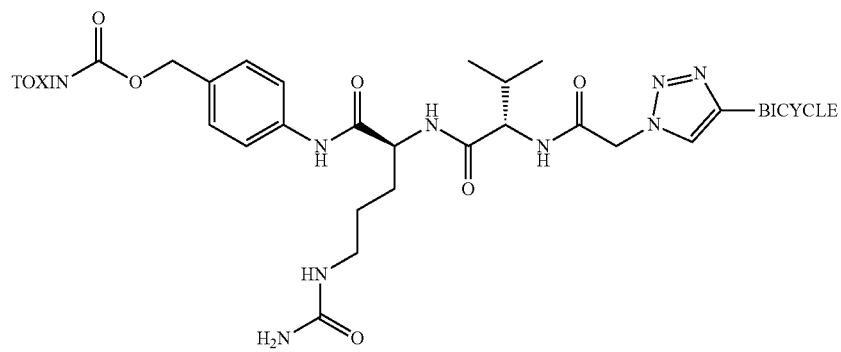

In further embodiments, the bicycle peptide-drug conjugate may have the following structure made up of Toxin-PABC-cit-val-dicarboxylate-Bicycle:

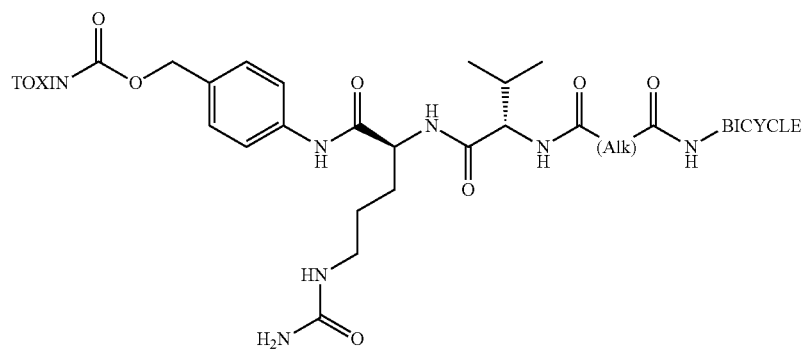

wherein (alk) is an alkylene group of formula $C_nH_{2n}$ wherein n is from 1 to 10 and may be linear or branched, suitably (alk) is n-propylene or n-butylene.

A detailed description of methods for the preparation of peptide ligand-drug conjugates according to the present invention is given in our earlier applications WO2016/067035 and PCT/EP2017/083954 filed 20 Dec. 2017, the entire contents of which are incorporated herein by reference.

Peptide ligands according to the present invention may be employed in in vivo therapeutic and prophylactic applications, in vitro and in vivo diagnostic applications, in vitro assay and reagent applications, and the like.

In general, the use of a peptide ligand can replace that of an antibody. Derivatives selected according to the invention are of use diagnostically in Western analysis and in situ protein detection by standard immunohistochemical procedures; for use in these applications, the derivatives of a selected repertoire may be labelled in accordance with techniques known in the art. In addition, such peptide ligands may be used preparatively in affinity chromatography procedures, when complexed to a chromatographic support, such as a resin. All such techniques are well known to one of skill in the art. Peptide ligands according to the present invention possess binding capabilities similar to those of antibodies, and may replace antibodies in such assays.

Diagnostic uses include any uses which to which antibodies are normally put, including test-strip assays, laboratory assays and immunodiagnostic assays.

Therapeutic and prophylactic uses of peptide ligands prepared according to the invention involve the administration of derivatives selected according to the invention to a recipient mammal, such as a human. Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected peptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

Generally, the present peptide ligands will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a peptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum, and immunotoxins. Pharmaceutical compositions can include "cocktails" of various cytotoxic or other agents in conjunction with the selected antibodies, receptors or binding proteins thereof of the present invention, or even combinations of selected peptides according to the present invention having different specificities, such as peptides selected using different target derivatives, whether or not they are pooled prior to administration.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counter-indications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that use levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the selected repertoires of peptides described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

The invention is further described with reference to the following examples.

EXAMPLES

Materials and Methods

| Abbreviations | Name | Precursor Name | Precursor CAS | Supplier |
|---|---|---|---|---|
| 1Nal | 1-Naphthylalanine | Fmoc-3-(1-naphthyl-L-alanine | 96402-49-2 | Fluorochem |
| 2FuAla | 2-Furylalanine | Fmoc-L-2-furylalanine | 159611-02-6 | Combi Blocks |
| 2Nal | 2-Naphthylalanine | Fmoc-3-(2-naphthyl)-L-alanine | 112883-43-9 | Alfa Aesar |
| 3,3-DPA | 3,3-Diphenylalanine | fmoc-3,3-diphenylalanine | 189937-46-0 | Alfa Aesar |
| 3,4-DCPhe | 3,4-Dichlorophenyl-alanine | Fmoc-3,4-dichloro-L-phenylalanine | 17766-59-5 | Poly Peptide |
| 3Pal | 3-(3-Pyridyl)-Alanine | N-Fmoc-3-(3-pyridyl)-Lßnine | 175453-07-3 | Fluorochem |
| 4,4-BPA | 4,4'-Biphenylalanine | Fmoc-L-4, 4'-Biphenylalanine | 199110-64-0 | Alfa Aesar |
| 4BenzylPro | 4-Benzyl-pyrrolidine-2-carboxylic acid | Fmoc-4-Benzyl-pyrrolidine-2-carboxylic acid | | PolyPeptide |
| 4BrPhe | 4-Bromophenylalanine | Fmoc-4-Bromo-L-phenylalanine | 198561-04-5 | PolyPeptide |
| 4FlPro | 4-Fluoro-pyrrolidine-2-carboxylic acid | Fmoc-4-fluoro-pyrrolidine-2-carboxylic acid | 203866-19-7 | PolyPeptide |
| 4MeoPhe | 4-Methoxyphenylalanine | Fmoc-4-Methoxyphenylalanine | 77128-72-4 | Iris Biotech |
| 4Pal | 3-(4-Pyridyl)-Alanine | N-Fmoc-3-(4-pyridyl)-L-alanine | 169555-95-7 | Fluorochem |
| 4PhenylPro | 4-Phenyl-pyrrolidine-2-carboxylic acid | Fmoc-4-phenyl-pyrrolidine-2-carboxylic acid | 269078-71-9 | Cambridge Bioscience |
| Ac | Acetyl | | | |
| AC3C | 1-Aminocyclopropane-1-carboxylic acid | 1-(Fmoc-amino)cyclopropane-carboxylic acid | 126705-22-4 | Iris Biotech |

| Abbreviations | Name | Precursor Name | Precursor CAS | Supplier |
|---|---|---|---|---|
| AC4C | 1-Amino-1-cyclobutanecarboxylic acid | 1-(Fmoc-amino)-cyclobutylcarboxylic acid | 885951-77-9 | Fluorochem |
| AC5C | 1-Amino-1-cyclopentanecarboxylic acid | 1-(Fmoc-amino)cyclopentane-carboxylic acid | 117322-30-2 | Iris Biotech |
| AF488 | AlexaFluor488 | AlexaFluor488-NHS Ester | | Fisher Scientific |
| Aib | 2-Aminoisobutyric acid | Fmoc-α-aminoisobutyric acid | 94744-50-0 | Fluorochem |
| Aza-Gly | Azaglycine | | | |
| Aze | Azetidine | Fmoc-L-azetidine-2-carboxylic acid | 136552-06-2 | Combi Blocks |
| β-Ala | β-Alanine | Fmoc-β-alanine | 35737-10-1 | Fluorochem |
| C5g | Cyclopentylglycine | Fmoc-L-cyclopentylglycine | 220497-61-0 | Fluorochem |
| Cba | β-Cyclobutylalanine | Fmoc-β-cyclobutyl-L-alanine | 478183-62-9 | IRIS Biotech GmbH |
| Cpa | β-Cyclopropylalanine | Fmoc-β-cyclopropyl-L-alanine | 214750-76-2 | Fluorochem |
| Cpg | Cyclopropylglycine | Fmoc-L-cycloproprylglycine | 1212257-18-5 | Apollo Scientific |
| DOTA | 1,4,7,10-tetraazacyclododecane-1,4,7,10-tetraacetic acid | | | |
| Fl | 5(6)-carboxyfluorescein | | | Sigma |
| HArg | Homo Arginine | Fmoc-L-HomoArg(Pbf)-OH | 401915-53-5 | Fluorochem |
| HPhe | HomoPhenylalanine | Fmoc-L-Homophenylalanine | 132684-59-4 | Iris Biotech |
| HyP | Hydroxyproline | Fmoc-Hydroxyproline(tBu)-OH | 122996-47-8 | Sigma |
| NO2Phe | 4-Nitrophenylalanine | Fmoc-4-nitro-L-phenylalanine | 95753-55-2 | PolyPeptide |
| Phg | Phenylglycine | Fmoc-L-phenylglycine | 102410-65-1 | Combi Blocks |
| Pip | Pipecolic acid | Fmoc-L-Pipecolic acid | 86069-86-5 | Peptech |
| Sar | Sarcosine, such that Sar$_x$ represents x Sar residues | Fmoc-Sarcosine-OH | 77128-70-2 | Sigma |
| tBuGly | Tert-leucine | Fmoc-L-tert-leucine | 132684-60-7 | Fluorochem |
| Thi | 2-Thienylalanine | Fmoc-2-Thienylalanine | 130309-35-2 | Novabiochem |
| ThiAz | 3-(1,2,4-triazol-1-yl)-Alanine | Fmoc-3-(1,2,4-triazol-1-yl)-Ala-OH | 1217449-37-0 | Sigma |
| ΨAla | Reduced amide on backbone | | | |

In addition, the following non-natural amino acid precursors were used for the preparation of the DAP and N-MeDAP modified peptides:

| Compound | CAS | Mw | Supplier |
|---|---|---|---|
| Fmoc-L-Dap(Boc,Me)-OH | 446847-80-9 | 440.49 | Iris Biotech GMBH |
| Fmoc-Dap(Boc)-OH | 162558-25-0 | 426.46 | Sigma Aldrich |

Peptide Synthesis

Peptide synthesis was based on Fmoc chemistry, using a Symphony and SymphonyX peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology. Peptides were purified by HPLC and following isolation they were modified with 1,3,5-tris(bromomethyl)benzene (TBMB, Sigma). For this, linear peptide was diluted with H$_2$O up to ~35 mL, ~500 μL of 100 mM TBMB in acetonitrile was added, and the reaction was initiated with ~5 mL of 1 M NH$_4$HCO$_3$ in H$_2$O. The reaction was allowed to proceed for ~30 –60 min at RT, and quenched with 500 ul of the 1M Cysteine hydrochloride (Sigma) once the reaction had completed (judged by MALDI). Following lyophilisation, the modified peptide was purified in a Gemini C18 column (Phenomenex) using water/acetonitrile with 0.1% trifluoroacetic acid as mobile phase. Pure fractions containing the correct cyclised material were pooled, lyophilised and kept at −20° C. for storage.

All amino acids, unless noted otherwise, were used in the L-configurations.

Biological Data
1. Fluorescence Polarisation Measurements
(a) Direct Binding Assay Peptides with a fluorescent tag (either fluorescein, SIGMA or Alexa Fluor488™, Fisher Scientific) were diluted to 2.5 nM in PBS with 0.01% tween 20 or 50 mM HEPES with 100 mM NaCl and 0.01% tween pH 7.4 (both referred to as assay buffer). This was combined with a titration of protein in the same assay buffer as the peptide to give 1 nM peptide in a total volume of 254 in a black walled and bottomed low bind low volume 384 well plates, typically 54 assay buffer, 104 protein (Table 1) then 10 μL fluorescent peptide. One in two serial dilutions were used to give 12 different concentrations with top concentrations ranging from 500 nM for known high affinity binders to 10 μM for low affinity binders and selectivity assays. Measurements were conducted on a BMG PHERAstar FS equipped with an "FP 485 520 520" optic module which excites at 485 nm and detects parallel and perpendicular emission at 520 nm. The PHERAstar FS was set at 25° C. with 200 flashes per well and a positioning delay of 0.1 second, with each well measured at 5 to 10 minute intervals for 60 minutes. The gain used for analysis was determined for each tracer at the end of the 60 minutes where there was no protein in the well. Data was analysed using Systat Sigmaplot version 12.0. mP values were fit to a user defined quadratic equation to generate a Kd value: f=y min+(y max−y min)/Lig*((x+Lig+Kd)/2−sqrt((((x+Lig+Kd)/2)^2)−(Lig*x))). "Lig" was a defined value of the concentration of tracer used.

(b) Competition Binding Assay

Peptides without a fluorescent tag were tested in competition with a peptide with a fluorescent tag and a known Kd (Table 2). Peptides were diluted to an appropriate concentration in assay buffer as described in the direct binding assay with a maximum of 5% DMSO, then serially diluted 1 in 2. Five μL of diluted peptide was added to the plate followed by 104 of human or mouse EphA2 (Table 1) at a fixed concentration which was dependent on the fluorescent peptide used (Table 2), then 104 fluorescent peptide added. Measurements were conducted as for the direct binding assay, however the gain was determined prior to the first measurement. Data analysis was in Systat Sigmaplot version 12.0 where the mP values were fit to a user defined cubic equation to generate a Ki value:

$f$=$y$ min+($y$ max−$y$ min)/Lig*((Lig*((2*((Klig+Kcomp+Lig+Comp−Prot*$c$)^2−3*(Kcomp*(Lig−Prot*$c$)+Klig*(Comp−Prot*$c$)+Klig*Kcomp))^0.5*COS(ARCCOS((−2*(Klig+Kcomp+Lig+Comp−Prot*$c$)^3+9*(Klig+Kcomp+Lig+Comp−Prot*$c$)*(Kcomp*(Lig−Prot*$c$)+Klig*(Comp−Prot*$c$)+Klig*Kcomp))−27*(−1*Klig*Kcomp*Prot*$c$))/(2*(4*(Klig+Kcomp+Lig+Comp−Prot*$c$)^2−3*(Kcomp*(Lig−Prot*$c$)+Klig*(Comp−Prot*$c$)+Klig*Kcomp))^3)^0.5))/3))−(Klig+Kcomp+Lig+Comp−Prot*$c$))/((3*Klig)+42*((Klig+Kcomp+Lig+Comp−Prot*$c$)^2−3*(Kcomp*(Lig−Prot*$c$)+Klig*(Comp−Prot*$c$)+Klig*Kcomp))^0.5*COS(ARCCOS((−2*(Klig+Kcomp+Lig+Comp−Prot*$c$)^3+9*(Klig+Kcomp+Lig+Comp−Prot*$c$)*(Kcomp*(Lig−Prot*$c$)+Klig*(Comp−Prot*$c$)+Klig*Kcomp))−27*(−1*Klig*Kcomp*Prot*$c$))/(2*(4*(Klig+Kcomp+Lig+Comp−Prot*$c$)^2−3*(Kcomp*(Lig−Prot*$c$)+Klig*(Comp−Prot*$c$)+Klig*Kcomp))^3)^0.5))/3))−(Klig+Kcomp+Lig+Comp−Prot*$c$))).

"Lig", "KLig" and "Prot" were all defined values relating to: fluorescent peptide concentration, the Kd of the fluorescent peptide and EphA2 concentration respectively.

TABLE 1

Ephrin receptors and source

| Receptor (domain) | Species | Format/tag | Supplier | Catalogue number |
|---|---|---|---|---|
| EphA1 (Ecto) | Human | Fc fusion | R&D systems | 7146-A1 |
| EphA2 (Ecto) | Human | C-terminal polyHis | R&D systems | 3035-A2 |
| EphA2 (Ecto) | Human | C-terminal polyHis | In-house | N/A |
| EphA2 (Ecto) | Mouse | Fc fusion | R&D Systems | 639-A2 |
| EphA2 (Ecto) | Mouse | C-terminal polyHis | Sino Biological | 50586-M08H |
| EphA2 (ligand binding) | Rat | C-terminal polyHis | In-house | N/A |
| EphA2 (ligand binding) | Dog | C-terminal polyHis | In-house | N/A |
| EphA3 (Ecto) | Human | Fc fusion | R&D systems | 6444-A3 |
| EphA3 (Ecto) | Human | N-terminal polyHis | In-house | N/A |
| EphA3 (Ecto) | Rat | C-terminal polyHis | Sino Biological | 80465-R08H |
| EphA4 (Ecto) | Human | Fc fusion | R&D systems | 6827-A4 |
| EphA4 (Ecto) | Human | C-terminal polyHis | Sino Biological | 11314-H08H |
| EphA4 (Ecto) | Rat | C-terminal polyHis | Sino Biological | 80123-R08H |
| EphA6 (Ecto) | Human | Fc fusion | R&D systems | 5606-A6 |
| EphA7 (Ecto) | Human | Fc fusion | R&D systems | 6756-A7 |
| EphB1 (Ecto) | Rat | Fc fusion | R&D systems | 1596-B1 |
| EphB4 (Ecto) | human | C-terminal polyHis | R&D systems | 3038-B4 |

TABLE 2

Final concentrations of fluorescent peptide and EphA2 as used with Competition Binding Assays

| Fluorescent peptide | Concentration of fluorescent peptide (nM) | Concentration of Human EphA2 (nM) | Concentration of Mouse EphA2 (nM) |
|---|---|---|---|
| Compound 1 | 1 | 300 | |
| Compound 12 | 10 | 75 | |
| Compound 66 | 1 | 30 | |
| Compound 18 | 0.8 (human) 1 (mouse) | 2.4 | 50 |

The peptide ligands described herein were tested in the above mentioned assays.

Reference Example 1

Figure 2:
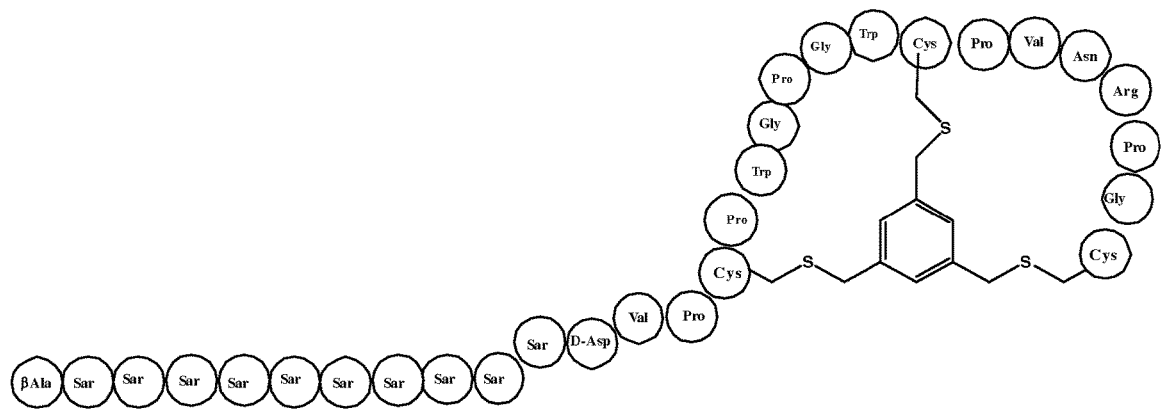
FIG. 2 shows a schematic structure of a reference bicyclic peptide ligand exhibiting specific binding to EphA2.

A first reference Bicyclic Peptide chosen for comparison of thioether to alkylamino scaffold linkage was designated 55-03-05-N233. It is a bicycle conjugate of a thioether-forming peptide with a trimethylene benzene scaffold. The structure of this bicycle derivative is shown schematically in FIG. 2. The linear peptide before conjugation has sequence:

[B-Ala][Sar]$_{10}$H[dD]VPCPWGPFWCPVNRPGC

Conjugation to 1,3,5-tris(bromomethyl)benzene (TBMB, Sigma) was carried out as follows. The linear peptide was diluted with H$_2$O up to ~35 mL, ~500 μL of 100 mM TBMB in acetonitrile was added, and the reaction was initiated with 5 mL of 1 M NH$_4$HCO$_3$ in H$_2$O. The reaction was allowed to proceed for ~30 −60 min at RT, and lyophilised once the reaction had completed (judged by MALDI). Following lyophilisation, the modified peptide was purified with a Gemini C18 column (Phenomenex), and changing the acid to 0.1% trifluoroacetic acid. Pure fractions containing the correct TMB-modified material were pooled, lyophilised and kept at −20° C. for storage.

The resulting Bicycle derivative designated 55-03-05-N233 showed high affinity to EphA2. The measured affinity (Ki) to EphA2 of the derivative was 4.12 nM.

Example 1

Figure 3:
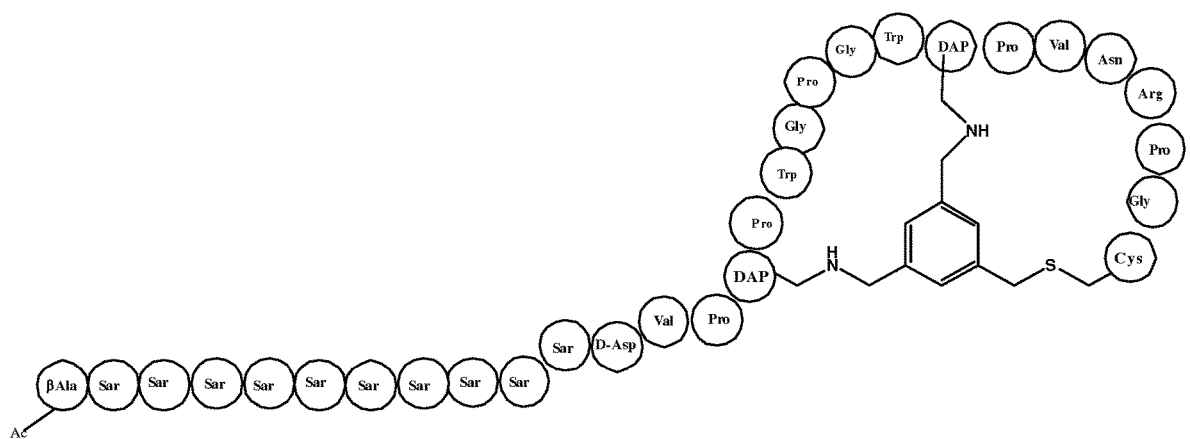
FIG. 3 shows a schematic structure of a first bicyclic peptide ligand according to the present invention.

A bicycle peptide designated 55-03-05-N314 was made corresponding to the bicycle region of the peptide ligand of Reference Example 1, with replacement of the first and second cysteine residues by DAP residues forming alkylamino linkages to the TBMB scaffold. The structure of this derivative is shown schematically in FIG. 3.

The linear peptide used to form this bicycle was as follows:

[Ac][B-Ala][Sar]$_{10}$H[dD]VP[Dap]PWGPFW[Dap]PVNRPGC

Cyclisation with TBMB was performed in a mixture of Acetonitrile/water in the presence of DIPEA as the base for 1-16 hours, as described in more detail in PCT/EP2017/083953 and PCT/EP2017/083954 filed 20 Dec. 2017. Unlike the cyclisation of Reference Example 1, the yield is relatively low when using the conventional NaHCO$_3$ as the base.

The measured Ki with EphA2 was 135.5 nM, which demonstrates that the change to alkylamino linkages in this example resulted in relatively little change in binding affinity relative to the thioether linked derivative of Reference Example 1.

Example 2

A bicycle peptide designated 55-03-05-N316 was made corresponding to the bicycle region of the peptide ligand of Reference Example 1, with replacement of the second and third cysteine residues by DAP residues forming alkylamino linkages to the TBMB scaffold. The structure of this derivative is shown schematically in FIG. 3.

The linear peptide used to form this bicycle was as follows:

[Ac][B-Ala][Sar]$_{10}$H[dD]VPCPWGPFW[Dap]PVNRPG[Dap]

Cyclisation with TBMB was performed as described in Example 1.

The measured Ki with EphA2 was 604 nM, which demonstrates that the change to alkylamino linkages in this example preserved a relatively high level of binding affinity relative to the thioether-linked derivative of Reference Example 1.

Example 3

Figure 4:
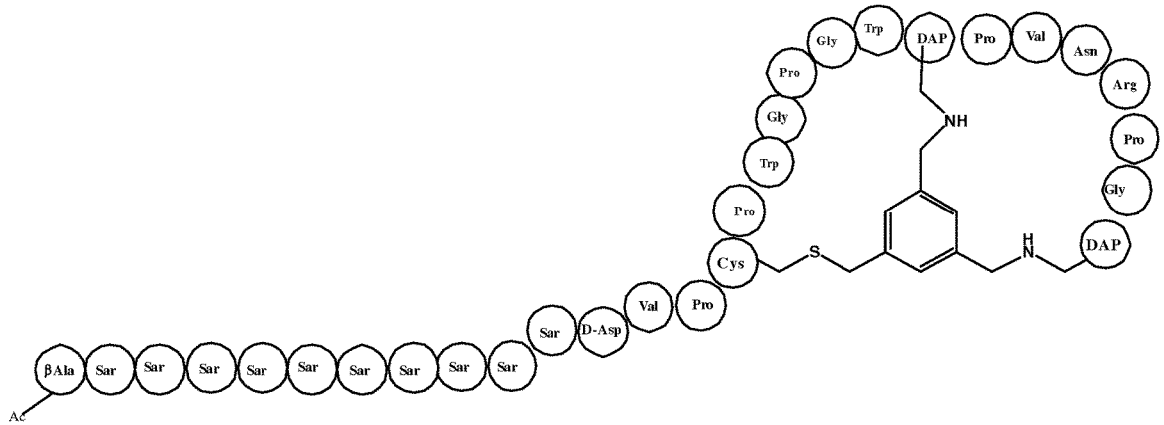
FIG. 4 shows a schematic structure of a second bicyclic peptide ligand according to the present invention.
Figure 5:
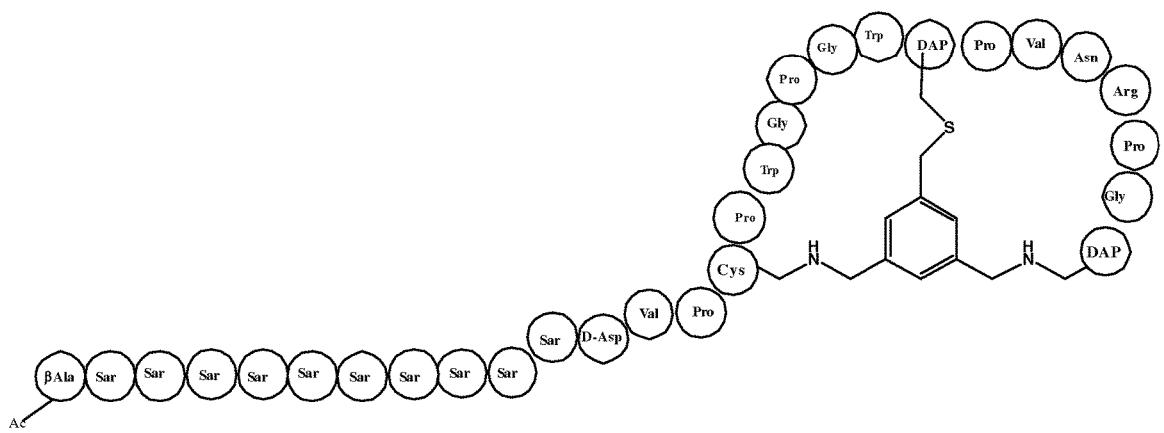
FIG. 5 shows a schematic structure of a third bicyclic peptide ligand according to the present invention.

A bicycle peptide designated 55-03-05-N318 was made corresponding to the bicycle region of the peptide ligand of Reference Example 1, with replacement of the first and third cysteine residues by DAP residues forming alkylamino linkages to the TBMB scaffold. The structure of this derivative is shown schematically in FIG. 4.

The linear peptide used to form this bicycle was as follows:

[Ac][B-Ala][Sar]$_{10}$H[dD]VP[Dap]PWGPFWCPVNRPG[Dap]

Cyclisation with TBMB was performed as described in Example 1.

The measured Ki with EphA2 was 31.5 nM, which demonstrates that the change to alkylamino linkages in this example resulted in only a minimal change in binding affinity relative to the thioether-linked derivative of Reference Example 1.

Reference Example 2

A first reference Bicyclic Peptide chosen for comparison of thioether to alkylamino scaffold linkage was designated 55-03-05-N238. It is a bicycle conjugate of a thioether-forming peptide with a trimethylene benzene scaffold. The linear peptide before conjugation has sequence:

[B-Ala][Sar]$_{10}$H[dD]VPC[Aib][1Nal]G[Aib]F [1Nal]CP[tBuGly]N[HArg]P [dD]C

Conjugation to 1,3,5-tris(bromomethyl)benzene (TBMB, Sigma) was carried out as described in Example 1.

The resulting Bicycle derivative designated 55-03-05-N238 showed high affinity to EphA2. The measured affinity (Ki) to EphA2 of the derivative was 19.7 nM.

Example 4

A bicycle peptide designated 55-03-05-N315 was made corresponding to the bicycle region of the peptide ligand of Reference Example 2, with replacement of the first and second cysteine residues by DAP residues forming alkylamino linkages to the TBMB scaffold.

The linear peptide used to form this bicycle was as follows:

[B-Ala][Sar]$_{10}$H[dD]VP[Dap][Aib][Mal]G[Aib]F[1Nal][Dap]P[tBuGly]N[HArg]P[dD]C

Cyclisation with TBMB was performed as described in Example 1.

The measured Ki with EphA2 was 640 nM, which demonstrates that the change to alkylamino linkages in this example preserved a significant binding affinity relative to the thioether-linked derivative of Reference Example 2.

Example 5

A bicycle peptide designated 55-03-05-N317 was made corresponding to the bicycle region of the peptide ligand of Reference Example 2, with replacement of the second and third cysteine residues by DAP residues forming alkylamino linkages to the TBMB scaffold.

The linear peptide used to form this bicycle was as follows:

[B-Ala][Sar]$_{10}$H[dD]VPC[Aib][Mal]G[Aib]F[1Nal][Dap]P[tBuGly]N[HArg]P[dD][Dap]

Cyclisation with TBMB was performed as described in Example 1.

The measured Ki with EphA2 was 425 nM, which demonstrates that the change to alkylamino linkages in this example preserved a significant binding affinity relative to the thioether-linked derivative of Reference Example 2.

Example 6

A bicycle peptide designated 55-03-05-N319 was made corresponding to the bicycle region of the peptide ligand of Reference Example 2, with replacement of the second and third cysteine residues by DAP residues forming alkylamino linkages to the TBMB scaffold.

The linear peptide used to form this bicycle was as follows:

[B-Ala][Sar]$_{10}$H[dD]VP [Dap][Aib][Mal]G[Aib]F [1Nal]CP [tBuGly]N[HArg]P [dD][Dap]

Cyclisation with TBMB was performed as described in Example 1.

The measured Ki with EphA2 was 17 nM, which demonstrates that the change to alkylamino linkages in this example marginally increases the affinity to EphA2 relative to the thioether-linked derivative of Reference Example 2.

Reference Examples A1-A308

The following reference peptide ligands having a TBMB scaffold with three thioether linkages to cysteine residues of the specified peptide sequences were prepared and evaluated for affinity to EphA2 as described in detail in our earlier application GB201721265.5 filed 19 Dec. 2017.

In view of the results obtained above in Examples 1-6, it is predicted that derivatives of the reference examples A1-A308 according to the present invention, i.e. having alkylamino linkages in place of one or more of the thioether linkages in the reference examples, will also display affinity for EphA2. It is further predicted that derivatives of the reference examples B1-B98 having scaffolds other than TBMB, in particular aromatic scaffolds other than TBMB, will also display affinity for EphA2. All such derivatives having affinity for EphA2 are therefore included within the scope of the present invention.

TABLE 3

Biological Assay Data for Reference Peptide Ligands (Direct Binding Assay)

| Bicycle Compound Number | Sequence | SEQ ID NO: | Scaffold | $K_D$, nM ± 95% CI Human EphA2 | Mouse EphA |
|---|---|---|---|---|---|
| 1 | ACMNDWLCSLGWTCA-Sar$_6$-K(Fl) | 3 | TBMB | 107.58 ± 40.83 | 301 n = 1 |
| 2 | AF488-G-Sar$_{10}$-ACMNDWLCSLGWTC | 4 | TBMB | 326 n = 1 | |
| 3 | ACMNDWLCELGWTCA-Sar$_6$-K(Fl) | 5 | TBMB | 121.48 ± 50.27 | |
| 4 | ACTRQGIWCALGFEPCA-Sar$_6$-K(Fl) | 6 | TBMB | 163.5 ± 22.54 | |
| 5 | ACMNDWLCTLGWSCA-Sar$_6$-K(Fl) | 7 | TBMB | 142.5 ± 83.3 | |
| 6 | ACMNDWLCQLGWTCA-Sar$_6$-K(Fl) | 8 | TBMB | 54.25 ± 4.8 | |
| 7 | ACMNDWLCTLGWTCA-Sar$_6$-K(Fl) | 9 | TBMB | 74.35 ± 15.97 | |
| 8 | ACMNDWLCDLGWRCA-Sar$_6$-K(Fl) | 10 | TBMB | 118.5 ± 22.54 | |
| 9 | ACMNDWLCELGWSCA-Sar$_6$-K(Fl) | 11 | TBMB | 137.5 ± 49.98 | |
| 10 | ACRVSPEYCPFGPVWCAGAAA-Sar$_6$-K(Fl) | 12 | TBMB | 135.13 ± 59.02 | |
| 11 | Fl-G-Sar$_5$-ACPWGPAWCPVHGKTCA | 13 | TBMB | 263 ± 213.64 | |
| 12 | Fl-G-Sar$_5$-ACPWGPAWCPVNRPGCA | 14 | TBMB | 27.78 ± 8.35 | |
| 13 | Ac-ACPWGPAWCPVNRPGCAGAAA-K(Fl) | 15 | TBMB | 29 ± 2.55 | |
| 14 | AF488-G-Sar$_{10}$-ACPWGPAWCPVNRPGCA | 16 | TBMB | 38 n = 1 | |
| 15 | Fl-G-Sar$_5$-ACPWGPMWCPVNRPGCA | 17 | TBMB | 12.6 ± 2.55 | |
| 16 | Fl-G-Sar$_5$-ACPWGPNWCPVNRPGCA | 18 | TBMB | 11.5 ± 1.76 | |
| 17 | Fl-G-Sar$_5$-AGEMACPWGPFWCPVNRPGCA | 19 | TBMB | 3.85 ± 0.1 | |
| 18 | Fl-G-Sar$_5$-ADVTCPWGPFWCPVNRPGCA | 20 | TBMB | 0.93 ± 0.23 | 4.02 ± 2 |
| 19 | Fl-G-Sar$_5$-ADVRTCPWGPFWCPVNRPGCA | 21 | TBMB | 4.74 ± 0.51 | |
| 20 | Fl-G-Sar$_5$-ANDVTCPWGPGWCPVNRPGCA | 22 | TBMB | 2.35 ± 0.49 | |
| 21 | ACVPQGIWCALQFEPCA-Sar$_6$-K(Fl) | 23 | TBMB | 59.5 ± 12.78 | |
| 22 | ACQKQGLWCALGFEPCA-Sar$_6$-K(Fl) | 24 | TBMB | 289 ± 74.51 | |
| 23 | ACLVNDDCFYMGLCA-Sar$_6$-K(Fl) | 25 | TBMB | 109.38 ± 20.75 | |

TABLE 4

Biological Assay Data for Reference Peptide Ligands (Competition Binding Assay)

| Bicycle Compound Number | Sequence | SEQ ID NO: | Scaffold | Human EphA2 ($K_i$, nM ± 95% CI) Fluorescent Peptide | | | |
|---|---|---|---|---|---|---|---|
| | | | | Compound 66 | Compound 1 | Compound 12 | Compound 18 |
| 24 | ACMNDWLCSLGWTCA | 26 | TBMB | 82.34 ± 12.8 | | | |
| 25 | Ac-CANDWLCSLGWTC | 27 | TBMB | 328 n = 1 | | | |
| 26 | Ac-CMNDWLCALGWTC | 28 | TBMB | 71.6 ± 3.33 | | | |
| 27 | Ac-CMNDWLCSAGWTC | 29 | TBMB | 356 n = 1 | | | |
| 28 | ACMNDWLCQLGWKCA | 30 | TBMB | 113 n = 1 | | | |
| 29 | ACMNDWLCELGWTCA | 31 | TBMB | 134.5 ± 32.34 | | | |
| 30 | ACMNDWLCQLGWTCA | 32 | TBMB | 56.05 ± 3.23 | | | |
| 31 | ACTQNDWLCSLGWTCA | 33 | TBMB | 151.65 ± 161.4 | | | |
| 32 | ACRNIPTMCPFGPVWCA | 34 | TBMB | | 83.4 n = 1 | | |
| 33 | ACRVSPEYCPFGPVWCA | 35 | TBMB | 78.53 ± 35.61 | | | |
| 34 | ACRVSPEYCPFGPVWCAGAAA | 36 | TBMB | 77.4 ± 8.95 | | | |
| 35 | ACRVSPEYCPFGPTWCA | 37 | TBMB | 43.2 ± 13.33 | | | |
| 36 | ACRVSPEYCPFGPSWCA | 38 | TBMB | 40.5 ± 5.88 | | | |
| 37 | ACRVSPEYCPFGPEWCA | 39 | TBMB | 61.25 ± 41.85 | | | |
| 38 | ACRVSPEYCPFGPYWCA | 40 | TBMB | 26.53 ± 16.92 | | | |
| 39 | ACRVSPEYCPFGPLWCA | 41 | TBMB | 32.11 ± 10.28 | | | |
| 40 | ACRVSPEYCPFGPDWCA | 42 | TBMB | 55.4 ± 9.41 | | | |
| 41 | ACPWGPAWCPVHGKTCA | 43 | TBMB | | 263 n = 1 | | |
| 42 | ACPWGPAWCPVRDTNCA | 44 | TBMB | 316 n = 1 | | | |
| 43 | ACPWGPAWCPVNGARCA | 45 | TBMB | 430 n = 1 | | | |
| 44 | ACPWGPAWCPVNRPGCA | 46 | TBMB | 191.22 ± 29.47 | 164 n = 1 | 128.45 ± 28.21 | |
| 45 | ACPWGPAWCPVNRPGCAGAAA | 47 | TBMB | 117.13 ± 17.96 | | 99.15 ± 48.71 | |
| 46 | ACPWGPMWCPVNRPGCA | 48 | TBMB | 95.75 ± 29.89 | | | |
| 47 | ACPWGPNWCPVNRPGCA | 49 | TBMB | 78.35 ± 12.64 | | | |
| 48 | ACPWGPAWCPVRNPCA | 50 | TBMB | 284 ± 47.04 | | | |
| 49 | ACPWGPAWCPVSRVCA | 51 | TBMB | 428 ± 99.96 | | | |
| 50 | ACPWGPAWCPVRSCA | 52 | TBMB | 314 ± 248.92 | | | |
| 51 | ACPWGPAWCPVKPTCA | 53 | TBMB | 318.5 ± 255.78 | | | |
| 52 | ACPWGPAWCPVNRNGCA | 54 | TBMB | 168 ± 72.52 | | | |
| 53 | AGEMACPWGPFWCPVNRPGCA | 55 | TBMB | 6 ± 5.54 | | | |
| 54 | AVHIPCPWGPSWCPVNRPCCA | 56 | TBMB | 5.17 ± 2.76 | | | 5.13 ± 1.52 |
| 55 | AEGLPCPWGPFWCPVNRPGCA | 57 | TBMB | 6.15 ± 3.43 | | | 11.3 ± 2.04 |
| 56 | ADHACPWGPFWCPVNRPGCA | 58 | TBMB | 5.87 ± 5.09 | | | 14.43 ± 6.28 |
| 57 | ADVHCPWGPFWCPVNRPGCA | 59 | TBMB | 1.2 n = 1 | | | 0.48 ± 0.15 |
| 58 | ADVTCPWGFFWCPVNRPGCA | 60 | TBMB | 2.65 ± 1.08 | | | 1.35 ± 0.23 |
| 59 | AHDVPCPWGPFWCPVNRPGCA | 61 | TBMB | | | | 0.54 ± 0.14 |
| 60 | ADVRTCPWGPFWCPVNRPGCA | 62 | TBMB | 2.5 n = 1 | | | 12.63 ± 1.29 |
| 61 | ANDVTCPWGPFWCPVNRPGCA | 63 | TBMB | 7.3 n = 1 | | | 2.93 ± 0.07 |
| 62 | ARDDPCPWGPFWCPVNRPGCA | 64 | TBMB | 27.96 ± 16.74 | | | 16.13 ± 0.8 |
| 63 | ACVPQGIWCALQFEPCA | 65 | TBMB | 82.45 ± 27.07 | 144 n = 1 | 92.2 ± 21.17 | |
| 64 | ACTTGSIWCALQFEPCA | 66 | TBMB | 63.4 n = 1 | | 410 n = 1 | |
| 65 | ACVPQGIWCALRYEPCA | 67 | TBMB | 293 n = 1 | | 229 n = 1 | |

TABLE 5

Biological Assay Data for Reference Peptide Ligands (Direct Binding Assay)

| Bicycle Number Compound | Sequence | SEQ ID NO: | Scaffold | $K_D$, nM ± 95% CI Human EphA2 | Mouse EphA2 |
|---|---|---|---|---|---|
| 66 | Fl-G-Sar$_5$-ACPWGPFWCPVNRPGCA | 68 | TBMB | 8.45 ± 0.4 | 22 n = 1 |
| 67 | AlexaFluor488-G-Sar$_5$-ACPWGPFWCPVNRPGC | 69 | TBMB | 15.03 ± 1.72 | 51.8 ± 6.27 |
| 68 | AlexaFluor488-(β-Ala)-Sar$_{10}$-ACPWGPFWCPVNRPGC | 70 | TBMB | 15.37 ± 2.87 | 23.4 n = 1 |

TABLE 6

Biological Assay Data for Reference Peptide Ligands (Competition Binding Assay)

| Bicycle Compound Number | Sequence | SEQ ID NO: | Scaffold | Ki, nM ± 95% CI Human EphA2 Fluorescent Peptide Compound 18 | Compound 66 |
| --- | --- | --- | --- | --- | --- |
| 69 | ACPWGPFWCPVNRPGCA | 71 | TBMB | 106.75 ± 44.25 | 70.08 ± 8.01 |
| 70 | $Sar_2$-ACPWGPFWCPVNRPGC | 72 | TBMB | 51.81 ± 21.75 | 20.45 ± 12.84 |
| 71 | Ac-$Sar_2$-ACPWGPFWCPVNRPGC | 73 | TBMB | 11.87 ± 7.51 | |
| 72 | (β-Ala)-$Sar_{10}$-ACPWGPFWCPVNRPGC | 74 | TBMB | 29.1 ± 5.08 | 20.98 ± 2.18 |
| 73 | $Sar_2$-AC(HyP)WGPFWCPVNRPGC | 75 | TBMB | 47.6 ± 18.42 | 247.5 ± 18.62 |
| 74 | $Sar_2$-AC(Aib)WGPFWCPVNRPGC | 76 | TBMB | | 138.9 ± 88.79 |
| 75 | $Sar_2$-AC(4FlPro)WGPFWCPVNRPGC | 77 | TBMB | | 399.67 ± 90.63 |
| 76 | $Sar_2$-ACP(1Nal)GPFWCPVNRPGC | 78 | TBMB | 3.5 ± 1.96 | 16.7 ± 9.68 |
| 77 | $Sar_2$-ACP(2Nal)GPFWCPVNRPGC | 79 | TBMB | | 458.33 ± 222.44 |
| 78 | $Sar_2$-ACPWG(Aze)FWCPVNRPGC | 80 | TBMB | | 403.5 ± 12.74 |
| 79 | $Sar_2$-ACPWG(HyP)FWCPVNRPGC | 81 | TBMB | | 131 ± 22.97 |
| 80 | $Sar_2$-ACPWG(Aib)FWCPVNRPGC | 82 | TBMB | 120.5 ± 81.34 | 186.73 ± 94.37 |
| 81 | $Sar_2$-ACPWG(4FlPro)FWCPVNRPGC | 83 | TBMB | | 294 ± 99.6 |
| 82 | $Sar_2$-ACPWG(Pip)FWCPVNRPGC | 84 | TBMB | | 497.33 ± 223.62 |
| 83 | $Sar_2$-ACPWGPAWCPVNRPGC | 85 | TBMB | 199 n = 1 | 287.5 ± 197.95 |
| 84 | $Sar_2$-ACPWGP(4Pal)WCPVNRPGC | 86 | TBMB | 33.5 ± 0.98 | 81.47 ± 68.95 |
| 85 | $Sar_2$-ACPWGP(4BrPhe)WCPVNRPGC | 87 | TBMB | | 174.5 ± 20.58 |
| 86 | $Sar_2$-ACPWGP(4MeoPhe)WCPVNRPGC | 88 | TBMB | | 274.5 ± 36.26 |
| 87 | $Sar_2$-ACPWGP(HPhe)WCPVNRPGC | 89 | TBMB | 162 n = 1 | 281.2 ± 154.82 |
| 88 | $Sar_2$-ACPWGP(4,4-BPA)WCPVNRPGC | 90 | TBMB | | 182.67 ± 99.5 |
| 89 | $Sar_2$-ACPWGP(NO2Phe5)WCPVNRPGC | 91 | TBMB | | 289.5 ± 93.1 |
| 90 | $Sar_2$-ACPWGP(3,4-DCPhe)WCPVNRPGC | 92 | TBMB | | 361 ± 25.48 |
| 91 | $Sar_2$-ACPWGPYWCPVNRPGC | 93 | TBMB | | 137.63 ± 104.2 |
| 92 | $Sar_2$-ACPWGP(3Pal)WCPVNRPGC | 94 | TBMB | | 165 ± 27.44 |
| 93 | $Sar_2$-ACPWGP(Phg)WCPVNRPGC | 95 | TBMB | | 411.5 ± 128.38 |
| 94 | $Sar_2$-ACPWGP(1Nal)WCPVNRPGC | 96 | TBMB | | 196.5 ± 6.86 |
| 95 | $Sar_2$-ACPWGP(2Nal)WCPVNRPGC | 97 | TBMB | | 362.5 ± 110.74 |
| 96 | $Sar_2$-ACPWGPF(1Nal)CPVNRPGC | 98 | TBMB | 31.3 ± 24.11 | 68.13 ± 35.66 |
| 97 | $Sar_2$-ACPWGPFWC(Aze)VNRPGC | 99 | TBMB | | 286 ± 109.76 |
| 98 | $Sar_2$-ACPWGPFWC(HyP)VNRPGC | 100 | TBMB | | 163.33 ± 38.41 |
| 99 | $Sar_2$-ACPWGPFWC(4FlPro)VNRPGC | 101 | TBMB | | 269.5 ± 6.86 |
| 100 | $Sar_2$-ACPWGPFWCP(tBuGly)NRPGC | 102 | TBMB | 58.3 ± 50.37 | 112.45 ± 73.38 |
| 101 | $Sar_2$-ACPWGPFWCPVARPGC | 103 | TBMB | 293 n = 1 | 265 ± 235.04 |
| 102 | $Sar_2$-ACPWGPFWCPV(D-Ala)RPGC | | TBMB | 317 ± 168.56 | 311.67 ± 195.55 |
| 103 | $Sar_2$-ACPWGPFWCPVN(HArg)PGC | 104 | TBMB | 126 ± 9.8 | 169.43 ± 94.28 |
| 104 | $Sar_2$-ACPWGPFWCPVNRAGC | 105 | TBMB | 124 n = 1 | 193.67 ± 112.76 |

TABLE 6-continued

Biological Assay Data for Reference Peptide Ligands (Competition Binding Assay)

| Bicycle Compound Number | Sequence | SEQ ID NO: | Scaffold | Ki, nM ± 95% CI Human EphA2 Fluorescent Peptide Compound 18 | Compound 66 |
|---|---|---|---|---|---|
| 105 | Sar$_2$-ACPWGPFWCPVNR(D-Ala)GC | | TBMB | | 470.67 ± 221.53 |
| 106 | Sar$_2$-ACPWGPFWCPVNR(Aze)GC | 106 | TBMB | | 155 ± 47.04 |
| 107 | Sar$_2$-ACPWGPFWCPVNR(HyP)GC | 107 | TBMB | 48.7 n = 1 | 85.83 ± 57.98 |
| 108 | Sar$_2$-ACPWGPFWCPVNR(Pip)GC | 108 | TBMB | | 374.5 ± 12.74 |
| 109 | Sar$_2$-ACPWGPFWCPVNR(4FlPro)GC | 109 | TBMB | | 184.5 ± 20.58 |
| 110 | Sar$_2$-ACPWGPFWCPVNR(Aib)GC | 110 | TBMB | 75 ± 13.72 | 139.53 ± 103.98 |
| 111 | Sar$_2$-ACPWGPFWCPVNRPAC | 111 | TBMB | 108 n = 1 | 237.5 ± 164.92 |
| 112 | Sar$_2$-ACPWGPFWCPVNRP(D-Ala)C | | TBMB | 89 ± 15.68 | |
| 113 | Sar$_2$-AC(Aib)(1Nal)GPFWCPVNRPGC | 112 | TBMB | 10 n = 1 | 6.6 n = 1 |
| 114 | Sar$_2$-AC(Aib)WGPF(1Nal)CPVNRPGC | 113 | TBMB | 21 n = 1 | 43 n = 1 |
| 115 | Sar$_2$-ACP(1Nal)GPFWCPV(D-Ala)RPGC | | TBMB | 12.5 ± 0.98 | 1.64 ± 2.48 |
| 116 | Sar$_2$-ACP(1Nal)GPFWCPVNRP(D-Ala)C | | TBMB | 2.95 ± 1.67 | 3.2 n = 1 |
| 117 | Sar$_2$-ACPWGPF(1Nal)CPV(D-Ala)RPGC | | TBMB | 53 n = 1 | 75 n = 1 |
| 118 | Sar$_2$-ACPWGPF(1Nal)CPVNRP(D-Ala)C | | TBMB | 37 n = 1 | 18 ± 13.72 |
| 119 | Sar$_2$-ACP(1Nal)G(Aib)FWCPVNRPGC | 114 | TBMB | 21 n = 1 | 8.4 n = 1 |
| 120 | Sar$_2$-ACP(1Nal)GPF(1Nal)CPVNRPGC | 115 | TBMB | 1.4 ± 0.39 | 0.98 n = 1 |
| 121 | Sar$_2$-ACP(1Nal)GPFWCP(tBuGly)NRPGC | 116 | TBMB | 3.65 ± 0.29 | 2 n = 1 |
| 122 | Sar$_2$-ACP(1Nal)GPFWCPVN(HArg)PGC | 117 | TBMB | 9.55 ± 0.69 | 8 n = 1 |
| 123 | Sar$_2$-ACPWG(Aib)F(1Nal)CPVNRPGC | 118 | TBMB | 63 n = 1 | 46 n = 1 |
| 124 | Sar$_2$-AC(Aib)(1Nal)GPFWCPV(D-Ala)RPGC | | TBMB | 26 n = 1 | 2.5 n = 1 |
| 125 | Sar$_2$-AC(Aib)(1Nal)GPFWCPVNRP(D-Ala)C | | TBMB | 6.4 ± 0.78 | 0.61 ± 0.96 |
| 126 | Sar$_2$-ACP(1Nal)G(Aib)FWCP(tBuGly)NRPGC | 119 | TBMB | 15 n = 1 | 19 n = 1 |
| 127 | Sar$_2$-ACP(1Nal)G(Aib)FWCPV(D-Ala)RPGC | | TBMB | 40 n = 1 | 33 n = 1 |
| 128 | Sar$_2$-ACP(1Nal)G(Aib)FWCPVNRP(D-Ala)C | | TBMB | 15 n = 1 | 16 n = 1 |
| 129 | Sar$_2$-ACP(1Nal)GPFWCP(tBuGly)(D-Ala)RPGC | | TBMB | 23 n = 1 | 15 n = 1 |
| 130 | Sar$_2$-ACP(1Nal)GPFWCP(tBuGly)N(HArg)PGC | 120 | TBMB | 0.29 ± 0.34 | |
| 131 | Sar$_2$-ACP(1Nal)GPFWCP(tBuGly)NR(Aib)GC | 121 | TBMB | 11 n = 1 | 6.8 n = 1 |
| 132 | Sar$_2$-ACP(1Nal)GPFWCP(tBuGly)NRP(D-Ala)C | | TBMB | 7.7 ± 1.96 | 8.7 n = 1 |
| 133 | Sar$_2$-ACP(1Nal)GPFWCPV(D-Ala)(HArg)PGC | | TBMB | 14 n = 1 | 3.7 n = 1 |
| 134 | Sar$_2$-ACP(1Nal)GPFWCPVN(HArg)P(D-Ala)C | | TBMB | 1.2 n = 1 | 6.15 ± 0.29 |
| 135 | Sar$_2$-AC(Aib)(1Nal)G(Aib)FWCPVNR(Aib)GC | 122 | TBMB | 43 n = 1 | 30 n = 1 |
| 136 | Sar$_2$-ACP(1Nal)G(Aib)FWCP(tBuGly)N(HArg)PGC | 123 | TBMB | 23 n = 1 | 15 n = 1 |
| 137 | Sar$_2$-ACP(1Nal)G(Aib)FWCP(tBuGly)NR(Aib)GC | 124 | TBMB | 20 n = 1 | 18 n = 1 |
| 138 | Sar$_2$-ACP(1Nal)GPFWCP(tBuGly)N(HArg)(Aib)GC | 125 | TBMB | 5.1 n = 1 | |

TABLE 7

Biological Assay Data for Reference Peptide Ligands (Direct Binding Assay)

| Bicycle Compound Number | Sequence | Scaffold | $K_D$, nM ± 95% CI Human EphA2 | $K_D$, nM ± 95% CI Mouse EphA2 |
|---|---|---|---|---|
| 139 | AF488-(β-Ala)-Sar$_{10}$-H(D-Asp)VPCPWGPFWCPVNRPGCA | TBMB | 0.31 ± 0.18 | 0.8 ± 0.54 |
| 140 | AF488-(β-Ala)-Sar$_{10}$-H(D-Asp)VP-C(Aib)(1Nal)G(Aib)F(1Nal)CP(tBuGly)N(HArg)P(D-Asp)C | TBMB | 2.05 ± 0.62 | 4.55 ± 1.04 |
| 141 | AF488-(β-Ala)-Sar$_{10}$-H(D-Asp)VP-C(Aib)(1Nal)G(Aib)F(1Nal)CP(tBuGly)NR(Aib)(D-Asp)C | TBMB | 2.65 ± 0.64 | 6.5 ± 0.63 |
| 142 | Fl-(β-Ala)-Sar$_{10}$-H(D-Asp)VP-CP(1Nal)G(Aib)F(1Nal)CP(tBuGly)N(HArg)P(D-Asp)C | TBMB | 1.7 n = 1 | |
| 143 | AF488-(β-Ala)-Sar$_{10}$-H(D-Asp)VP-CP(1Nal)G(Aib)F(1Nal)CP(tBuGly)N(HArg)P(D-Asp)C | TBMB | 1.4 ± 1.46 | 4.69 ± 4.15 |
| 144 | AF488-(β-Ala)-Sar$_{10}$-H(D-Asp)VP-CP(1Nal)G(Aib)F(1Nal)CP(tBuGly)NR(Aib)GC | TBMB | 1.04 n = 1 | 2.56 n = 1 |
| 145 | AF488-(β-Ala)-Sar$_{10}$-H(D-Asp)VP-CP(1Nal)G(Aib)F(1Nal)CP(tBuGly)NR(Aib)(D-Asp)C | TBMB | 2.17 ± 2.08 | 3.8 ± 0.55 |
| 146 | AF488-(β-Ala)-Sar$_{10}$-H(D-Asp)(C5g)P-C(Aib)(1Nal)G(Aib)F(1Nal)CP(tBuGly)NR(Aib)(D-Asp)C | TBMB | 2.19 n = 1 | |
| 147 | AF488-(β-Ala)-Sar$_{10}$-H(D-Asp)(C5g)P-CP(1Nal)G(Aib)F(1Nal)CP(tBuGly)N(HArg)P(D-Asp)C | TBMB | 1.07 ± 0.9 | 3.44 ± 1.31 |

TABLE 8

Biological Assay Data for Reference Peptide Ligands (Competition Binding Assay)

| Bicycle Compound Number | Sequence | Scaffold | Ki, nM ± 95% CI Human EphA2 Fluorescent peptide Compound 18 | Ki, nM ± 95% CI Mouse EphA Fluorescent peptide Compound 18 |
|---|---|---|---|---|
| 148 | Ac-Sar$_2$-ADVH-CPWGPFWCPVNRPGC (SEQ ID NO: 126) | TBMB | 1.2 ± 0.2 | |
| 149 | ADVH-CP(3,3-DPA)GPFWCPVNRPGCA (SEQ ID NO: 127) | TBMB | 52.8 ± 11.6 | |
| 150 | ADVH-CP(1Nal)GPFWCPVNRPGCA (SEQ ID NO: 128) | TBMB | 0.12 ± 0.07 | |
| 151 | ADVH-CPWAPFWCPVNRPGCA (SEQ ID NO: 129) | TBMB | 393.5 ± 206.78 | |
| 152 | ADVH-CPWGAFWCPVNRPGCA (SEQ ID NO: 130) | TBMB | 1.8 ± 0.74 | |
| 153 | ADVH-CPWG(Aib)FWCPVNRPGCA (SEQ ID NO: 131) | TBMB | 0.51 ± 0.29 | |
| 154 | ADVH-CPWGPFWCAPVNRPGCA (SEQ ID NO: 132) | TBMB | 101.03 ± 33.68 | |
| 155 | ADVH-CPWGPFWCPV(D-Ala)RPGCA | TBMB | 2 ± 0.74 | |
| 156 | ADVH-CPWGPFWCPVN(D-Ala)PGCA | TBMB | 14.93 ± 2.3 | |
| 157 | Ac-Sar$_2$-ADVT-CPWGPFWCPVNRPGC (SEQ ID NO: 133) | TBMB | 0.91 ± 0.19 | |
| 158 | Ac-Sar$_2$-A(D-Asp)VT-CPWGPFWCPVNRPGC | TBMB | 2.05 ± 0.42 | 2.2 ± 0.4 |
| 159 | Ac-Sar$_2$-A(D-Asp)(D-Asp)T-CPWGPFWCPVNRPGC | TBMB | 2.85 ± 0.49 | |
| 160 | Ac-Sar$_2$-A(D-Asp)(Cba)T-CPWGPFWCPVNRPGC | TBMB | 2.6 ± 0.11 | |
| 161 | Ac-Sar$_2$-A(D-Asp)(Cpa)T-CPWGPFWCPVNRPGC | TBMB | 4.44 ± 1.08 | |
| 162 | Ac-Sar$_2$-A(D-Asp)(Cpg)T-CPWGPFWCPVNRPGC | TBMB | 2.55 ± 0.55 | |
| 163 | Ac-Sar$_2$-A(D-Asp)(C5g)VT-CPWGPFWCPVNRPGC | TBMB | 1.33 ± 0.27 | 1.74 ± 1.23 |
| 164 | Ac-Sar$_2$-AD(tBuGly)T-CPWGPFWCPVNRPGC (SEQ ID: 134) | TBMB | 2.25 ± 0.69 | |
| 165 | Ac-Sar$_2$-A(D-Asp)VT-C(AC3C)WGPFWCPVNRPGC | TBMB | 185 ± 147 | |
| 166 | Ac-Sar$_2$-A(D-Asp)VT-C(AC4C)WGPFWCPVNRPGC | TBMB | 76.7 ± 73.11 | |
| 167 | Ac-Sar$_2$-A(D-Asp)VT-C(AC5C)WGPFWCPVNRPGC | TBMB | 138 n = 1 | |
| 168 | Ac-Sar$_2$-A(D-Asp)VT-C(4BenzyPro)WGPFWCPVNRPGC | TBMB 2 | 5.03 ± 2.24 | |

TABLE 8-continued

Biological Assay Data for Reference Peptide Ligands
(Competition Binding Assay)

| Bicycle Compound Number | Sequence | Scaffold | Ki, nM ± 95% CI Human EphA2 Fluorescent peptide Compound 18 | Mouse EphA Compound 18 |
|---|---|---|---|---|
| 169 | Ac-Sar$_2$-A(D-Asp)VT-C(4PhenyPro)WGPFWCPVNRPGC | TBMB | 14.4 ± 7.64 | |
| 170 | Ac-Sar$_2$-A(D-Asp)VT-CP(1Nal)GPFWCPVNRPGC | TBMB | 0.6 ± 0.19 | |
| 171 | Ac-Sar$_2$-A(D-Asp)VT-CPWGP(HArg)WCPVNRPGC | TBMB | 4.88 ± 2.19 | |
| 172 | Ac-Sar$_2$-A(D-Asp)VT-CPWGPNWCPVNRPGC | TBMB | 3.96 ± 0.72 | |
| 173 | Ac-Sar$_2$-A(D-Asp)VT-CPWGPAWCPVNRPGC | TBMB | 6.69 ± 3.49 | |
| 174 | Ac-Sar$_2$-A(D-Asp)VT-CPWGPFWCPLNRPGC | TBMB | 9.1 ± 1.73 | |
| 175 | Ac-Sar$_2$-A(D-Asp)VT-CPWGPFWCPVN(HArg)P(D-Asp)C | TBMB | 1.78 ± 0.54 | |
| 176 | Ac-Sar$_2$-A(D-Asp)VT-CPWGPFWCPVN(HArg)P(D-Asp)C | TBMB | 4.89 ± 0.97 | |
| 177 | Ac-Sar$_2$-A(D-Asp)VT-CPWGPFWCPVNR(Aib)(D-Asp)C | TBMB | 4.43 ± 2.37 | |
| 178 | Ac-Sar$_2$-A(D-Asp)VT-CP(1Nal)G(Aib)FWCPVNR(Aib)GC | TBMB | 2.4 ± 0.23 | |
| 179 | Ac-Sar$_2$-A(D-Asp)VT-CPWG(Aib)F(1Nal)CPVNR(Aib)GC | TBMB | 2.94 ± 0.09 | |
| 180 | Ac-Sar$_2$-A(D-Asp)VT-CPWG(Aib)FWCP(tBuGly)NR(Aib)GC | TBMB | 3.83 ± 0.43 | |
| 181 | Ac-Sar$_2$-A(D-Asp)VT-CP(1Nal)G(Aib)F(1Nal)CPVNR(Aib)GC | TBMB | 1.37 ± 0.41 | |
| 182 | Ac-Sar$_2$-A(D-Asp)VT-CP(1Nal)G(Aib)F(1Nal)CP(tBuGly)N(HArg)PGC | TBMB | 1.16 ± 0.39 | |
| 183 | Ac-Sar$_2$-A(D-Asp)VT-CP(1Nal)G(Aib)F(1Nal)CP(tBuGly)NR(Aib)GC | TBMB | 1.02 ± 0.41 | |
| 184 | Ac-Sar$_2$-A(D-Asp)VT-CP(1Nal)G(Aib)F(1Nal)CP(tBuGly)N(HArg)P(D-Asp)C | TBMB | 1.19 ± 0.29 | |
| 185 | (D-Asp)VT-CPWGPFWCPVNRPGC | TBMB | 2.17 ± 0.73 | |
| 186 | (D-Asp)VT-CP(1Nal)G(Aib)F(1Nal)CP(tBuGly)NR(Aib)GC | TBMB | 1.34 ± 0.18 | |
| 187 | AHDVP-CP(1Nal)GPFWCPVNRPGCA (SEQ ID NO: 135) | TBMB | 0.32 ± 0.03 | |
| 188 | AHDVP-CP(1Nal)GPFWCPVNRPGC (SEQ ID NO: 136) | TBMB | 1.45 ± 0.1 | |
| 189 | AHDVP-CPWGPF(1Nal)CPVNRPGC (SEQ ID NO: 137) | TBMB | 1.3 ± 0.2 | |
| 190 | AHDVP-CP(1Nal)GPFWCP(tBuGly)NRPGC (SEQ ID NO: 138) | TBMB | 0.7 ± 0.4 | |
| 191 | AHDVP-CP(1Nal)G(Aib)FWCP(tBuGly)N(HArg)PGC (SEQ ID NO: 139) | TBMB | 3.1 ± 0.68 | |
| 192 | AHDVP-CP(1Nal)G(Aib)FWCP(tBuGly)NR(Aib)GC (SEQ ID NO: 140) | TBMB | 1.75 ± 0.1 | |
| 193 | Ac-Sar$_2$-AHDVP-CPWGPFWCPVNRPGC (SEQ ID NO: 141) | TBMB | 0.59 ± 0.2 | |
| 194 | Ac-Sar$_2$-(D-Ala)HDVP-CPWGPFWCPVNRPGC | TBMB | 1.2 ± 0.39 | |
| 195 | Ac-Sar$_2$-AADVP-CPWGPFWCPVNRPGC (SEQ ID NO: 142) | TBMB | 1.01 ± 0.19 | |
| 196 | Ac-Sar$_2$-A(D-His)DVP-CPWGPFWCPVNRPGC | TBMB | 0.95 ± 0.24 | |
| 197 | Sar-A(D-His)DVP-CPWGPFWCPVNRPGC | TBMB | 1.2 | |
| 198 | Ac-Sar$_2$-A(D-His)DVCPWGPFWCPVNRPGC | TBMB | 20 ± 1.96 | |
| 199 | Sar-A(D-Ala)DVP-CPWGPFWCPVNRPGC | TBMB | 3.35 ± 1.47 | |
| 200 | Ac-Sar$_2$-A(D-Asp)DVP-CPWGPFWCPVNRPGC | TBMB | 4.1 ± 0.2 | |
| 201 | Sar-A(Thi)DVP-CPWGPFWCPVNRPGC (SEQ ID NO: 143) | TBMB | 0.6 ± 0.04 | |
| 202 | Sar-A(ThiAz)DVP-CPWGPFWCPVNRPGC (SEQ ID NO: 144) | TBMB | 0.7 ± 0.08 | |
| 203 | Sar$_2$-A(2FuAla)DVP-CPWGPFWCPVNRPGC (SEQ ID NO: 145) | TBMB | 0.49 ± 0.24 | |
| 204 | Ac-Sar$_2$-A(D-His)D(tBuGly)P-CPWGPFWCPVNRPGC | TBMB | 2.15 ± 0.1 | |
| 205 | Sar$_2$-AHAVP-CPWGPFWCPVNRPGC (SEQ ID NO: 146) | TBMB | 1.8 ± 0.2 | |
| 206 | Sar$_2$-AH(D-Ala)VP-CPWGPFWCPVNRPGC | TBMB | 8.3 ± 0.78 | |
| 207 | Sar2-AHEVP-CPWGPFWCPVNRPGC (SEQ ID NO: 147) | TBMB | 1.3 ± 0.39 | |
| 208 | Sar$_2$-AH(D-Glu)VP-CPWGPFWCPVNRPGC | TBMB | 2 ± 0.39 | |
| 209 | Sar$_2$-AH(D-Asp)VP-CPWGPFWCPVNRPGC | TBMB | 1.25 ± 0.29 | |
| 210 | Ac-Sar$_2$-AH(D-Asp)VP-CPWGPFWCPVNRPGC | TBMB | 1.1 ± 0.2 | |
| 211 | Ac-Sar$_2$-AH(D-Asp)(tBuGly)P-CPWGPFWCPVNRPGC | TBMB | 3.1 ± 0.2 | |
| 212 | Ac-Sar$_2$-AH(D-Asp)V(Sar)-CPWGPFWCPVNRPGC | TBMB | 4.95 ± 1.86 | |
| 213 | Ac-Sar$_2$-AH(D-Asp)V(Aib)CPWGPFWCPVNRPGC | TBMB | 1.9 ± 0.2 | |
| 214 | Sar$_2$-AHDAP-CPWGPFWCPVNRPGC (SEQ ID NO: 148) | TBMB | 22.5 ± 2.94 | |
| 215 | Sar$_2$-AHD(D-Ala)P-CPWGPFWCPVNRPGC | TBMB | 26 ± 7.84 | |
| 216 | Sar$_2$-AHD(Aib)P-CPWGPFWCPVNRPGC (SEQ ID NO: 149) | TBMB | 2.77 ± 0.24 | |
| 217 | Sar$_2$-AHD(tBuGly)P-CPWGPFWCPVNRPGC (SEQ ID NO: 150) | TBMB | 0.49 n = 1 | |
| 218 | Sar$_2$-AHDVA-CPWGPFWCPVNRPGC (SEQ ID NO: 151) | TBMB | 1.27 ± 0.07 | |
| 219 | Sar$_2$-AHDV(D-Ala)-CPWGPFWCPVNRPGC | TBMB | 15 ± 3.92 | |

TABLE 8-continued

Biological Assay Data for Reference Peptide Ligands
(Competition Binding Assay)

| Bicycle Compound Number | Sequence | Scaffold | Ki, nM ± 95% CI Human EphA2 Fluorescent peptide Compound 18 | Ki, nM ± 95% CI Mouse EphA Fluorescent peptide Compound 18 |
|---|---|---|---|---|
| 220 | Sar₂-AHDV(Aib)-CPWGPFWCPVNRPGC (SEQ ID NO: 152) | TBMB | 0.83 ± 0.15 | |
| 221 | Sar₂-AHDV(Aze)-CPWGPFWCPVNRPGC (SEQ ID NO: 153) | TBMB | 3.1 ± 0.39 | |
| 222 | Sar₂-AHDV(Pip)-CPWGPFWCPVNRPGC (SEQ ID NO: 154) | TBMB | 3.4 ± 0.2 | |
| 223 | (β-Ala)-Sar₁₀-HDVP-CPWGPFWCPVNRPGC (SEQ ID NO: 155) | TBMB | 1.29 ± 0.42 | |
| 224 | Ac-Sar₂-(D-His)DVP-CPWGPFWCPVNRPGC | TBMB | 1.09 ± 0.13 | |
| 225 | Ac-Sar₂-H(D-Asp)VP-CPWGPFWCPVNRPGC | TBMB | 1 ± 0.18 | 2.08 ± 1.27 |
| 226 | (β-Ala)-Sar₁₀-H(D-Asp)VP-CPWGPFWCPVNRPGC | TBMB | 0.84 ± 0.24 | |
| 227 | Ac-Sar₂-AH(D-Asp)VP-CP(1Nal)GPFWCP(tBuGly)N(HArg)PGC | TBMB | 0.75 ± 0.36 | |
| 228 | Ac-Sar₂-A(D-His)DVP-CPWGP(ΨAla)WCPVNRPGC | TBMB | 210.5 ± 48.02 | |
| 229 | Ac-Sar₂-A(D-His)DVP-CPWGPFWCP(HArg)NRPGC | TBMB | 5.1 ± 1.18 | |
| 230 | Ac-Sar₂-A(D-His)DVP-CP(1Nal)GPFWCP(tBuGly)N(HArg)PGC | TBMB | 1.8 ± 0.78 | |
| 231 | Ac-Sar₂-A(D-His)DVP-CP(1Nal)G(Aib)F(1Nal)CP(tBuGly)N(HArg)PGC | TBMB | 1.93 ± 0.23 | |
| 232 | Ac-Sar₂-A(D-His)DVP-CP(1Nal)G(Aib)F(1Nal)CP(tBuGly)NR(Aib)GC | TBMB | 0.9 ± 0.68 | |
| 233 | Ac-Sar₂-A(D-His)DVP-CPWG(Aib)FWCP(tBuGly)NR(Aib)GC | TBMB | 4.8 ± 0.84 | |
| 234 | (β-Ala)-Sar₁₀-H(D-Asp)VP-C(Aib)(1Nal)G(Aib)F(1Nal)CP(tBuGly)NRPGC | TBMB | 3.94 ± 1.72 | |
| 235 | (β-Ala)-Sar₁₀-H(D-Asp)VP-C(Aib)(1Nal)G(Aib)F(1Nal)CP(tBuGly)N(HArg)PGC | TBMB | 2.58 ± 0.96 | |
| 236 | (β-Ala)-Sar₁₀-H(D-Asp)VP-C(Aib)(1Nal)G(Aib)F(1Nal)CP(tBuGly)N(HArg)P(D-Asp)C | TBMB | 3 ± 0.71 | |
| 237 | Ac-(β-Ala)-Sar₁₀-H(D-Asp)VP-C(Aib)(1Nal)G(Aib)F(1Nal)CP(tBuGly)N(HArg)P(D-Asp)C | TBMB | 2.4 n = 1 | |
| 238 | (β-Ala)-Sar₁₀-H(D-Asp)VP-C(Aib)(1Nal)G(Aib)F(1Nal)CP(tBuGly)N(HArg)(Aib)(D-Asp)C | TBMB | 2.83 ± 0.19 | |
| 239 | (β-Ala)-Sar₁₀-H(D-Asp)VP-C(Aib)(1Nal)G(Aib)F(1Nal)CP(tBuGly)NR(Aib)GC | TBMB | 4.91 ± 2.45 | |
| 240 | (β-Ala)-Sar₁₀-H(D-Asp)VP-C(Aib)(1Nal)G(Aib)F(1Nal)CP(tBuGly)NR(Aib)(D-Asp)C | TBMB | 2.41 n = 1 | |
| 241 | Ac-(β-Ala)-Sar₁₀-H(D-Asp)VP-C(Aib)(1Nal)G(Aib)F(1Nal)CP(tBuGly)NR(Aib)(D-Asp)C | TBMB | 2.98 ± 0.96 | |
| 242 | (β-Ala)-Sar₁₀-H(D-Asp)VP-C(Aib)(1Nal)G(Aib)FWCP(tBuGly)N(HArg)P(D-Asp)C | TBMB | 7.77 ± 3.02 | |
| 243 | (β-Ala)-Sar₁₀-H(D-Asp)VP-C(Aib)(1Nal)GP(HArg)(1Nal)CP(tBuGly)NR(Aib)GC | TBMB | 2.83 ± 0.72 | |
| 244 | (β-Ala)-Sar₁₀-H(D-Asp)VP-C(Aib)(1Nal)GP(HArg)(1Nal)CP(tBuGly)N(HArg)P(D-Asp)C | TBMB | 2.8 ± 0.26 | |
| 245 | (β-Ala)-Sar₁₀-H(D-Asp)VP-C(Aib)WGP(HArg)(1Nal)CP(tBuGly)N(HArg)P(D-Asp)C | TBMB | 11.91 ± 4.3 | |
| 246 | (β-Ala)-Sar₁₀-H(D-Asp)VP-C(Aib)WGP(HArg)WCP(tBuGly)N(HArg)P(D-Asp)C | TBMB | 31.4 ± 24.3 | |
| 247 | (β-Ala)-Sar₁₀-H(D-Asp)VP-C(Aib)WGP(HArg)WCP(tBuGly)N(HArg)P(D-Asp)C | TBMB | 29.7 ± 11.76 | |
| 248 | (β-Ala)-Sar₁₀-H(D-Asp)VP-C(D-Ala)(1Nal)G(Aib)F(1Nal)CP(tBuGly)N(HArg)P(D-Asp)C | TBMB | 28.4 ± 0.78 | |
| 249 | (β-Ala)-Sar₁₀-H(D-Asp)VP-CP(1Nal)G(Aib)(HArg)(1Nal)CP(tBuGly)NR(Aib)GC | TBMB | 1.38 ± 0.46 | |
| 250 | (β-Ala)-Sar₁₀-H(D-Asp)VP-CP(1Nal)G(Aib)(HArg)(1Nal)CP(tBuGly)NR(Aib)(D-Asp)C | TBMB | 1.48 ± 0.7 | |
| 251 | (β-Ala)-Sar₁₀-H(D-Asp)VP-CP(1Nal)G(Aib)(HArg)(1Nal)CP(tBuGly)N(HArg)P(D-Asp)C | TBMB | 1.93 ± 0.62 | |
| 252 | (β-Ala)-Sar₁₀-H(D-Asp)VP-CP(1Nal)G(Aib)F(1Nal)CP(tBuGly)NRPGC | TBMB | 0.37 ± 0.18 | |
| 253 | Ac-Sar₂-H(D-Asp)VP-CP(1Nal)G(Aib)F(1Nal)CP(tBuGly)N(HArg)PGC | TBMB | 0.85 ± 0.82 | |
| 254 | Ac-Sar₂-H(D-Asp)VP-CP(1Nal)G(Aib)F(1Nal)CP(tBuGly)N(HArg)P(D-Asp)C | TBMB | 0.74 ± 0.2 | 0.64 ± 0.28 |
| 255 | (β-Ala)-Sar₁₀-H(D-Asp)VP-CP(1Nal)G(Aib)F(1Nal)CP(tBuGly)N(HArg)P(D-Asp)C | TBMB | 1.53 ± 0.58 | |
| 256 | Ac-(β-Ala)-Sar₁₀-H(D-Asp)VP-CP(1Nal)G(Aib)F(1Nal)CP(tBuGly)N(HArg)P(D-Asp)C | TBMB | 0.41 n = 1 | |
| 257 | (β-Ala)-Sar₁₀-H(D-Asp)VP-CP(1Nal)G(Aib)F(1Nal)CP(tBuGly)N(HArg)PGC | TBMB | 1.07 ± 0.2 | |
| 258 | Ac-(β-Ala)-Sar₁₀-H(D-Asp)VP-CP(1Nal)G(Aib)F(1Nal)CP(tBuGly)NR(Aib)GC | TBMB | 0.54 n = 1 | |
| 259 | (β-Ala)-Sar₁₀-H(D-Asp)VP-CP(1Nal)G(Aib)F(1Nal)CP(tBuGly)N(HArg)(Aib)(D-Asp)C | TBMB | 0.91 ± 0.14 | |
| 260 | Ac-(β-Ala)-Sar₁₀-H(D-Asp)VP-CP(1Nal)G(Aib)F(1Nal)CP(tBuGly)NR(Aib)(D-Asp)C | TBMB | 0.75 ± 0.07 | |
| 261 | Ac-Sar₂-H(D-Asp)VP-CP(1Nal)G(Aib)F(1Nal)CPVNR(Aib)GC | TBMB | 0.63 ± 0.43 | |

TABLE 8-continued

Biological Assay Data for Reference Peptide Ligands
(Competition Binding Assay)

| Bicycle Compound Number | Sequence | Scaffold | Ki, nM ± 95% CI Human EphA2 Fluorescent peptide Compound 18 | Mouse EphA Fluorescent peptide Compound 18 |
|---|---|---|---|---|
| 262 | Ac-Sar₂-H(D-Asp)VP-CP(1Nal)G(Aib)F(1Nal)CP(tBuGly)NR(Aib)GC | TBMB | 0.71 ± 0.17 | 0.72 ± 0.31 |
| 263 | (β-Ala)-Sar₁₀-H(D-Asp)VP-CP(1Nal)G(Aib)F(1Nal)CP(tBuGly)NR(Aib)GC | TBMB | 0.73 ± 0.26 | |
| 264 | (β-Ala)-Sar₁₀-H(D-Asp)VP-CP(1Nal)G(Aib)F(1Nal)CP(tBuGly)NR(Aib)(D-Asp)C | TBMB | 0.61 ± 0.31 | |
| 265 | (β-Ala)-Sar₁₀-H(D-Asp)VP-CP(1Nal)G(Aib)FWCP(tBuGly)N(HArg)P(D-Asp)C | TBMB | 1.55 ± 0.34 | |
| 266 | Ac-Sar₂-H(D-Asp)VP-CP(1Nal)G(Aib)FWCPVNR(Aib)GC | TBMB | 1.6 ± 0.63 | |
| 267 | Ac-Sar₂-H(D-Asp)VP-CPW(Aza-Gly)PFWCPVNRPGC | TBMB | 0.66 ± 0.2 | |
| 268 | Ac-Sar₂-H(D-Asp)VP-CPWG(Aib)F(1Nal)CPVNR(Aib)GC | TBMB | 1.24 ± 0.46 | |
| 269 | (β-Ala)-Sar₁₀-H(D-Asp)VP-CPWG(Aib)F(1Nal)CP(tBuGly)N(Harg)P(D-Asp)C | TBMB | 1.11 ± 0.08 | |
| 270 | Ac-Sar₂-H(D-Asp)VP-CPWG(Aib)FWCP(tBuGly)NR(Aib)GC | TBMB | 1.52 ± 1.27 | |
| 271 | (β-Ala)-Sar₁₀-H(D-Asp)VP-CPWG(Aib)FWCP(tBuGly)N(HArg)P(D-Asp)C | TBMB | 3.66 ± 1.7 | |
| 272 | (β-Ala)-Sar₁₀-H(D-Asp)VP-CPWGP(HArg)WCP(tBuGly)N(HArg)P(D-Asp)C | TBMB | 3.99 ± 0.13 | |
| 273 | (β-Ala)-Sar₁₀-H(D-Asp)(C5g)P-C(Aib)(1Nal)G(Aib)F(1Nal)CP(tBuGly)NR(Aib)(D-Asp)C | TBMB | 1.5 n = 1 | |
| 274 | Ac-(β-Ala)-Sar₁₀-H(D-Asp)(C5g)P-C(Aib)(1Nal)G(Aib)F(1Nal)CP(tBuGly)NR(Aib)(D-Asp)C | TBMB | 2.28 ± 0.69 | |
| 275 | (β-Ala)-Sar₁₀-H(D-Asp)(C5g)P-C(Aib)WG(Aib)FWCP(tBuGly)NR(Aib)(D-Asp)C | TBMB | 15.9 ± 0.2 | |
| 276 | (β-Ala)-Sar₁₀-H(D-Asp)(C5g)P-CP(1Nal)G(Aib)F(1Nal)CP(tBuGly)N(HArg)P(D-Asp)C | TBMB | 0.62 ± 0.27 | |
| 277 | Ac-(β-Ala)-Sar₁₀-H(D-Asp)(C5g)P-CP(1Nal)G(Aib)F(1Nal)CP(tBuGly)N(HArg)P(D-Asp)C | TBMB | 0.53 ± 0.15 | |
| 278 | (β-Ala)-Sar₁₀-H(D-Asp)(C5g)P-CP(1Nal)G(Aib)F(1Nal)CP(tBuGly)NR(Aib)GC | TBMB | 0.46 ± 0.22 | |
| 279 | (β-Ala)-Sar₁₀-H(D-Asp)(C5g)T-CP(1Nal)G(Aib)F(1Nal)CP(tBuGly)NR(Aib)GC | TBMB | 0.59 ± 0.28 | |
| 280 | (β-Ala)-Sar₁₀-H(D-Asp)(C5g)T-CP(1Nal)G(Aib)F(1Nal)CP(tBuGly)N(HArg)P(D-Asp)C | TBMB | 0.64 ± 0.48 | |
| 281 | Ac-Sar₂-A(D-Asp)DVT-CPWGPFWCPVNRPGC | TBMB | 5.78 ± 1.1 | |
| 282 | Ac-Sar₂-A(D-Asp)DVT-CP(1Nal)GPFWCPVNRPGC | TBMB | 0.87 ± 0.14 | |
| 283 | Ac-Sar₂-A(D-Asp)DVT-CP(1Nal)GPF(1Nal)CPVNRPGC | TBMB | 0.28 ± 0.08 | |
| 284 | Ac-Sar₂-A(D-Asp)DVT-CP(1Nal)G(Aib)FWCP(tBuGly)N(HARrg)PGC | TBMB | 3.8 ± 0.77 | |
| 285 | Ac-Sar₂-H(D-Asp)VT-CP(1Nal)G(Aib)F(1Nal)CP(tBuGly)NR(Aib)GC | TBMB | 1.21 ± 0.29 | |

TABLE 9

Biological Assay Data for Reference Peptide Ligands
(Ala scan peptides, Competition Binding Assay)

| Bicycle Compound Number | Sequence | Scaffold | Ki, nM ± 95% CI Human EphA2 Fluorescent peptide Compound 66 | Compound 18 |
|---|---|---|---|---|
| 25 | Ac-CANDWLCSLGWTC (SEQ ID NO: 27) | TBMB | 328 n = 1 | |
| 26 | Ac-CMNDWLCALGWTC (SEQ ID NO: 28) | TBMB | 71.6 ± 3.33 | |
| 27 | Ac-CMNDWLCSAGWTC (SEQ ID NO: 29) | TBMB | 356 n = 1 | |
| 286 | Sar₂-ACAWGPFWCPVNRPGC (SEQ ID NO: 156) | TBMB | 886 ± 474.47 | |
| 287 | Sar₂-ACPAGPFWCPVNRPGC (SEQ ID NO: 157) | TBMB | >11000 | |
| 288 | Sar₂-ACPWAPFWCPVNRPGC (SEQ ID NO: 158) | TBMB | >28000 | >1000 |
| 289 | Sar₂-ACPWGAFWCPVNRPGC (SEQ ID NO: 159) | TBMB | 1102 ± 186.2 | >1000 |
| 83 | Sar₂-ACPWGPAWCPVNRPGC (SEQ ID NO: 85) | TBMB | 287.5 ± 197.95 | 199 n = 1 |
| 290 | Sar₂-ACPWGPFACPVNRPGC (SEQ ID NO: 160) | TBMB | >7000 | |
| 291 | Sar₂-ACPWGPFWCAVNRPGC (SEQ ID NO: 161) | TBMB | >6000 | >1000 |
| 292 | Sar₂-ACPWGPFWCPANRPGC (SEQ ID NO: 162) | TBMB | 953.5 ± 59.78 | |
| 101 | Sar₂-ACPWGPFWCPVARPGC (SEQ ID NO: 103) | TBMB | 265 ± 235.04 | 293 n = 1 |
| 293 | Sar₂-ACPWGPFWCPVNAPGC (SEQ ID NO: 163) | TBMB | 711 ± 581.64 | |

TABLE 9-continued

Biological Assay Data for Reference Peptide Ligands
(Ala scan peptides, Competition Binding Assay)

| Bicycle Compound Number | Sequence | Scaffold | Ki, nM ± 95% CI Human EphA2 Fluorescent peptide Compound 66 | Compound 18 |
|---|---|---|---|---|
| 104 | $Sar_2$-ACPWGPFWCPVNRAGC (SEQ ID NO: 105) | TBMB | 193.67 ± 112.76 | 124 n = 1 |
| 111 | $Sar_2$-ACPWGPFWCPVNRPAC (SEQ ID NO: 111) | TBMB | 237.5 ± 164.92 | 108 n = 1 |
| 294 | $Sar_2$-AC(D-Ala)WGPFWCPVNRPGC | TBMB | >4000 | |
| 295 | $Sar_2$-ACP(D-Ala)GPFWCPVNRPGC | TBMB | >7000 | |
| 296 | $Sar_2$-ACPW(D-Ala)PFWCPVNRPGC | TBMB | 1003 n = 1 | |
| 297 | $Sar_2$-ACPWG(D-Ala)FWCPVNRPGC | TBMB | 1497 n = 1 | |
| 298 | $Sar_2$-ACPWGP(D-Ala)WCPVNRPGC | TBMB | >6500 | |
| 299 | $Sar_2$-ACPWGPF(D-Ala)CPVNRPGC | TBMB | >4000 | |
| 300 | $Sar_2$-ACPWGPFC(D-Ala)VNRPGC | TBMB | >1200 | |
| 301 | $Sar_2$-ACPWGPFWCP(D-Ala)NRPGC | TBMB | >4000 | |
| 102 | $Sar_2$-ACPWGPFWCPV(D-Ala)RPGC | TBMB | 311.67 ± 195.55 | 317 ± 168.56 |
| 302 | $Sar_2$-ACPWGPFWCPVN(D-Ala)PGC | TBMB | 1410 ± 680.11 | >1000 |
| 105 | $Sar_2$-ACPWGPFWCPVNR(D-Ala)GC | TBMB | 470.67 ± 221.53 | 677 n = 1 |
| 112 | $Sar_2$-ACPWGPFWCPVNRP(D-Ala)C | TBMB | 109.83 ± 66.19 | 89 ± 15.68 |
| 303 | (β-Ala)-$Sar_{10}$-ACWAPFWCAVNRPGC (SEQ ID NO: 164) | TBMB | >1000 | |
| 304 | 4-(pyridyl-2-disulfanyl)-4-RS-methylbutanoyl-(β-Ala)-$Sar_{10}$-ACPWAPFWCAVNRPGC (SEQ ID NO: 165) | TBMB | >10000 | |
| 173 | Ac-$Sar_2$-A(D-Asp)VTCPWGPAWCPVNRPGC | TBMB | 6.69 ± 3.49 | |
| 305 | (β-Ala)-$Sar_{10}$-H(D-Asp)VPCP(1Nal)A(Aib)F(1Nal)CA(tBuGly)NR(Aib)(D-Asp)C | TBMB | >5000 | |
| 151 | ADVHCPW(Ala)PFWCPVNRPGCA (SEQ ID NO: 166) | TBMB | 393.5 ± 206.78 | |
| 152 | ADVHCPWG(Ala)FWCPVNRPGCA (SEQ ID NO: 167) | TBMB | 1.8 ± 0.74 | |
| 154 | ADVHCPWGPFWC(D-Ala)VNRPGCA | TBMB | 101.03 ± 33.68 | |
| 155 | ADVHCPWGPFWCPV(D-Ala)RPGCA | TBMB | 2 ± 0.74 | |
| 156 | ADVHCPWGPFWCPVN(D-Ala)PGCA | TBMB | 14.93 ± 2.3 | |
| 306 | DOTA-(β-Ala)-$Sar_{10}$-H(D-Asp)VPCP(1Nal)A(Aib)F(1Nal)CA(tBuGly)NR(Aib)(D-Asp)C | TBMB | >250 | |

TABLE 10

Biological Assay Data for Reference Peptide Ligands
(Ala scan peptides, Direct Binding Assay)

| Bicycle Compound Number | Sequence | Scaffold | $K_D$, nM ± 95% CI Human EphA2 |
|---|---|---|---|
| 307 | AF488-(β-Ala)-$Sar_{10}$-ACPWAPFWCAVNRPGC (SEQ ID NO: 168) | TBMB | >1000 |
| 308 | AF488-(β-Ala)-$Sar_{10}$-H(D-Asp)VPCP(1Nal)A(Aib)F(1Nal)CA(tBuGly)NR(Aib)(D-Asp)C | TBMB | >2000 |

Reference Examples B1-B98

The following reference peptide ligands having a TATA scaffold with three thioether linkages to cysteine residues of the specified peptide sequences were prepared and evaluated for affinity to EphA2 as described in detail in our earlier application GB201721259.8 filed 19 Dec. 2017.

In view of the results obtained above in Examples 1-6, it is predicted that derivatives of the reference examples B1-B98 according to the present invention, i.e. having alkylamino linkages in place of one or more of the thioether linkages in the reference examples, will also display affinity for EphA2. It is further predicted that derivatives of the reference examples B1-B98 having scaffolds other than TATA, in particular non-aromatic scaffolds other than TATA, will also display affinity for EphA2. All such derivatives having affinity for EphA2 are therefore included within the scope of the present invention.

TABLE 11

Biological Assay Data for Reference Peptide Ligands
(TATA peptides, Direct Binding Assay)

| Bicycle Compound Number | Sequence | SEQ ID NO: | Scaffold | Human EphA2 ($K_D$, nM ± 95% CI) |
|---|---|---|---|---|
| 1 | ACMNDWWCAMGWKCA-$Sar_6$-K(Fl) | 169 | TATA | 304 ± 91.99 |
| 2 | ACVPDRRCAYMNVCA-$Sar_6$-K(Fl) | 170 | TATA | 74.91 ± 6.6 |
| 3 | ACVVDGRCAYMNVCA-$Sar_6$-K(Fl) | 171 | TATA | 129.8 ± 80.75 |
| 4 | ACVVDSRCAYMNVCA-$Sar_6$-K(Fl) | 172 | TATA | 124.6 ± 51.74 |
| 5 | ACVPDSRCAYMNVCA-$Sar_6$-K(Fl) | 173 | TATA | 93.95 ± 23.62 |
| 6 | ACYVGKECAIRNVCA-$Sar_6$-K(Fl) | 174 | TATA | 168.5 ± 20.58 |
| 7 | ACYVGKECAYMNVCA-$Sar_6$-K(Fl) | 175 | TATA | 149.73 ± 39.2 |
| 8 | Fl-G-$Sar_5$-ACYVGKECAYMNVCA | 176 | TATA | 218.33 ± 10.51 |
| 9 | Fl-(β-Ala)-$Sar_{10}$-ARDCPLVNPLCLHPGWTC | 177 | TATA | 6.43 ± 1.15 |
| 10 | Fl-(β-Ala)-$Sar_{10}$-A(HArg)DCPLVNPLCLHPGWTC | 178 | TATA | 9.07 ± 2.49 |
| 11 | Ac-CPLVNPLCLHPGWTCLHG-$Sar_6$-(D-K[Fl]) | | TATA | 3.08 ± 0.43 |
| 12 | Ac-CPLVNPLCLHPGWTCL(D-His)G-$Sar_6$-(D-K[Fl]) | | TATA | 10.56 ± 0.77 |
| 13 | Ac-CPLVNPLCLHPGWSCRGQ-$Sar_6$-(D-K[Fl]) | | TATA | 5.29 ± 0.79 |

TABLE 11-continued

Biological Assay Data for Reference Peptide Ligands (TATA peptides, Direct Binding Assay)

| Bicycle Compound Number | Sequence | SEQ ID NO: | Scaffold | Human EphA2 ($K_D$, nM ± 95% CI) |
|---|---|---|---|---|
| 14 | Ac-CPLVNPLCLHPGWSC(HArg)GQ-Sar$_6$-(D-K[Fl]) | | TATA | 9.96 ± 0.55 |

TABLE 12

Biological Assay Data for Peptide Ligands of the Invention (TATA peptides, Competition Binding Assay)

| | | | | Ki, nM ± 95% CI | | | |
|---|---|---|---|---|---|---|---|
| | | | | Fluorescent Peptide | | | |
| | | | | Human EphA2 | | | Mouse EphA2 |
| Bicycle Compound Number | Sequence | SEQ ID NO: | Scaffold | Reference Compound C | Reference Compound B | Reference Compound A | Reference Compound C |
| 15 | ACMNDWWCAMGWKCA | 179 | TATA | 277.5 ± 38.22 | | | |
| 16 | ACVPDRRCAYMNVCA | 180 | TATA | 69.97 ± 8.67 | | | |
| 17 | (β-Ala)-Sar$_{10}$-ACVPDRRCAYMNVC | 181 | TATA | 85.05 ± 1.08 | | | |
| 18 | DLRCGGDPRCAYMNVCA | 182 | TATA | 70.8 ± 2.35 | | | |
| 19 | SRPCVIDSRCAYMNVCA | 183 | TATA | 94.75 ± 24.01 | | | |
| 20 | ESRCSPDARCAYMNVCA | 184 | TATA | 57.05 ± 4.61 | | | |
| 21 | HSGCRPDPRCAYMNVCA | 185 | TATA | 62.15 ± 4.61 | | | |
| 22 | GSGCKFDSRCAYMNVCA | 186 | TATA | 63.25 ± 13.82 | | | |
| 23 | ETVCLPDSRCAYMNVCA | 187 | TATA | 130 ± 15.68 | | | |
| 24 | GQVCIVDARCAYMNVCA | 188 | TATA | 168.5 ± 16.66 | | | |
| 25 | ACVPDRRCAFENVCVDH | 189 | TATA | 97.3 ± 3.33 | | | |
| 26 | ACVPDERCAFMNVCEDR | 190 | TATA | 39.05 ± 10.29 | | | |
| 27 | ACVPDRRCAFQDVCDHE | 191 | TATA | 159 n = 1 | | | |
| 28 | ACVPDRRCAFRDVCLTG | 192 | TATA | 1700 n = 1 | | | |
| 29 | ACYVGKECAYMNVCA | 193 | TATA | 209.5 ± 110.74 | 106.65 ± 24.94 | 87.7 n = 1 | |
| 30 | ACQPSNHCAFMNYCA | 194 | TATA | 293 n = 1 | 186.53 ± 86.86 | 137 n = 1 | |
| 31 | ACSPTPACAVQNLCA | 195 | TATA | 223 n = 1 | 177 ± 60.76 | | |
| 32 | ACTSCWAYPDSFCA | 196 | TATA | 232 ± 52.19 | | 151 n = 1 | |
| 33 | ACTKPTGFCAYPDTICA | 197 | TATA | 268.5 ± 16.66 | | | |
| 34 | ACRGEWGYCAYPDTICA | 198 | TATA | 347.5 ± 57.82 | | | |
| 35 | ACRNWGMYCAYPDTICA | 199 | TATA | 282.5 ± 65.66 | | | |
| 36 | ACPDWGKYCAYPDTICA | 200 | TATA | 160 ± 1.96 | | | |
| 37 | ACRVYGPYCAYPDTICA | 201 | TATA | 294.5 ± 20.58 | | | |
| 38 | ACSSCWAYPDSVCA | 202 | TATA | 400.33 ± 205.19 | | | |
| 39 | ACQSCWAYPDTYCA | 203 | TATA | 321.33 ± 119.53 | | | |
| 40 | ACGFMGLEPCETFCA | 204 | TATA | 187.5 ± 20.58 | | | |
| 41 | ACGFMGLVPCEVHCA | 205 | TATA | 155 ± 9.8 | | | |
| 42 | ACGFMGLEPCEMVCA | 206 | TATA | 320.5 ± 14.7 | | | |
| 43 | ACGFMGLEPCVTYCA | 207 | TATA | 233.5 ± 20.58 | | | |
| 44 | ACGFMGLEPCELVCA | 208 | TATA | 126.8 ± 21.17 | | | |
| 45 | ACGFMGLVPCNVFCA | 209 | TATA | 142 ± 41.16 | | | |
| 46 | ACGFMGLEPCELFCA | 210 | TATA | 81.7 ± 7.06 | | | |
| 47 | ACGFMGLEPCELFCMPK | 211 | TATA | 185 ± 74.48 | | | |
| 48 | ACGFMGLEPCELYCA | 212 | TATA | 127.5 ± 14.7 | | | |
| 49 | ACGFMGLEPCELYCAHT | 213 | TATA | 144 ± 17.64 | | | |
| 50 | ACGFMGLEPCEMYCA | 214 | TATA | 140 ± 45.08 | | | |
| 51 | ACGFMGLVPCELYCADN | 215 | TATA | 84.4 ± 36.46 | | | |
| 52 | ACPLVNPLCLTSGWKCA | 216 | TATA | 115.33 ± 11.33 | | | |
| 53 | ACPMVNPLCLHPGWICA | 217 | TATA | 15.4 ± 3.17 | | | |
| 54 | ACPLVNPLCLHPGWICA | 218 | TATA | 15.25 ± 2.84 | | | |
| 55 | ACPLVNPLCLHPGWRCA | 219 | TATA | 20.55 ± 0.88 | | | |
| 56 | ACPLVNPLCNLPGWTCA | 220 | TATA | 184 ± 115.64 | | | |
| 57 | ACPLVNPLCLVPGWSCA | 221 | TATA | 35.4 ± 10 | | | |
| 58 | ACPLVNPLCLLDGWTCA | 222 | TATA | 38.35 ± 5.39 | | | |
| 59 | ACPLVNPLCLMPGWGCA | 223 | TATA | 114.5 ± 10.78 | | | |
| 60 | ACPLVNPLCMIGNWTCA | 224 | TATA | 96.2 ± 0.59 | | | |
| 61 | ACPLVNPLCLMTGWSCA | 225 | TATA | 241.5 ± 44.1 | | | |
| 62 | ACPLVNPLCMMGGWKCA | 226 | TATA | 67.1 ± 19.21 | | | |
| 63 | ACPLVNPLCLYGSWKCA | 227 | TATA | 59.05 ± 28.32 | | | |
| 64 | ACPLVNPLCLHPGWTCA | 228 | TATA | 30 n = 1 | | | |

TABLE 12-continued

Biological Assay Data for Peptide Ligands of the Invention (TATA peptides, Competition Binding Assay)

| | | | | Ki, nM ± 95% CI | | | |
|---|---|---|---|---|---|---|---|
| | | | | Fluorescent Peptide | | | |
| | | | | Human EphA2 | | | Mouse EphA2 |
| Bicycle Compound Number | Sequence | SEQ ID NO: | Scaffold | Reference Compound C | Reference Compound B | Reference Compound A | Reference Compound C |
| 65 | ARDCPLVNPLCLHPGWTCA | 229 | TATA | 6.05 ± 1.38 | | | 39.1 ± 0.39 |
| 66 (BCY6099) | (β-Ala)-Sar$_{10}$-ARDCPLVNPLCLHPGWTC | 230 | TATA | 4.94 ± 1.41 | | | 57.6 ± 24.86 |
| 67 (BCY6014) | (β-Ala)-Sar$_{10}$-A(HArg)DCPLVNPLCLHPGWTC | 231 | TATA | 8.51 ± 0.17 | | | 61.7 ± 15.48 |
| 68 | Ac-ARDCPLVNPLCLHPGWTCA-Sar$_6$-(D-K) | | TATA | 19.3 ± 4.92 | | | 166.5 ± 30.38 |
| 69 | Ac-A(HArg)DCPLVNPLCLHPGWTCA-Sar$_6$-(D-K) | | TATA | 17.5 ± 0.98 | | | 164.5 ± 2.94 |
| 70 | RPACPLVNPLCLHPGWTCA | 232 | TATA | 10.06 ± 2.96 | | | |
| 71 | RPPCPLVNPLCLHPGWTCA | 233 | TATA | 11.11 ± 2.25 | | | |
| 72 | KHSCPLVNPLCLHPGWTCA | 234 | TATA | 11.92 ± 6.04 | | | |
| 73 | ACPLVNPLCLHPGWTCLHG | 235 | TATA | 1.98 ± 0.49 | | | 7.27 ± 1.09 |
| 74 | Ac-CPLVNPLCLHPGWTCLHG | 236 | TATA | 1.76 ± 0.54 | | | |
| 75 | (β-Ala)-Sar$_{10}$-ACPLVNPLCLHPGWTCLHG | 237 | TATA | 2.48 ± 0.27 | | | 18 ± 1.18 |
| 76 | (β-Ala)-Sar$_{10}$-ACPLVNPLCLHPGWTCL(D-His)G | | TATA | 10.01 ± 1.55 | | | 75.15 ± 14.41 |
| 77 (BCY6019) | Ac-CPLVNPLCLHPGWTCLHG-Sar$_6$-(D-K) | | TATA | 5.41 ± 0.86 | | | 48.23 ± 15.72 |
| 78 | Ac-CPLVNPLCLHPGWTCL(D-His)G-Sar$_6$-(D-K) | | TATA | 15.6 ± 4.7 | | | 115.03 ± 41.16 |
| 79 | ACPLVNPLCLHPG(2Nal)TCLHG | 238 | TATA | 162 ± 17.64 | | | |
| 80 | RHDCPLVNPLCLLPGWTCA | 239 | TATA | 7.11 ± 0.72 | | | |
| 81 | TPRCPLVNPLCLMPGWTCA | 240 | TATA | 9.8 ± 2.61 | | | |
| 82 | ACPLVNPLCLAPGWTCA | 241 | TATA | 46.2 n = 1 | | | |
| 83 | ACPLVNPLCLAPGWTCSRS | 242 | TATA | 7.05 ± 1.11 | | | |
| 84 | ACPLVNPLCLEPGWTCA | 243 | TATA | 53.9 n = 1 | | | |
| 85 | ACPLVNPLCLEPGWTCAKR | 244 | TATA | 10.95 ± 1.6 | | | |
| 86 | ACPLVNPLCLHPGWSCA | 245 | TATA | 56.15 ± 11.27 | | | |
| 87 (BCY6026) | ACPLVNPLCLHPGWSCRGQ | 246 | TATA | 2.57 ± 0.63 | | | 18.6 ± 0.59 |
| 88 | Ac-CPLVNPLCLHPGWSCRGQ | 247 | TATA | 1.64 ± 0.75 | | | |
| 89 | (β-Ala)-Sar$_{10}$-ACPLVNPLCLHPGWSCRGQ | 248 | TATA | 2.86 ± 1.29 | | | 29.55 ± 4.61 |
| 90 | (β-Ala)-Sar$_{10}$-ACPLVNPLCLHPGWSC(HArg)GQ | 249 | TATA | 5.41 ± 0.67 | | | 47.05 ± 11.47 |
| 91 (BCY6042) | Ac-CPLVNPLCLHPGWSCRGQ-Sar$_6$-(D-K) | | TATA | 5.98 ± 1.42 | | | 49.87 ± 14.44 |
| 92 | Ac-CPLVNPLCLHPGWSC(HArg)GQ-Sar$_6$-(D-K) | | TATA | 10.56 ± 6.56 | | | 75.27 ± 21.72 |
| 93 | ACPLVNPLCLHPG(2Nal)SCRGQ | 250 | TATA | 228 ± 103.88 | | | |
| 94 | ACPLVNPLCLTPGWTCTNT | 251 | TATA | 13.25 ± 4.05 | | | |
| 95 | ACPMVNPLCLHPGWKCA | 252 | TATA | 11.91 ± 3.73 | | | |
| 96 | ACPMVNPLCLTPGWICA | 253 | TATA | 16.07 ± 4.58 | | | |
| 97 | ACPMVNPLCLHPGWTCA | 254 | TATA | 20 ± 1.02 | | | |

TABLE 13

Biological Assay Data for Peptide Ligands of the Invention (Competition Binding Assay)

| Bicycle Compound Number | Sequence | Scaffold | Human EphA2 Reference Compound C |
|---|---|---|---|
| 98 | (β-Ala)-Sar$_{10}$-H(D-Asp)VT-C(Aib)(1Nal)G(Aib)F(1Nal)CP(tBuGly)N(HArg)P(D-Asp)C | TATA | 251.5 ± 73.5 |

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A peptide ligand specific for EphA2 comprising a polypeptide comprising a sequence:
[β-Ala][Sar]$_{10}$H[dD]VPA$_1$PWGPFWA$_2$PVNRPGA$_3$; or
[β-Ala][Sar]$_{10}$H[dD]VPA$_1$[Aib][1Nal]G[Aib]F[1Nal]A$_2$P[tBuGly]N[HArg]P[dD]A$_3$;
wherein A$_1$, A$_2$, and A$_3$ each represent independently a residue selected from the group consisting of cysteine, L-2,3-diaminopropionic acid (Dap), N-beta-alkyl-L-2,3-diaminopropionic acid (N-AlkDap), and N-beta-haloalkyl-L-2,3-diaminopropionic acid (N-HAlkDap), with the proviso that at least one of the A$_1$, A$_2$, and A$_3$ is selected from the group consisting of Dap, N-Alk-Dap, and N-HAlkDap, the A$_1$, A$_2$, and A$_3$ residues being separated by at least two loop sequences, and a molecular scaffold, the peptide being linked to the scaffold by covalent alkylamino linkages with the Dap or N-AlkDap or N-HAlkDap residues of the polypeptide and by thioether linkages with the cysteine residues of the polypeptide when the said three residues include cysteine, such that two polypeptide loops are formed on the molecular scaffold;
wherein Aib represents aminoisobutyric acid, 1Nal represents 1-naphthylalanine, tBuGly represents tert-leucine, Sar represents sarcosine, HArg represents homoarginine, and dD represents D-aspartic acid.

2. The peptide ligand as defined in claim 1, wherein two of A$_1$, A$_2$ and A$_3$ are selected from the group consisting of Dap, N-AlkDap, and N-HAlkDap, and the third one of A$_1$, A$_2$ and A$_3$ is cysteine.

3. The peptide ligand as defined in claim 1, wherein A$_1$, A$_2$ and A$_3$ are each N-AlkDap or N-HAlkDap.

4. The peptide ligand as defined in claim 1, wherein the molecular scaffold is an aromatic molecular scaffold.

5. The peptide ligand as defined in claim 4, wherein the peptide ligand comprises an amino acid sequence selected from the group consisting of:
AF488-(β-Ala)-Sar$_{10}$-H(D-Asp)VPCPWGPFWCPVNRPGCA; and
(β-Ala)-Sar$_{10}$-H(D-Asp)VP-CPWGPFWCPVNRPGC,
or a pharmaceutically acceptable salt thereof, with the proviso that one or more of the cysteine residues in said amino acid sequence is replaced by Dap, N-AlkDap or N-HAlkDap.

6. The peptide ligand as defined in claim 4, wherein the aromatic molecular scaffold is 1,3,5-tris(methylene)benzene.

7. The peptide ligand as defined in claim 1, wherein A$_2$ is cysteine and A$_1$ and A$_3$ are each independently Dap, N-Alk-Dap or N-HAlkDap.

8. The peptide ligand as defined in claim 7, wherein A$_1$ and A$_3$ are Dap.

9. The peptide ligand as defined in claim 1, wherein the molecular scaffold is a non-aromatic molecular scaffold.

10. The peptide ligand as defined in claim 9, wherein the non-aromatic molecular scaffold is 1,1',1"-(1,3,5-triazinane-1,3,5-triyl)triprop-2-en-1-one (TATA).

11. The peptide ligand as defined in claim 1, wherein the EphA2 is human EphA2.

12. The peptide ligand as defined in claim 1, wherein the peptide ligand is selective for human EphA2, but does not cross-react with human EphA1, EphA3 or EphA4.

13. The peptide ligand as defined in claim 1, wherein one of A$_1$, A$_2$ and A$_3$ is selected from the group consisting of Dap, N-AlkDap, and N-HAlkDap.

14. The peptide ligand as defined in claim 1, wherein the peptide ligand comprises an amino acid sequence selected from the group consisting of:
[β-Ala][Sar]$_{10}$H[dD]VP[Dap]PWGPFW[Dap]PVNRPGC;
[β-Ala][Sar]$_{10}$H[dD]VPCPWGPFW[Dap]PVNRPG[Dap];
[β-Ala][Sar]$_{10}$H[dD]VP[Dap]PWGPFWCPVNRPG[Dap];
[β-Ala][Sar]$_{10}$H[dD]VP[Dap][Aib][1Nal]G[Aib]F[1Nal][Dap]P[tBuGly]N[HArg]P[dD]C;
[β-Ala][Sar]$_{10}$H[dD]VPC[Aib][1Nal]G[Aib]F [1Nal][Dap]P[tBuGly]N[HArg]P[dD][Dap]; and
[β-Ala][Sar]$_{10}$H[dD]VP [Dap][Aib][1Nal]G[Aib]F[1Nal]CP[tBuGly]N[HArg]P [dD][Dap],
or a pharmaceutically acceptable salt thereof.

15. A drug conjugate comprising a peptide ligand as defined in claim 1, conjugated to one or more effector and/or functional groups.

16. The drug conjugate as defined in claim 15, wherein said effector and/or functional groups comprise a cytotoxic agent selected from the group consisting of DM1 and MMAE.

17. The drug conjugate as defined in claim 16, wherein the cytotoxic agent is MMAE.

18. A pharmaceutical composition which comprises the drug conjugate of claim 15, in combination with one or more pharmaceutically acceptable excipients.

19. A pharmaceutical composition which comprises the peptide ligand of claim 1, in combination with one or more pharmaceutically acceptable excipients.

* * * * *

SEQUENCE LISTING

<160> NUMBER OF SEQ ID NOS: 254

<210> SEQ ID NO 1
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(11)
<223> OTHER INFORMATION: Sarcosine

<400> SEQUENCE: 1

Gly Xaa Xaa Xaa Xaa Xaa Xaa Xaa Xaa Xaa Xaa Ala
1               5                   10

<210> SEQ ID NO 2
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 2

Xaa Xaa Xaa Xaa Xaa Xaa Xaa Xaa Xaa Xaa Xaa Ala
1               5                   10

<210> SEQ ID NO 3
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 3

Ala Cys Met Asn Asp Trp Leu Cys Ser Leu Gly Trp Thr Cys Ala Xaa
1               5                   10                  15

Xaa Xaa Xaa Xaa Xaa Lys
            20

<210> SEQ ID NO 4
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(11)
<223> OTHER INFORMATION: Sarcosine

```
<400> SEQUENCE: 4

Gly Xaa Xaa Xaa Xaa Xaa Xaa Xaa Xaa Xaa Ala Cys Met Asn Asp
1               5                   10                  15

Trp Leu Cys Ser Leu Gly Trp Thr Cys
            20                  25

<210> SEQ ID NO 5
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 5

Ala Cys Met Asn Asp Trp Leu Cys Glu Leu Gly Trp Thr Cys Ala Xaa
1               5                   10                  15

Xaa Xaa Xaa Xaa Xaa Lys
            20

<210> SEQ ID NO 6
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (18)..(23)
<223> OTHER INFORMATION: Sarcosine

<400> SEQUENCE: 6

Ala Cys Thr Arg Gln Gly Ile Trp Cys Ala Leu Gly Phe Glu Pro Cys
1               5                   10                  15

Ala Xaa Xaa Xaa Xaa Xaa Xaa Lys
            20

<210> SEQ ID NO 7
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 7

Ala Cys Met Asn Asp Trp Leu Cys Thr Leu Gly Trp Ser Cys Ala Xaa
1               5                   10                  15

Xaa Xaa Xaa Xaa Xaa Lys
            20

<210> SEQ ID NO 8
<211> LENGTH: 22
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 8

Ala Cys Met Asn Asp Trp Leu Cys Gln Leu Gly Trp Thr Cys Ala Xaa
1               5                   10                  15

Xaa Xaa Xaa Xaa Xaa Lys
            20

<210> SEQ ID NO 9
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 9

Ala Cys Met Asn Asp Trp Leu Cys Thr Leu Gly Trp Thr Cys Ala Xaa
1               5                   10                  15

Xaa Xaa Xaa Xaa Xaa Lys
            20

<210> SEQ ID NO 10
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 10

Ala Cys Met Asn Asp Trp Leu Cys Asp Leu Gly Trp Arg Cys Ala Xaa
1               5                   10                  15

Xaa Xaa Xaa Xaa Xaa Lys
            20

<210> SEQ ID NO 11
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 11

Ala Cys Met Asn Asp Trp Leu Cys Glu Leu Gly Trp Ser Cys Ala Xaa
```

```
1               5                   10                  15

Xaa Xaa Xaa Xaa Xaa Lys
            20

<210> SEQ ID NO 12
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (22)..(27)
<223> OTHER INFORMATION: Sarcosine

<400> SEQUENCE: 12

Ala Cys Arg Val Ser Pro Glu Tyr Cys Pro Phe Gly Pro Val Trp Cys
1               5                   10                  15

Ala Gly Ala Ala Ala Xaa Xaa Xaa Xaa Xaa Xaa Lys
            20                  25

<210> SEQ ID NO 13
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 13

Gly Xaa Xaa Xaa Xaa Xaa Ala Cys Pro Trp Gly Pro Ala Trp Cys Pro
1               5                   10                  15

Val His Gly Lys Thr Cys Ala
            20

<210> SEQ ID NO 14
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 14

Gly Xaa Xaa Xaa Xaa Xaa Ala Cys Pro Trp Gly Pro Ala Trp Cys Pro
1               5                   10                  15

Val Asn Arg Pro Gly Cys Ala
            20

<210> SEQ ID NO 15
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic peptide"

<400> SEQUENCE: 15

Ala Cys Pro Trp Gly Pro Ala Trp Cys Pro Val Asn Arg Pro Gly Cys
1               5                   10                  15

Ala Gly Ala Ala Ala Lys
            20

<210> SEQ ID NO 16
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(11)
<223> OTHER INFORMATION: Sarcosine

<400> SEQUENCE: 16

Gly Xaa Xaa Xaa Xaa Xaa Xaa Xaa Xaa Xaa Xaa Ala Cys Pro Trp Gly
1               5                   10                  15

Pro Ala Trp Cys Pro Val Asn Arg Pro Gly Cys Ala
            20                  25

<210> SEQ ID NO 17
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 17

Gly Xaa Xaa Xaa Xaa Xaa Ala Cys Pro Trp Gly Pro Met Trp Cys Pro
1               5                   10                  15

Val Asn Arg Pro Gly Cys Ala
            20

<210> SEQ ID NO 18
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 18

Gly Xaa Xaa Xaa Xaa Xaa Ala Cys Pro Trp Gly Pro Asn Trp Cys Pro
1               5                   10                  15

Val Asn Arg Pro Gly Cys Ala
            20

<210> SEQ ID NO 19
<211> LENGTH: 27

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 19

Gly Xaa Xaa Xaa Xaa Xaa Ala Gly Glu Met Ala Cys Pro Trp Gly Pro
1               5                   10                  15

Phe Trp Cys Pro Val Asn Arg Pro Gly Cys Ala
            20                  25

<210> SEQ ID NO 20
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 20

Gly Xaa Xaa Xaa Xaa Xaa Ala Asp Val Thr Cys Pro Trp Gly Pro Phe
1               5                   10                  15

Trp Cys Pro Val Asn Arg Pro Gly Cys Ala
            20                  25

<210> SEQ ID NO 21
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 21

Gly Xaa Xaa Xaa Xaa Xaa Ala Asp Val Arg Thr Cys Pro Trp Gly Pro
1               5                   10                  15

Phe Trp Cys Pro Val Asn Arg Pro Gly Cys Ala
            20                  25

<210> SEQ ID NO 22
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 22
```

```
Gly Xaa Xaa Xaa Xaa Xaa Ala Asn Asp Val Thr Cys Pro Trp Gly Pro
1               5                   10                  15

Phe Trp Cys Pro Val Asn Arg Pro Gly Cys Ala
            20                  25
```

<210> SEQ ID NO 23
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (18)..(23)
<223> OTHER INFORMATION: Sarcosine

<400> SEQUENCE: 23

```
Ala Cys Val Pro Gln Gly Ile Trp Cys Ala Leu Gln Phe Glu Pro Cys
1               5                   10                  15

Ala Xaa Xaa Xaa Xaa Xaa Xaa Lys
            20
```

<210> SEQ ID NO 24
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (18)..(23)
<223> OTHER INFORMATION: Sarcosine

<400> SEQUENCE: 24

```
Ala Cys Gln Lys Gln Gly Leu Trp Cys Ala Leu Gly Phe Glu Pro Cys
1               5                   10                  15

Ala Xaa Xaa Xaa Xaa Xaa Xaa Lys
            20
```

<210> SEQ ID NO 25
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 25

```
Ala Cys Leu Val Asn Asp Asp Cys Phe Tyr Met Gly Leu Cys Ala Xaa
1               5                   10                  15

Xaa Xaa Xaa Xaa Xaa Lys
            20
```

<210> SEQ ID NO 26
<211> LENGTH: 15
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 26

Ala Cys Met Asn Asp Trp Leu Cys Ser Leu Gly Trp Thr Cys Ala
1               5                   10                  15

<210> SEQ ID NO 27
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Cys Ala Asn Asp Trp Leu Cys Ser Leu Gly Trp Thr Cys
1               5                   10

<210> SEQ ID NO 28
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Cys Met Asn Asp Trp Leu Cys Ala Leu Gly Trp Thr Cys
1               5                   10

<210> SEQ ID NO 29
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Cys Met Asn Asp Trp Leu Cys Ser Ala Gly Trp Thr Cys
1               5                   10

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ala Cys Met Asn Asp Trp Leu Cys Gln Leu Gly Trp Lys Cys Ala
1               5                   10                  15

<210> SEQ ID NO 31
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31
```

```
Ala Cys Met Asn Asp Trp Leu Cys Glu Leu Gly Trp Thr Cys Ala
1               5                   10                  15
```

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

```
Ala Cys Met Asn Asp Trp Leu Cys Gln Leu Gly Trp Thr Cys Ala
1               5                   10                  15
```

<210> SEQ ID NO 33
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

```
Ala Cys Thr Gln Asn Asp Trp Leu Cys Ser Leu Gly Trp Thr Cys Ala
1               5                   10                  15
```

<210> SEQ ID NO 34
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

```
Ala Cys Arg Asn Ile Pro Thr Met Cys Pro Phe Gly Pro Val Trp Cys
1               5                   10                  15
Ala
```

<210> SEQ ID NO 35
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

```
Ala Cys Arg Val Ser Pro Glu Tyr Cys Pro Phe Gly Pro Val Trp Cys
1               5                   10                  15
Ala
```

<210> SEQ ID NO 36
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

```
Ala Cys Arg Val Ser Pro Glu Tyr Cys Pro Phe Gly Pro Val Trp Cys
1               5                   10                  15

Ala Gly Ala Ala Ala
            20
```

<210> SEQ ID NO 37
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

```
Ala Cys Arg Val Ser Pro Glu Tyr Cys Pro Phe Gly Pro Thr Trp Cys
1               5                   10                  15

Ala
```

<210> SEQ ID NO 38
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

```
Ala Cys Arg Val Ser Pro Glu Tyr Cys Pro Phe Gly Pro Ser Trp Cys
1               5                   10                  15

Ala
```

<210> SEQ ID NO 39
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

```
Ala Cys Arg Val Ser Pro Glu Tyr Cys Pro Phe Gly Pro Glu Trp Cys
1               5                   10                  15

Ala
```

<210> SEQ ID NO 40
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

```
Ala Cys Arg Val Ser Pro Glu Tyr Cys Pro Phe Gly Pro Tyr Trp Cys
1               5                   10                  15

Ala
```

<210> SEQ ID NO 41
<211> LENGTH: 17
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ala Cys Arg Val Ser Pro Glu Tyr Cys Pro Phe Gly Pro Leu Trp Cys
1               5                   10                  15
Ala

<210> SEQ ID NO 42
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ala Cys Arg Val Ser Pro Glu Tyr Cys Pro Phe Gly Pro Asp Trp Cys
1               5                   10                  15
Ala

<210> SEQ ID NO 43
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ala Cys Pro Trp Gly Pro Ala Trp Cys Pro Val His Gly Lys Thr Cys
1               5                   10                  15
Ala

<210> SEQ ID NO 44
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ala Cys Pro Trp Gly Pro Ala Trp Cys Pro Val Arg Asp Thr Asn Cys
1               5                   10                  15
Ala

<210> SEQ ID NO 45
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ala Cys Pro Trp Gly Pro Ala Trp Cys Pro Val Asn Gly Ala Arg Cys
1               5                   10                  15
```

Ala

```
<210> SEQ ID NO 46
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ala Cys Pro Trp Gly Pro Ala Trp Cys Pro Val Asn Arg Pro Gly Cys
1               5                   10                  15

Ala

<210> SEQ ID NO 47
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Cys Pro Trp Gly Pro Ala Trp Cys Pro Val Asn Arg Pro Gly Cys
1               5                   10                  15

Ala Gly Ala Ala Ala
            20

<210> SEQ ID NO 48
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Ala Cys Pro Trp Gly Pro Met Trp Cys Pro Val Asn Arg Pro Gly Cys
1               5                   10                  15

Ala

<210> SEQ ID NO 49
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ala Cys Pro Trp Gly Pro Asn Trp Cys Pro Val Asn Arg Pro Gly Cys
1               5                   10                  15

Ala

<210> SEQ ID NO 50
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 50

Ala Cys Pro Trp Gly Pro Ala Trp Cys Pro Val Arg Asn Pro Cys Ala
1               5                   10                  15

<210> SEQ ID NO 51
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ala Cys Pro Trp Gly Pro Ala Trp Cys Pro Val Ser Arg Val Cys Ala
1               5                   10                  15

<210> SEQ ID NO 52
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ala Cys Pro Trp Gly Pro Ala Trp Cys Pro Val Arg Ser Cys Ala
1               5                   10                  15

<210> SEQ ID NO 53
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ala Cys Pro Trp Gly Pro Ala Trp Cys Pro Val Lys Pro Thr Cys Ala
1               5                   10                  15

<210> SEQ ID NO 54
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ala Cys Pro Trp Gly Pro Ala Trp Cys Pro Val Asn Arg Asn Gly Cys
1               5                   10                  15

Ala

<210> SEQ ID NO 55
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 55

Ala Gly Glu Met Ala Cys Pro Trp Gly Pro Phe Trp Cys Pro Val Asn
1               5                   10                  15

Arg Pro Gly Cys Ala
            20

<210> SEQ ID NO 56
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ala Val His Ile Pro Cys Pro Trp Gly Pro Ser Trp Cys Pro Val Asn
1               5                   10                  15

Arg Pro Gly Cys Ala
            20

<210> SEQ ID NO 57
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ala Glu Gly Leu Pro Cys Pro Trp Gly Pro Phe Trp Cys Pro Val Asn
1               5                   10                  15

Arg Pro Gly Cys Ala
            20

<210> SEQ ID NO 58
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ala Asp His Ala Cys Pro Trp Gly Pro Phe Trp Cys Pro Val Asn Arg
1               5                   10                  15

Pro Gly Cys Ala
            20

<210> SEQ ID NO 59
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ala Asp Val His Cys Pro Trp Gly Pro Phe Trp Cys Pro Val Asn Arg
1               5                   10                  15

Pro Gly Cys Ala
            20
```

<210> SEQ ID NO 60
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ala Asp Val Thr Cys Pro Trp Gly Pro Phe Trp Cys Pro Val Asn Arg
1               5                   10                  15

Pro Gly Cys Ala
            20

<210> SEQ ID NO 61
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ala His Asp Val Pro Cys Pro Trp Gly Pro Phe Trp Cys Pro Val Asn
1               5                   10                  15

Arg Pro Gly Cys Ala
            20

<210> SEQ ID NO 62
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ala Asp Val Arg Thr Cys Pro Trp Gly Pro Phe Trp Cys Pro Val Asn
1               5                   10                  15

Arg Pro Gly Cys Ala
            20

<210> SEQ ID NO 63
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ala Asn Asp Val Thr Cys Pro Trp Gly Pro Phe Trp Cys Pro Val Asn
1               5                   10                  15

Arg Pro Gly Cys Ala
            20

<210> SEQ ID NO 64
<211> LENGTH: 21
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 64

Ala Arg Asp Asp Pro Cys Pro Trp Gly Pro Phe Trp Cys Pro Val Asn
1               5                   10                  15

Arg Pro Gly Cys Ala
            20

<210> SEQ ID NO 65
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ala Cys Val Pro Gln Gly Ile Trp Cys Ala Leu Gln Phe Glu Pro Cys
1               5                   10                  15

Ala

<210> SEQ ID NO 66
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Ala Cys Thr Thr Gly Ser Ile Trp Cys Ala Leu Gln Phe Glu Pro Cys
1               5                   10                  15

Ala

<210> SEQ ID NO 67
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ala Cys Val Pro Gln Gly Ile Trp Cys Ala Leu Arg Tyr Glu Pro Cys
1               5                   10                  15

Ala

<210> SEQ ID NO 68
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 68
```

```
Gly Xaa Xaa Xaa Xaa Xaa Ala Cys Pro Trp Gly Pro Phe Trp Cys Pro
1               5                   10                  15

Val Asn Arg Pro Gly Cys Ala
            20
```

```
<210> SEQ ID NO 69
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 69

Gly Xaa Xaa Xaa Xaa Xaa Ala Cys Pro Trp Gly Pro Phe Trp Cys Pro
1               5                   10                  15

Val Asn Arg Pro Gly Cys
            20
```

```
<210> SEQ ID NO 70
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 70

Xaa Xaa Xaa Xaa Xaa Xaa Xaa Xaa Xaa Xaa Xaa Ala Cys Pro Trp Gly
1               5                   10                  15

Pro Phe Trp Cys Pro Val Asn Arg Pro Gly Cys
            20                  25
```

```
<210> SEQ ID NO 71
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ala Cys Pro Trp Gly Pro Phe Trp Cys Pro Val Asn Arg Pro Gly Cys
1               5                   10                  15

Ala
```

```
<210> SEQ ID NO 72
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                            Synthetic peptide"
<220> FEATURE:
<221> NAME/KEY: MOD_RES
<222> LOCATION: (1)..(2)
<223> OTHER INFORMATION: Sarcosine

<400> SEQUENCE: 72

Xaa Xaa Ala Cys Pro Trp Gly Pro Phe Trp Cys Pro Val Asn Arg Pro
1               5                   10                  15

Gly Cys

<210> SEQ ID NO 73
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 73

Xaa Xaa Ala Cys Pro Trp Gly Pro Phe Trp Cys Pro Val Asn Arg Pro
1               5                   10                  15

Gly Cys

<210> SEQ ID NO 74
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 74

Xaa Xaa Xaa Xaa Xaa Xaa Xaa Xaa Xaa Xaa Xaa Ala Cys Pro Trp Gly
1               5                   10                  15

Pro Phe Trp Cys Pro Val Asn Arg Pro Gly Cys
            20                  25

<210> SEQ ID NO 75
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (5)..(5)
<223> OTHER INFORMATION: Hydroxyproline

<400> SEQUENCE: 75
```

```
Xaa Xaa Ala Cys Xaa Trp Gly Pro Phe Trp Cys Pro Val Asn Arg Pro
1               5                   10                  15

Gly Cys

<210> SEQ ID NO 76
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (5)..(5)
<223> OTHER INFORMATION: 2-Aminoisobutyric acid

<400> SEQUENCE: 76

Xaa Xaa Ala Cys Xaa Trp Gly Pro Phe Trp Cys Pro Val Asn Arg Pro
1               5                   10                  15

Gly Cys

<210> SEQ ID NO 77
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (5)..(5)
<223> OTHER INFORMATION: 4-Fluoro-pyrrolidine-2-carboxylic acid

<400> SEQUENCE: 77

Xaa Xaa Ala Cys Xaa Trp Gly Pro Phe Trp Cys Pro Val Asn Arg Pro
1               5                   10                  15

Gly Cys

<210> SEQ ID NO 78
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine

<400> SEQUENCE: 78

Xaa Xaa Ala Cys Pro Xaa Gly Pro Phe Trp Cys Pro Val Asn Arg Pro
1               5                   10                  15
```

Gly Cys

<210> SEQ ID NO 79
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 2-Naphthylalanine

<400> SEQUENCE: 79

Xaa Xaa Ala Cys Pro Xaa Gly Pro Phe Trp Cys Pro Val Asn Arg Pro
1               5                   10                  15

Gly Cys

<210> SEQ ID NO 80
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (8)..(8)
<223> OTHER INFORMATION: Azetidine

<400> SEQUENCE: 80

Xaa Xaa Ala Cys Pro Trp Gly Xaa Phe Trp Cys Pro Val Asn Arg Pro
1               5                   10                  15

Gly Cys

<210> SEQ ID NO 81
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (8)..(8)
<223> OTHER INFORMATION: Hydroxyproline

<400> SEQUENCE: 81

Xaa Xaa Ala Cys Pro Trp Gly Xaa Phe Trp Cys Pro Val Asn Arg Pro
1               5                   10                  15

Gly Cys

<210> SEQ ID NO 82

```
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (8)..(8)
<223> OTHER INFORMATION: 2-Aminoisobutyric acid

<400> SEQUENCE: 82

Xaa Xaa Ala Cys Pro Trp Gly Xaa Phe Trp Cys Pro Val Asn Arg Pro
1               5                   10                  15

Gly Cys

<210> SEQ ID NO 83
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (8)..(8)
<223> OTHER INFORMATION: 4-Fluoro-pyrrolidine-2-carboxylic acid

<400> SEQUENCE: 83

Xaa Xaa Ala Cys Pro Trp Gly Xaa Phe Trp Cys Pro Val Asn Arg Pro
1               5                   10                  15

Gly Cys

<210> SEQ ID NO 84
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (8)..(8)
<223> OTHER INFORMATION: Pipecolic acid

<400> SEQUENCE: 84

Xaa Xaa Ala Cys Pro Trp Gly Xaa Phe Trp Cys Pro Val Asn Arg Pro
1               5                   10                  15

Gly Cys

<210> SEQ ID NO 85
<211> LENGTH: 18
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 85

Xaa Xaa Ala Cys Pro Trp Gly Pro Ala Trp Cys Pro Val Asn Arg Pro
1               5                   10                  15

Gly Cys

<210> SEQ ID NO 86
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: 3-(4-Pyridyl)-Alanine

<400> SEQUENCE: 86

Xaa Xaa Ala Cys Pro Trp Gly Pro Xaa Trp Cys Pro Val Asn Arg Pro
1               5                   10                  15

Gly Cys

<210> SEQ ID NO 87
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: 4-Bromophenylalanine

<400> SEQUENCE: 87

Xaa Xaa Ala Cys Pro Trp Gly Pro Xaa Trp Cys Pro Val Asn Arg Pro
1               5                   10                  15

Gly Cys

<210> SEQ ID NO 88
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
```

```
<221> NAME/KEY: MOD_RES
<222> LOCATION: (9)..(9)
<223> OTHER INFORMATION: 4-Methoxyphenylalanine

<400> SEQUENCE: 88

Xaa Xaa Ala Cys Pro Trp Gly Pro Xaa Trp Cys Pro Val Asn Arg Pro
1               5                  10                 15

Gly Cys

<210> SEQ ID NO 89
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: Homophenylalanine

<400> SEQUENCE: 89

Xaa Xaa Ala Cys Pro Trp Gly Pro Xaa Trp Cys Pro Val Asn Arg Pro
1               5                  10                 15

Gly Cys

<210> SEQ ID NO 90
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: 4,4'-Biphenylalanine

<400> SEQUENCE: 90

Xaa Xaa Ala Cys Pro Trp Gly Pro Xaa Trp Cys Pro Val Asn Arg Pro
1               5                  10                 15

Gly Cys

<210> SEQ ID NO 91
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: 4-Nitrophenylalanine
```

```
<400> SEQUENCE: 91

Xaa Xaa Ala Cys Pro Trp Gly Pro Xaa Trp Cys Pro Val Asn Arg Pro
1               5                   10                  15

Gly Cys

<210> SEQ ID NO 92
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: 3,4-Dichlorophenylalanine

<400> SEQUENCE: 92

Xaa Xaa Ala Cys Pro Trp Gly Pro Xaa Trp Cys Pro Val Asn Arg Pro
1               5                   10                  15

Gly Cys

<210> SEQ ID NO 93
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 93

Xaa Xaa Ala Cys Pro Trp Gly Pro Tyr Trp Cys Pro Val Asn Arg Pro
1               5                   10                  15

Gly Cys

<210> SEQ ID NO 94
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: 3-(3-Pyridyl)-Alanine

<400> SEQUENCE: 94

Xaa Xaa Ala Cys Pro Trp Gly Pro Xaa Trp Cys Pro Val Asn Arg Pro
1               5                   10                  15

Gly Cys
```

```
<210> SEQ ID NO 95
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: Phenylglycine

<400> SEQUENCE: 95

Xaa Xaa Ala Cys Pro Trp Gly Pro Xaa Trp Cys Pro Val Asn Arg Pro
1               5                   10                  15

Gly Cys

<210> SEQ ID NO 96
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: 1-Naphthylalanine

<400> SEQUENCE: 96

Xaa Xaa Ala Cys Pro Trp Gly Pro Xaa Trp Cys Pro Val Asn Arg Pro
1               5                   10                  15

Gly Cys

<210> SEQ ID NO 97
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (9)..(9)
<223> OTHER INFORMATION: 2-Naphthylalanine

<400> SEQUENCE: 97

Xaa Xaa Ala Cys Pro Trp Gly Pro Xaa Trp Cys Pro Val Asn Arg Pro
1               5                   10                  15

Gly Cys

<210> SEQ ID NO 98
<211> LENGTH: 18
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (10)..(10)
<223> OTHER INFORMATION: 1-Naphthylalanine

<400> SEQUENCE: 98

Xaa Xaa Ala Cys Pro Trp Gly Pro Phe Xaa Cys Pro Val Asn Arg Pro
1               5                   10                  15

Gly Cys

<210> SEQ ID NO 99
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (12)..(12)
<223> OTHER INFORMATION: Azetidine

<400> SEQUENCE: 99

Xaa Xaa Ala Cys Pro Trp Gly Pro Phe Trp Cys Xaa Val Asn Arg Pro
1               5                   10                  15

Gly Cys

<210> SEQ ID NO 100
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (12)..(12)
<223> OTHER INFORMATION: Hydroxyproline

<400> SEQUENCE: 100

Xaa Xaa Ala Cys Pro Trp Gly Pro Phe Trp Cys Xaa Val Asn Arg Pro
1               5                   10                  15

Gly Cys

<210> SEQ ID NO 101
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (12)..(12)
<223> OTHER INFORMATION: 4-Fluoro-pyrrolidine-2-carboxylic acid

<400> SEQUENCE: 101

Xaa Xaa Ala Cys Pro Trp Gly Pro Phe Trp Cys Xaa Val Asn Arg Pro
1               5                   10                  15

Gly Cys

<210> SEQ ID NO 102
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (13)..(13)
<223> OTHER INFORMATION: Tert-leucine

<400> SEQUENCE: 102

Xaa Xaa Ala Cys Pro Trp Gly Pro Phe Trp Cys Pro Xaa Asn Arg Pro
1               5                   10                  15

Gly Cys

<210> SEQ ID NO 103
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 103

Xaa Xaa Ala Cys Pro Trp Gly Pro Phe Trp Cys Pro Val Ala Arg Pro
1               5                   10                  15

Gly Cys

<210> SEQ ID NO 104
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (15)..(15)
<223> OTHER INFORMATION: Homoarginine
```

<400> SEQUENCE: 104

Xaa Xaa Ala Cys Pro Trp Gly Pro Phe Trp Cys Pro Val Asn Xaa Pro
1               5                   10                  15

Gly Cys

<210> SEQ ID NO 105
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 105

Xaa Xaa Ala Cys Pro Trp Gly Pro Phe Trp Cys Pro Val Asn Arg Ala
1               5                   10                  15

Gly Cys

<210> SEQ ID NO 106
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (16)..(16)
<223> OTHER INFORMATION: Azetidine

<400> SEQUENCE: 106

Xaa Xaa Ala Cys Pro Trp Gly Pro Phe Trp Cys Pro Val Asn Arg Xaa
1               5                   10                  15

Gly Cys

<210> SEQ ID NO 107
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (16)..(16)
<223> OTHER INFORMATION: Hydroxyproline

<400> SEQUENCE: 107

Xaa Xaa Ala Cys Pro Trp Gly Pro Phe Trp Cys Pro Val Asn Arg Xaa
1               5                   10                  15

Gly Cys

<210> SEQ ID NO 108
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (16)..(16)
<223> OTHER INFORMATION: Pipecolic acid

<400> SEQUENCE: 108

Xaa Xaa Ala Cys Pro Trp Gly Pro Phe Trp Cys Pro Val Asn Arg Xaa
1               5                   10                  15

Gly Cys

<210> SEQ ID NO 109
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (16)..(16)
<223> OTHER INFORMATION: 4-Fluoro-pyrrolidine-2-carboxylic acid

<400> SEQUENCE: 109

Xaa Xaa Ala Cys Pro Trp Gly Pro Phe Trp Cys Pro Val Asn Arg Xaa
1               5                   10                  15

Gly Cys

<210> SEQ ID NO 110
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (16)..(16)
<223> OTHER INFORMATION: 2-Aminoisobutyric acid

<400> SEQUENCE: 110

Xaa Xaa Ala Cys Pro Trp Gly Pro Phe Trp Cys Pro Val Asn Arg Xaa
1               5                   10                  15

Gly Cys

<210> SEQ ID NO 111
<211> LENGTH: 18
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 111

Xaa Xaa Ala Cys Pro Trp Gly Pro Phe Trp Cys Pro Val Asn Arg Pro
1               5                   10                  15
Ala Cys

<210> SEQ ID NO 112
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (5)..(5)
<223> OTHER INFORMATION: 2-Aminoisobutyric acid
<220> FEATURE:
<221> NAME/KEY: MOD_RES
<222> LOCATION: (6)..(6)
<223> OTHER INFORMATION: 1-Naphthylalanine

<400> SEQUENCE: 112

Xaa Xaa Ala Cys Xaa Xaa Gly Pro Phe Trp Cys Pro Val Asn Arg Pro
1               5                   10                  15
Gly Cys

<210> SEQ ID NO 113
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (5)..(5)
<223> OTHER INFORMATION: 2-Aminoisobutyric acid
<220> FEATURE:
<221> NAME/KEY: MOD_RES
<222> LOCATION: (10)..(10)
<223> OTHER INFORMATION: 1-Naphthylalanine

<400> SEQUENCE: 113

Xaa Xaa Ala Cys Xaa Trp Gly Pro Phe Xaa Cys Pro Val Asn Arg Pro
1               5                   10                  15
Gly Cys

<210> SEQ ID NO 114
<211> LENGTH: 18
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (8)..(8)
<223> OTHER INFORMATION: 2-Aminoisobutyric acid

<400> SEQUENCE: 114

Xaa Xaa Ala Cys Pro Xaa Gly Xaa Phe Trp Cys Pro Val Asn Arg Pro
1               5                   10                  15

Gly Cys

<210> SEQ ID NO 115
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (10)..(10)
<223> OTHER INFORMATION: 1-Naphthylalanine

<400> SEQUENCE: 115

Xaa Xaa Ala Cys Pro Xaa Gly Pro Phe Xaa Cys Pro Val Asn Arg Pro
1               5                   10                  15

Gly Cys

<210> SEQ ID NO 116
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (13)..(13)
<223> OTHER INFORMATION: Tert-leucine

<400> SEQUENCE: 116

Xaa Xaa Ala Cys Pro Xaa Gly Pro Phe Trp Cys Pro Xaa Asn Arg Pro

```
1               5                   10                  15

Gly Cys

<210> SEQ ID NO 117
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (15)..(15)
<223> OTHER INFORMATION: Homoarginine

<400> SEQUENCE: 117

Xaa Xaa Ala Cys Pro Xaa Gly Pro Phe Trp Cys Pro Val Asn Xaa Pro
1               5                   10                  15

Gly Cys

<210> SEQ ID NO 118
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (8)..(8)
<223> OTHER INFORMATION: 2-Aminoisobutyric acid
<220> FEATURE:
<221> NAME/KEY: MOD_RES
<222> LOCATION: (10)..(10)
<223> OTHER INFORMATION: 1-Naphthylalanine

<400> SEQUENCE: 118

Xaa Xaa Ala Cys Pro Trp Gly Xaa Phe Xaa Cys Pro Val Asn Arg Pro
1               5                   10                  15

Gly Cys

<210> SEQ ID NO 119
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
```

```
<220> FEATURE:
<221> NAME/KEY: MOD_RES
<222> LOCATION: (8)..(8)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Tert-leucine

<400> SEQUENCE: 119

Xaa Xaa Ala Cys Pro Xaa Gly Xaa Phe Trp Cys Pro Xaa Asn Arg Pro
1               5                   10                  15

Gly Cys

<210> SEQ ID NO 120
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (13)..(13)
<223> OTHER INFORMATION: Tert-leucine
<220> FEATURE:
<221> NAME/KEY: MOD_RES
<222> LOCATION: (15)..(15)
<223> OTHER INFORMATION: Homoarginine

<400> SEQUENCE: 120

Xaa Xaa Ala Cys Pro Xaa Gly Pro Phe Trp Cys Pro Xaa Asn Xaa Pro
1               5                   10                  15

Gly Cys

<210> SEQ ID NO 121
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (13)..(13)
<223> OTHER INFORMATION: Tert-leucine
<220> FEATURE:
<221> NAME/KEY: MOD_RES
<222> LOCATION: (16)..(16)
<223> OTHER INFORMATION: 2-Aminoisobutyric acid

<400> SEQUENCE: 121

Xaa Xaa Ala Cys Pro Xaa Gly Pro Phe Trp Cys Pro Xaa Asn Arg Xaa
1               5                   10                  15
```

Gly Cys

<210> SEQ ID NO 122
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (5)..(5)
<223> OTHER INFORMATION: 2-Aminoisobutyric acid
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (8)..(8)
<223> OTHER INFORMATION: 2-Aminoisobutyric acid
<220> FEATURE:
<221> NAME/KEY: MOD_RES
<222> LOCATION: (16)..(16)
<223> OTHER INFORMATION: 2-Aminoisobutyric acid

<400> SEQUENCE: 122

Xaa Xaa Ala Cys Xaa Xaa Gly Xaa Phe Trp Cys Pro Val Asn Arg Xaa
1               5                   10                  15

Gly Cys

<210> SEQ ID NO 123
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (8)..(8)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Tert-leucine
<220> FEATURE:
<221> NAME/KEY: MOD_RES
<222> LOCATION: (15)..(15)
<223> OTHER INFORMATION: Homoarginine

<400> SEQUENCE: 123

Xaa Xaa Ala Cys Pro Xaa Gly Xaa Phe Trp Cys Pro Xaa Asn Xaa Pro
1               5                   10                  15

Gly Cys

<210> SEQ ID NO 124

```
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (8)..(8)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Tert-leucine
<220> FEATURE:
<221> NAME/KEY: MOD_RES
<222> LOCATION: (16)..(16)
<223> OTHER INFORMATION: 2-Aminoisobutyric acid

<400> SEQUENCE: 124

Xaa Xaa Ala Cys Pro Xaa Gly Xaa Phe Trp Cys Pro Xaa Asn Arg Xaa
1               5                   10                  15

Gly Cys

<210> SEQ ID NO 125
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 1-Naphthylalanine
<220> FEATURE:
<221> NAME/KEY: MOD_RES
<222> LOCATION: (13)..(13)
<223> OTHER INFORMATION: Tert-leucine
<220> FEATURE:
<221> NAME/KEY: MOD_RES
<222> LOCATION: (15)..(15)
<223> OTHER INFORMATION: Homoarginine
<220> FEATURE:
<221> NAME/KEY: MOD_RES
<222> LOCATION: (16)..(16)
<223> OTHER INFORMATION: 2-Aminoisobutyric acid

<400> SEQUENCE: 125

Xaa Xaa Ala Cys Pro Xaa Gly Pro Phe Trp Cys Pro Xaa Asn Xaa Xaa
1               5                   10                  15

Gly Cys

<210> SEQ ID NO 126
<211> LENGTH: 21
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 126

Xaa Xaa Ala Asp Val His Cys Pro Trp Gly Pro Phe Trp Cys Pro Val
1               5                   10                  15

Asn Arg Pro Gly Cys
            20

<210> SEQ ID NO 127
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: 3,3-Diphenylalanine

<400> SEQUENCE: 127

Ala Asp Val His Cys Pro Xaa Gly Pro Phe Trp Cys Pro Val Asn Arg
1               5                   10                  15

Pro Gly Cys Ala
            20

<210> SEQ ID NO 128
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: 1-Naphthylalanine

<400> SEQUENCE: 128

Ala Asp Val His Cys Pro Xaa Gly Pro Phe Trp Cys Pro Val Asn Arg
1               5                   10                  15

Pro Gly Cys Ala
            20

<210> SEQ ID NO 129
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Ala Asp Val His Cys Pro Trp Ala Pro Phe Trp Cys Pro Val Asn Arg
1               5                   10                  15

Pro Gly Cys Ala
            20

<210> SEQ ID NO 130
```

```
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Ala Asp Val His Cys Pro Trp Gly Ala Phe Trp Cys Pro Val Asn Arg
1               5                   10                  15

Pro Gly Cys Ala
            20

<210> SEQ ID NO 131
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: 2-Aminoisobutyric acid

<400> SEQUENCE: 131

Ala Asp Val His Cys Pro Trp Gly Xaa Phe Trp Cys Pro Val Asn Arg
1               5                   10                  15

Pro Gly Cys Ala
            20

<210> SEQ ID NO 132
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Ala Asp Val His Cys Pro Trp Gly Pro Phe Trp Cys Ala Pro Val Asn
1               5                   10                  15

Arg Pro Gly Cys Ala
            20

<210> SEQ ID NO 133
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 133

Xaa Xaa Ala Asp Val Thr Cys Pro Trp Gly Pro Phe Trp Cys Pro Val
1               5                   10                  15

Asn Arg Pro Gly Cys
            20
```

```
<210> SEQ ID NO 134
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (5)..(5)
<223> OTHER INFORMATION: Tert-leucine

<400> SEQUENCE: 134

Xaa Xaa Ala Asp Xaa Thr Cys Pro Trp Gly Pro Phe Trp Cys Pro Val
1               5                   10                  15

Asn Arg Pro Gly Cys
            20

<210> SEQ ID NO 135
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: 1-Naphthylalanine

<400> SEQUENCE: 135

Ala His Asp Val Pro Cys Pro Xaa Gly Pro Phe Trp Cys Pro Val Asn
1               5                   10                  15

Arg Pro Gly Cys Ala
            20

<210> SEQ ID NO 136
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: 1-Naphthylalanine

<400> SEQUENCE: 136

Ala His Asp Val Pro Cys Pro Xaa Gly Pro Phe Trp Cys Pro Val Asn
1               5                   10                  15

Arg Pro Gly Cys
            20

<210> SEQ ID NO 137
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: MOD_RES
<222> LOCATION: (12)..(12)
<223> OTHER INFORMATION: 1-Naphthylalanine

<400> SEQUENCE: 137

Ala His Asp Val Pro Cys Pro Trp Gly Pro Phe Xaa Cys Pro Val Asn
1               5                   10                  15

Arg Pro Gly Cys
        20

<210> SEQ ID NO 138
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: 1-Naphthylalanine
<220> FEATURE:
<221> NAME/KEY: MOD_RES
<222> LOCATION: (15)..(15)
<223> OTHER INFORMATION: Tert-leucine

<400> SEQUENCE: 138

Ala His Asp Val Pro Cys Pro Xaa Gly Pro Phe Trp Cys Pro Xaa Asn
1               5                   10                  15

Arg Pro Gly Cys
        20

<210> SEQ ID NO 139
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: 1-Naphthylalanine
<220> FEATURE:
<221> NAME/KEY: MOD_RES
<222> LOCATION: (10)..(10)
<223> OTHER INFORMATION: 2-Aminoisobutyric acid
<220> FEATURE:
<221> NAME/KEY: MOD_RES
<222> LOCATION: (15)..(15)
<223> OTHER INFORMATION: Tert-leucine
<220> FEATURE:
<221> NAME/KEY: MOD_RES
<222> LOCATION: (17)..(17)
<223> OTHER INFORMATION: Homoarginine

<400> SEQUENCE: 139

Ala His Asp Val Pro Cys Pro Xaa Gly Xaa Phe Trp Cys Pro Xaa Asn
1               5                   10                  15

Xaa Pro Gly Cys
        20

<210> SEQ ID NO 140
<211> LENGTH: 20
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: 1-Naphthylalanine
<220> FEATURE:
<221> NAME/KEY: MOD_RES
<222> LOCATION: (10)..(10)
<223> OTHER INFORMATION: 2-Aminoisobutyric acid
<220> FEATURE:
<221> NAME/KEY: MOD_RES
<222> LOCATION: (15)..(15)
<223> OTHER INFORMATION: Tert-leucine
<220> FEATURE:
<221> NAME/KEY: MOD_RES
<222> LOCATION: (18)..(18)
<223> OTHER INFORMATION: 2-Aminoisobutyric acid

<400> SEQUENCE: 140

Ala His Asp Val Pro Cys Pro Xaa Gly Xaa Phe Trp Cys Pro Xaa Asn
1               5                  10                  15

Arg Xaa Gly Cys
            20

<210> SEQ ID NO 141
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 141

Xaa Xaa Ala His Asp Val Pro Cys Pro Trp Gly Pro Phe Trp Cys Pro
1               5                  10                  15

Val Asn Arg Pro Gly Cys
            20

<210> SEQ ID NO 142
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 142

Xaa Xaa Ala Ala Asp Val Pro Cys Pro Trp Gly Pro Phe Trp Cys Pro
1               5                  10                  15

Val Asn Arg Pro Gly Cys
            20

<210> SEQ ID NO 143
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                          Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (4)..(4)
<223> OTHER INFORMATION: 2-Thienylalanine

<400> SEQUENCE: 143

Xaa Xaa Ala Xaa Asp Val Pro Cys Pro Trp Gly Pro Phe Trp Cys Pro
1               5                   10                  15

Val Asn Arg Pro Gly Cys
            20

<210> SEQ ID NO 144
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (4)..(4)
<223> OTHER INFORMATION: 3-(1,2,4-triazol-1-yl)-Alanine

<400> SEQUENCE: 144

Xaa Xaa Ala Xaa Asp Val Pro Cys Pro Trp Gly Pro Phe Trp Cys Pro
1               5                   10                  15

Val Asn Arg Pro Gly Cys
            20

<210> SEQ ID NO 145
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (4)..(4)
<223> OTHER INFORMATION: 2-Furylalanine

<400> SEQUENCE: 145

Xaa Xaa Ala Xaa Asp Val Pro Cys Pro Trp Gly Pro Phe Trp Cys Pro
1               5                   10                  15

Val Asn Arg Pro Gly Cys
            20

<210> SEQ ID NO 146
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (1)..(2)
<223> OTHER INFORMATION: Sarcosine

<400> SEQUENCE: 146

Xaa Xaa Ala His Ala Val Pro Cys Pro Trp Gly Pro Phe Trp Cys Pro
1               5                   10                  15

Val Asn Arg Pro Gly Cys
            20

<210> SEQ ID NO 147
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 147

Xaa Xaa Ala His Glu Val Pro Cys Pro Trp Gly Pro Phe Trp Cys Pro
1               5                   10                  15

Val Asn Arg Pro Gly Cys
            20

<210> SEQ ID NO 148
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 148

Xaa Xaa Ala His Asp Ala Pro Cys Pro Trp Gly Pro Phe Trp Cys Pro
1               5                   10                  15

Val Asn Arg Pro Gly Cys
            20

<210> SEQ ID NO 149
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: 2-Aminoisobutyric acid

<400> SEQUENCE: 149

Xaa Xaa Ala His Asp Xaa Pro Cys Pro Trp Gly Pro Phe Trp Cys Pro
1               5                   10                  15
```

```
Val Asn Arg Pro Gly Cys
            20

<210> SEQ ID NO 150
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (6)..(6)
<223> OTHER INFORMATION: Tert-leucine

<400> SEQUENCE: 150

Xaa Xaa Ala His Asp Xaa Pro Cys Pro Trp Gly Pro Phe Trp Cys Pro
1               5                   10                  15

Val Asn Arg Pro Gly Cys
            20

<210> SEQ ID NO 151
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 151

Xaa Xaa Ala His Asp Val Ala Cys Pro Trp Gly Pro Phe Trp Cys Pro
1               5                   10                  15

Val Asn Arg Pro Gly Cys
            20

<210> SEQ ID NO 152
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (7)..(7)
<223> OTHER INFORMATION: 2-Aminoisobutyric acid

<400> SEQUENCE: 152

Xaa Xaa Ala His Asp Val Xaa Cys Pro Trp Gly Pro Phe Trp Cys Pro
1               5                   10                  15

Val Asn Arg Pro Gly Cys
            20
```

```
<210> SEQ ID NO 153
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (7)..(7)
<223> OTHER INFORMATION: Azetidine

<400> SEQUENCE: 153

Xaa Xaa Ala His Asp Val Xaa Cys Pro Trp Gly Pro Phe Trp Cys Pro
1               5                   10                  15

Val Asn Arg Pro Gly Cys
            20

<210> SEQ ID NO 154
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine
<220> FEATURE:
<221> NAME/KEY: MOD_RES
<222> LOCATION: (7)..(7)
<223> OTHER INFORMATION: Pipecolic acid

<400> SEQUENCE: 154

Xaa Xaa Ala His Asp Val Xaa Cys Pro Trp Gly Pro Phe Trp Cys Pro
1               5                   10                  15

Val Asn Arg Pro Gly Cys
            20

<210> SEQ ID NO 155
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 155

Xaa Xaa Xaa Xaa Xaa Xaa Xaa Xaa Xaa Xaa His Asp Val Pro Cys
1               5                   10                  15

Pro Trp Gly Pro Phe Trp Cys Pro Val Asn Arg Pro Gly Cys
            20                  25                  30

<210> SEQ ID NO 156
```

```
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 156

Xaa Xaa Ala Cys Ala Trp Gly Pro Phe Trp Cys Pro Val Asn Arg Pro
1               5                   10                  15

Gly Cys

<210> SEQ ID NO 157
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 157

Xaa Xaa Ala Cys Pro Ala Gly Pro Phe Trp Cys Pro Val Asn Arg Pro
1               5                   10                  15

Gly Cys

<210> SEQ ID NO 158
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 158

Xaa Xaa Ala Cys Pro Trp Ala Pro Phe Trp Cys Pro Val Asn Arg Pro
1               5                   10                  15

Gly Cys

<210> SEQ ID NO 159
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 159

Xaa Xaa Ala Cys Pro Trp Gly Ala Phe Trp Cys Pro Val Asn Arg Pro
1               5                   10                  15
```

Gly Cys

<210> SEQ ID NO 160
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 160

Xaa Xaa Ala Cys Pro Trp Gly Pro Phe Ala Cys Pro Val Asn Arg Pro
1               5                   10                  15

Gly Cys

<210> SEQ ID NO 161
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 161

Xaa Xaa Ala Cys Pro Trp Gly Pro Phe Trp Cys Ala Val Asn Arg Pro
1               5                   10                  15

Gly Cys

<210> SEQ ID NO 162
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 162

Xaa Xaa Ala Cys Pro Trp Gly Pro Phe Trp Cys Pro Ala Asn Arg Pro
1               5                   10                  15

Gly Cys

<210> SEQ ID NO 163
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: Sarcosine

<400> SEQUENCE: 163

Xaa Xaa Ala Cys Pro Trp Gly Pro Phe Trp Cys Pro Val Asn Ala Pro
1               5                   10                  15

Gly Cys

<210> SEQ ID NO 164
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 164

Xaa Xaa Xaa Xaa Xaa Xaa Xaa Xaa Xaa Xaa Xaa Ala Cys Pro Trp Ala
1               5                   10                  15

Pro Phe Trp Cys Ala Val Asn Arg Pro Gly Cys
            20                  25

<210> SEQ ID NO 165
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 165

Xaa Xaa Xaa Xaa Xaa Xaa Xaa Xaa Xaa Xaa Xaa Ala Cys Pro Trp Ala
1               5                   10                  15

Pro Phe Trp Cys Ala Val Asn Arg Pro Gly Cys
            20                  25

<210> SEQ ID NO 166
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Ala Asp Val His Cys Pro Trp Ala Pro Phe Trp Cys Pro Val Asn Arg
1               5                   10                  15

Pro Gly Cys Ala
            20

```
<210> SEQ ID NO 167
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Ala Asp Val His Cys Pro Trp Gly Ala Phe Trp Cys Pro Val Asn Arg
1               5                   10                  15

Pro Gly Cys Ala
            20

<210> SEQ ID NO 168
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 168

Xaa Xaa Xaa Xaa Xaa Xaa Xaa Xaa Xaa Xaa Xaa Ala Cys Pro Trp Ala
1               5                   10                  15

Pro Phe Trp Cys Ala Val Asn Arg Pro Gly Cys
            20                  25

<210> SEQ ID NO 169
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 169

Ala Cys Met Asn Asp Trp Trp Cys Ala Met Gly Trp Lys Cys Ala Xaa
1               5                   10                  15

Xaa Xaa Xaa Xaa Xaa Lys
            20

<210> SEQ ID NO 170
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine
```

-continued

```
<400> SEQUENCE: 170

Ala Cys Val Pro Asp Arg Arg Cys Ala Tyr Met Asn Val Cys Ala Xaa
1               5                   10                  15

Xaa Xaa Xaa Xaa Xaa Lys
            20

<210> SEQ ID NO 171
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 171

Ala Cys Val Val Asp Gly Arg Cys Ala Tyr Met Asn Val Cys Ala Xaa
1               5                   10                  15

Xaa Xaa Xaa Xaa Xaa Lys
            20

<210> SEQ ID NO 172
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 172

Ala Cys Val Val Asp Ser Arg Cys Ala Tyr Met Asn Val Cys Ala Xaa
1               5                   10                  15

Xaa Xaa Xaa Xaa Xaa Lys
            20

<210> SEQ ID NO 173
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 173

Ala Cys Val Pro Asp Ser Arg Cys Ala Tyr Met Asn Val Cys Ala Xaa
1               5                   10                  15

Xaa Xaa Xaa Xaa Xaa Lys
            20

<210> SEQ ID NO 174
<211> LENGTH: 22
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 174

Ala Cys Tyr Val Gly Lys Glu Cys Ala Ile Arg Asn Val Cys Ala Xaa
1               5                   10                  15

Xaa Xaa Xaa Xaa Xaa Lys
            20

<210> SEQ ID NO 175
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16)..(21)
<223> OTHER INFORMATION: Sarcosine

<400> SEQUENCE: 175

Ala Cys Tyr Val Gly Lys Glu Cys Ala Tyr Met Asn Val Cys Ala Xaa
1               5                   10                  15

Xaa Xaa Xaa Xaa Xaa Lys
            20

<210> SEQ ID NO 176
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(6)
<223> OTHER INFORMATION: Sarcosine

<400> SEQUENCE: 176

Gly Xaa Xaa Xaa Xaa Xaa Ala Cys Tyr Val Gly Lys Glu Cys Ala Tyr
1               5                   10                  15

Met Asn Val Cys Ala
            20

<210> SEQ ID NO 177
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine
```

-continued

<400> SEQUENCE: 177

Xaa Xaa Xaa Xaa Xaa Xaa Xaa Xaa Xaa Xaa Xaa Ala Arg Asp Cys Pro
1               5                   10                  15

Leu Val Asn Pro Leu Cys Leu His Pro Gly Trp Thr Cys
            20                  25

<210> SEQ ID NO 178
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine
<220> FEATURE:
<221> NAME/KEY: MOD_RES
<222> LOCATION: (13)..(13)
<223> OTHER INFORMATION: Homoarginine

<400> SEQUENCE: 178

Xaa Xaa Xaa Xaa Xaa Xaa Xaa Xaa Xaa Xaa Xaa Ala Xaa Asp Cys Pro
1               5                   10                  15

Leu Val Asn Pro Leu Cys Leu His Pro Gly Trp Thr Cys
            20                  25

<210> SEQ ID NO 179
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Ala Cys Met Asn Asp Trp Trp Cys Ala Met Gly Trp Lys Cys Ala
1               5                   10                  15

<210> SEQ ID NO 180
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Ala Cys Val Pro Asp Arg Arg Cys Ala Tyr Met Asn Val Cys Ala
1               5                   10                  15

<210> SEQ ID NO 181
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES

```
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 181

Xaa Xaa Xaa Xaa Xaa Xaa Xaa Xaa Xaa Xaa Xaa Ala Cys Val Pro Asp
1               5                   10                  15

Arg Arg Cys Ala Tyr Met Asn Val Cys
            20                  25

<210> SEQ ID NO 182
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Asp Leu Arg Cys Gly Gly Asp Pro Arg Cys Ala Tyr Met Asn Val Cys
1               5                   10                  15

Ala

<210> SEQ ID NO 183
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Ser Arg Pro Cys Val Ile Asp Ser Arg Cys Ala Tyr Met Asn Val Cys
1               5                   10                  15

Ala

<210> SEQ ID NO 184
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Glu Ser Arg Cys Ser Pro Asp Ala Arg Cys Ala Tyr Met Asn Val Cys
1               5                   10                  15

Ala

<210> SEQ ID NO 185
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

His Ser Gly Cys Arg Pro Asp Pro Arg Cys Ala Tyr Met Asn Val Cys
```

-continued

```
1               5                   10                  15
Ala

<210> SEQ ID NO 186
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Gly Ser Gly Cys Lys Pro Asp Ser Arg Cys Ala Tyr Met Asn Val Cys
1               5                   10                  15
Ala

<210> SEQ ID NO 187
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Glu Thr Val Cys Leu Pro Asp Ser Arg Cys Ala Tyr Met Asn Val Cys
1               5                   10                  15
Ala

<210> SEQ ID NO 188
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Gly Gln Val Cys Ile Val Asp Ala Arg Cys Ala Tyr Met Asn Val Cys
1               5                   10                  15
Ala

<210> SEQ ID NO 189
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Ala Cys Val Pro Asp Arg Arg Cys Ala Phe Glu Asn Val Cys Val Asp
1               5                   10                  15
His

<210> SEQ ID NO 190
<211> LENGTH: 17
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 190

Ala Cys Val Pro Asp Arg Arg Cys Ala Phe Met Asn Val Cys Glu Asp
1               5                   10                  15

Arg

<210> SEQ ID NO 191
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Ala Cys Val Pro Asp Arg Arg Cys Ala Phe Gln Asp Val Cys Asp His
1               5                   10                  15

Glu

<210> SEQ ID NO 192
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Ala Cys Val Pro Asp Arg Arg Cys Ala Phe Arg Asp Val Cys Leu Thr
1               5                   10                  15

Gly

<210> SEQ ID NO 193
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Ala Cys Tyr Val Gly Lys Glu Cys Ala Tyr Met Asn Val Cys Ala
1               5                   10                  15

<210> SEQ ID NO 194
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Ala Cys Gln Pro Ser Asn His Cys Ala Phe Met Asn Tyr Cys Ala
1               5                   10                  15

<210> SEQ ID NO 195
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 195

Ala Cys Ser Pro Thr Pro Ala Cys Ala Val Gln Asn Leu Cys Ala
1               5                   10                  15

<210> SEQ ID NO 196
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Ala Cys Thr Ser Cys Trp Ala Tyr Pro Asp Ser Phe Cys Ala
1               5                   10

<210> SEQ ID NO 197
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Ala Cys Thr Lys Pro Thr Gly Phe Cys Ala Tyr Pro Asp Thr Ile Cys
1               5                   10                  15

Ala

<210> SEQ ID NO 198
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Ala Cys Arg Gly Glu Trp Gly Tyr Cys Ala Tyr Pro Asp Thr Ile Cys
1               5                   10                  15

Ala

<210> SEQ ID NO 199
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Ala Cys Arg Asn Trp Gly Met Tyr Cys Ala Tyr Pro Asp Thr Ile Cys
1               5                   10                  15

Ala

<210> SEQ ID NO 200
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Ala Cys Pro Asp Trp Gly Lys Tyr Cys Ala Tyr Pro Asp Thr Ile Cys
1               5                   10                  15

Ala

<210> SEQ ID NO 201
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Ala Cys Arg Val Tyr Gly Pro Tyr Cys Ala Tyr Pro Asp Thr Ile Cys
1               5                   10                  15

Ala

<210> SEQ ID NO 202
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Ala Cys Ser Ser Cys Trp Ala Tyr Pro Asp Ser Val Cys Ala
1               5                   10

<210> SEQ ID NO 203
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Ala Cys Gln Ser Cys Trp Ala Tyr Pro Asp Thr Tyr Cys Ala
1               5                   10

<210> SEQ ID NO 204
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Ala Cys Gly Phe Met Gly Leu Glu Pro Cys Glu Thr Phe Cys Ala
1               5                   10                  15

<210> SEQ ID NO 205
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Ala Cys Gly Phe Met Gly Leu Val Pro Cys Glu Val His Cys Ala
1               5                   10                  15

<210> SEQ ID NO 206
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Ala Cys Gly Phe Met Gly Leu Glu Pro Cys Glu Met Val Cys Ala
1               5                   10                  15

<210> SEQ ID NO 207
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Ala Cys Gly Phe Met Gly Leu Glu Pro Cys Val Thr Tyr Cys Ala
1               5                   10                  15

<210> SEQ ID NO 208
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Ala Cys Gly Phe Met Gly Leu Glu Pro Cys Glu Leu Val Cys Ala
1               5                   10                  15

<210> SEQ ID NO 209
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Ala Cys Gly Phe Met Gly Leu Val Pro Cys Asn Val Phe Cys Ala
1               5                   10                  15

<210> SEQ ID NO 210
<211> LENGTH: 15
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 210

Ala Cys Gly Phe Met Gly Leu Glu Pro Cys Glu Leu Phe Cys Ala
1               5                   10                  15

<210> SEQ ID NO 211
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Ala Cys Gly Phe Met Gly Leu Glu Pro Cys Glu Leu Phe Cys Met Pro
1               5                   10                  15

Lys

<210> SEQ ID NO 212
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Ala Cys Gly Phe Met Gly Leu Glu Pro Cys Glu Leu Tyr Cys Ala
1               5                   10                  15

<210> SEQ ID NO 213
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Ala Cys Gly Phe Met Gly Leu Glu Pro Cys Glu Leu Tyr Cys Ala His
1               5                   10                  15

Thr

<210> SEQ ID NO 214
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Ala Cys Gly Phe Met Gly Leu Glu Pro Cys Glu Met Tyr Cys Ala
1               5                   10                  15

<210> SEQ ID NO 215
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Ala Cys Gly Phe Met Gly Leu Val Pro Cys Glu Leu Tyr Cys Ala Asp
1               5                   10                  15

Asn

<210> SEQ ID NO 216
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Ala Cys Pro Leu Val Asn Pro Leu Cys Leu Thr Ser Gly Trp Lys Cys
1               5                   10                  15

Ala

<210> SEQ ID NO 217
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Ala Cys Pro Met Val Asn Pro Leu Cys Leu His Pro Gly Trp Ile Cys
1               5                   10                  15

Ala

<210> SEQ ID NO 218
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Ala Cys Pro Leu Val Asn Pro Leu Cys Leu His Pro Gly Trp Ile Cys
1               5                   10                  15

Ala

<210> SEQ ID NO 219
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Ala Cys Pro Leu Val Asn Pro Leu Cys Leu His Pro Gly Trp Arg Cys
1               5                   10                  15

Ala

-continued

<210> SEQ ID NO 220
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Ala Cys Pro Leu Val Asn Pro Leu Cys Asn Leu Pro Gly Trp Thr Cys
1               5                   10                  15

Ala

<210> SEQ ID NO 221
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Ala Cys Pro Leu Val Asn Pro Leu Cys Leu Val Pro Gly Trp Ser Cys
1               5                   10                  15

Ala

<210> SEQ ID NO 222
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Ala Cys Pro Leu Val Asn Pro Leu Cys Leu Leu Asp Gly Trp Thr Cys
1               5                   10                  15

Ala

<210> SEQ ID NO 223
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Ala Cys Pro Leu Val Asn Pro Leu Cys Leu Met Pro Gly Trp Gly Cys
1               5                   10                  15

Ala

<210> SEQ ID NO 224
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

```
Ala Cys Pro Leu Val Asn Pro Leu Cys Met Ile Gly Asn Trp Thr Cys
1               5                   10                  15

Ala

<210> SEQ ID NO 225
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Ala Cys Pro Leu Val Asn Pro Leu Cys Leu Met Thr Gly Trp Ser Cys
1               5                   10                  15

Ala

<210> SEQ ID NO 226
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Ala Cys Pro Leu Val Asn Pro Leu Cys Met Met Gly Gly Trp Lys Cys
1               5                   10                  15

Ala

<210> SEQ ID NO 227
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Ala Cys Pro Leu Val Asn Pro Leu Cys Leu Tyr Gly Ser Trp Lys Cys
1               5                   10                  15

Ala

<210> SEQ ID NO 228
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Ala Cys Pro Leu Val Asn Pro Leu Cys Leu His Pro Gly Trp Thr Cys
1               5                   10                  15

Ala

<210> SEQ ID NO 229
<211> LENGTH: 19
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"

<400> SEQUENCE: 229

Ala Arg Asp Cys Pro Leu Val Asn Pro Leu Cys Leu His Pro Gly Trp
1               5                   10                  15

Thr Cys Ala

<210> SEQ ID NO 230
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 230

Xaa Xaa Xaa Xaa Xaa Xaa Xaa Xaa Xaa Xaa Xaa Ala Arg Asp Cys Pro
1               5                   10                  15

Leu Val Asn Pro Leu Cys Leu His Pro Gly Trp Thr Cys
            20                  25

<210> SEQ ID NO 231
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine
<220> FEATURE:
<221> NAME/KEY: MOD_RES
<222> LOCATION: (13)..(13)
<223> OTHER INFORMATION: Homoarginine

<400> SEQUENCE: 231

Xaa Xaa Xaa Xaa Xaa Xaa Xaa Xaa Xaa Xaa Xaa Ala Xaa Asp Cys Pro
1               5                   10                  15

Leu Val Asn Pro Leu Cys Leu His Pro Gly Trp Thr Cys
            20                  25

<210> SEQ ID NO 232
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232
```

Arg Pro Ala Cys Pro Leu Val Asn Pro Leu Cys Leu His Pro Gly Trp
1               5                   10                  15

Thr Cys Ala

<210> SEQ ID NO 233
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Arg Pro Pro Cys Pro Leu Val Asn Pro Leu Cys Leu His Pro Gly Trp
1               5                   10                  15

Thr Cys Ala

<210> SEQ ID NO 234
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Lys His Ser Cys Pro Leu Val Asn Pro Leu Cys Leu His Pro Gly Trp
1               5                   10                  15

Thr Cys Ala

<210> SEQ ID NO 235
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Ala Cys Pro Leu Val Asn Pro Leu Cys Leu His Pro Gly Trp Thr Cys
1               5                   10                  15

Leu His Gly

<210> SEQ ID NO 236
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Cys Pro Leu Val Asn Pro Leu Cys Leu His Pro Gly Trp Thr Cys Leu
1               5                   10                  15

His Gly

<210> SEQ ID NO 237
<211> LENGTH: 30
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 237

Xaa Xaa Xaa Xaa Xaa Xaa Xaa Xaa Xaa Xaa Xaa Ala Cys Pro Leu Val
1               5                   10                  15

Asn Pro Leu Cys Leu His Pro Gly Trp Thr Cys Leu His Gly
            20                  25                  30

<210> SEQ ID NO 238
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: 2-Naphthylalanine

<400> SEQUENCE: 238

Ala Cys Pro Leu Val Asn Pro Leu Cys Leu His Pro Gly Xaa Thr Cys
1               5                   10                  15

Leu His Gly

<210> SEQ ID NO 239
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Arg His Asp Cys Pro Leu Val Asn Pro Leu Cys Leu Leu Pro Gly Trp
1               5                   10                  15

Thr Cys Ala

<210> SEQ ID NO 240
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Thr Pro Arg Cys Pro Leu Val Asn Pro Leu Cys Leu Met Pro Gly Trp
1               5                   10                  15

Thr Cys Ala

<210> SEQ ID NO 241
<211> LENGTH: 17
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Ala Cys Pro Leu Val Asn Pro Leu Cys Leu Ala Pro Gly Trp Thr Cys
1               5                   10                  15

Ala

<210> SEQ ID NO 242
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Ala Cys Pro Leu Val Asn Pro Leu Cys Leu Ala Pro Gly Trp Thr Cys
1               5                   10                  15

Ser Arg Ser

<210> SEQ ID NO 243
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Ala Cys Pro Leu Val Asn Pro Leu Cys Leu Glu Pro Gly Trp Thr Cys
1               5                   10                  15

Ala

<210> SEQ ID NO 244
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Ala Cys Pro Leu Val Asn Pro Leu Cys Leu Glu Pro Gly Trp Thr Cys
1               5                   10                  15

Ala Lys Arg

<210> SEQ ID NO 245
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Ala Cys Pro Leu Val Asn Pro Leu Cys Leu His Pro Gly Trp Ser Cys
1               5                   10                  15
```

Ala

<210> SEQ ID NO 246
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Ala Cys Pro Leu Val Asn Pro Leu Cys Leu His Pro Gly Trp Ser Cys
1               5                   10                  15

Arg Gly Gln

<210> SEQ ID NO 247
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Cys Pro Leu Val Asn Pro Leu Cys Leu His Pro Gly Trp Ser Cys Arg
1               5                   10                  15

Gly Gln

<210> SEQ ID NO 248
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

<400> SEQUENCE: 248

Xaa Xaa Xaa Xaa Xaa Xaa Xaa Xaa Xaa Xaa Xaa Ala Cys Pro Leu Val
1               5                   10                  15

Asn Pro Leu Cys Leu His Pro Gly Trp Ser Cys Arg Gly Gln
            20                  25                  30

<210> SEQ ID NO 249
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(11)
<223> OTHER INFORMATION: Sarcosine

```
<220> FEATURE:
<221> NAME/KEY: MOD_RES
<222> LOCATION: (28)..(28)
<223> OTHER INFORMATION: Homoarginine

<400> SEQUENCE: 249

Xaa Xaa Xaa Xaa Xaa Xaa Xaa Xaa Xaa Xaa Xaa Ala Cys Pro Leu Val
1               5                   10                  15

Asn Pro Leu Cys Leu His Pro Gly Trp Ser Cys Xaa Gly Gln
            20                  25                  30

<210> SEQ ID NO 250
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: 2-Naphthylalanine

<400> SEQUENCE: 250

Ala Cys Pro Leu Val Asn Pro Leu Cys Leu His Pro Gly Xaa Ser Cys
1               5                   10                  15

Arg Gly Gln

<210> SEQ ID NO 251
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Ala Cys Pro Leu Val Asn Pro Leu Cys Leu Thr Pro Gly Trp Thr Cys
1               5                   10                  15

Thr Asn Thr

<210> SEQ ID NO 252
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Ala Cys Pro Met Val Asn Pro Leu Cys Leu His Pro Gly Trp Lys Cys
1               5                   10                  15

Ala

<210> SEQ ID NO 253
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253
```

-continued

```
Ala Cys Pro Met Val Asn Pro Leu Cys Leu Thr Pro Gly Trp Ile Cys
1               5                   10                  15
Ala
```

<210> SEQ ID NO 254
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 254

```
Ala Cys Pro Met Val Asn Pro Leu Cys Leu His Pro Gly Trp Thr Cys
1               5                   10                  15
Ala
```